United States Patent
Iwaki et al.

(10) Patent No.: US 11,873,521 B2
(45) Date of Patent: Jan. 16, 2024

(54) STEVIOL GLYCOSIDE AND PRODUCTION METHOD THEREFOR, AND SWEETENER COMPOSITION CONTAINING SAME

(71) Applicant: SUNTORY HOLDINGS LIMITED, Osaka (JP)

(72) Inventors: Kazunari Iwaki, Kyoto (JP); Katsuro Miyagawa, Kyoto (JP); Eiichiro Ono, Kyoto (JP); Tadayoshi Hirai, Kyoto (JP); Misa Ochiai, Kyoto (JP); Koji Nagao, Kanagawa (JP); Soichiro Urai, Kanagawa (JP); Takehiro Watanabe, Kyoto (JP); Kohki Fujikawa, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 214 days.

(21) Appl. No.: 16/498,034

(22) PCT Filed: Mar. 28, 2018

(86) PCT No.: PCT/JP2018/012845
§ 371 (c)(1),
(2) Date: Sep. 26, 2019

(87) PCT Pub. No.: WO2018/181515
PCT Pub. Date: Oct. 4, 2018

(65) Prior Publication Data
US 2020/0224235 A1    Jul. 16, 2020

(30) Foreign Application Priority Data
Mar. 31, 2017    (JP) .................................. 2017-071457

(51) Int. Cl.
*C12P 19/44*    (2006.01)
*A23L 27/30*    (2016.01)
(Continued)

(52) U.S. Cl.
CPC ................ *C12P 19/44* (2013.01); *A23L 2/60* (2013.01); *A23L 27/36* (2016.08); *C12N 1/16* (2013.01)

(58) Field of Classification Search
CPC .. C12P 19/44; C12P 19/56; A23L 2/60; A23L 27/36; A23L 27/00; A23L 27/20; C12N 1/16; Y02P 20/55; C07H 15/256
See application file for complete search history.

(56) References Cited

U.S. PATENT DOCUMENTS 4,361,697 A    11/1982 Dobberstein et al.
4,612,942 A *   9/1986 Dobberstein ........... A23F 3/405
                                                                426/77
(Continued)

FOREIGN PATENT DOCUMENTS

CN    104286779 A    1/2015
JP    H10-271928 A    10/1998
(Continued)

OTHER PUBLICATIONS

"How is Stevia Leaf Extract Made?", Stevia.com, Nov. 9, 2016 [online], [retrieved Nov. 22, 2021]. Retrieved from the Internet <https://www.stevia.com/2016/10/03/how-is-stevia-leaf-extract-made/> (Year: 2016).*

(Continued)

*Primary Examiner* — Donald R Spamer
*Assistant Examiner* — Jeffrey D Benson
(74) *Attorney, Agent, or Firm* — GREENBLUM & BERNSTEIN, P.L.C.

(57) ABSTRACT

The purpose of the present invention is to: determine the structure of a novel steviol glycoside which is detected from species containing a large amount of Reb. C (also referred to as dulcoside B), and a trace amount of which is capable of (Continued)

influencing the quality of taste; and understand the taste characteristics of said steviol glycoside. The present invention provides a compound represented by formula (1) or a salt thereof, or a hydrate thereof.

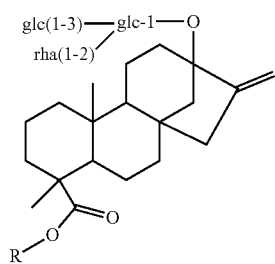

(1)

3 Claims, 14 Drawing Sheets

Specification includes a Sequence Listing.

(51) Int. Cl.
A23L 2/60 (2006.01)
C12N 1/16 (2006.01)

(56) References Cited

U.S. PATENT DOCUMENTS

| | | |
|---|---|---|
| 2010/0316782 A1 | 12/2010 | Shi et al. |
| 2011/0183056 A1 | 7/2011 | Morita et al. |
| 2015/0257424 A1 | 9/2015 | Catani et al. |
| 2018/0163244 A1 | 6/2018 | Anderson et al. |

FOREIGN PATENT DOCUMENTS

| | | |
|---|---|---|
| JP | 3436317 B2 | 8/2003 |
| JP | 2017-507141 A | 3/2017 |
| WO | 2009/149577 A1 | 12/2009 |
| WO | 2010/038911 A1 | 4/2010 |
| WO | 2010/146463 A2 | 12/2010 |
| WO | 2011/153378 A1 | 12/2011 |
| WO | 2014/146135 A2 | 9/2014 |
| WO | 2016/090460 A1 | 6/2016 |
| WO | 2016/196345 A1 | 12/2016 |

OTHER PUBLICATIONS

STN Structure Search—Jul. 19, 2021 (Year: 2021).*
Office Action issued in AU Patent Application No. 2018243332, dated May 25, 2021.
Brandle, "Genetic Control of Rebaudioside A and C Concentration in Leaves of the Sweet Herb, Stevia Rebaudiana", Can. J. Plant Sci., vol. 79, pp. 85-92 (1999).
Gardana et al., "Evaluation of Steviol and its Glycosides in Stevia rebaudiana Leaves and Commercial Sweetener by Ultra-high-performance Liquid Chromatography-mass Spectrometry", Journal of Chromatography A, vol. 1217, pp. 1463-1470 (2010).
Starratt et al., "Rebaudioside F, A Diterpene Glycoside from Stevia rebaudiana", Phytochemistry, vol. 59, pp. 367-370 (2002).
Ohta et al., "Characterization of Novel Steviol Glycosides from Leaves of Stevia rebaudiana Morita", Appl. Glycosci., vol. 57, pp. 199-209 (2010).
Ceunen et al., "Steviol Glycosides: Chemical Diversity, Metabolism, and Function", J. Nat. Prod., vol. 76, pp. 1201-1228 (2013).
International Search Report issued in PCT/JP2018/012845, dated Jun. 26, 2018, along with an English language translation.
Search Report and Written Opinion issued in Singapore Patent Application No. 11201908370V, dated May 19, 2020.
Extended European Search Report issued in EP Patent Application No. 18774610.2, dated Nov. 9, 2020.
Office Action issued in JP Patent Application No. 2019-510000, dated Jul. 21, 2020, along With an English-language translation.
Office Action issued in CN Patent Application No. 201880021489.7, dated Sep. 15, 2022, along with an English language translation.

* cited by examiner

Selected ion chromatogram of SIC-developed novel Stevia plant body (Sample 1) at m/z 1095.4

Selected ion chromatogram of SIC-developed novel Stevia plant body (Sample 1) at *m/z* 1257.5

MS/MS and MS³ fragmented mass spectra of Novel steviol glycoside 1 (corresponding to m/z 1095.4, Rt:28.73)

MS/MS and MS³ fragmented mass spectra of Novel steviol glycoside 2 (corresponding to m/z 1257.5, Rt:28.50)

(a)

$^1$H-NMR of compound 15 (800MHz, Pyr-d5)

(b)

$^{13}$C-NMR of compound 15 (200MHz, Pyr-d5)

(a) $^1H-^1H$ cosy of compound 15 (800MHz, Pyr-d5)

(b) HSQC of compound 15 (800MHz, Pyr-d5)

(a)

HMBC of compound 15 (800MHz, Pyr-d5)

(b)

TOCSY of compound 15 (800MHz, Pyr-d5)

NOESY of compound 15 (800MHz, Pyr-d5)

(a)

¹H-NMR of compound 17 (800MHz, Pyr-d5)

(b)

¹³C-NMR of compound 17 (200MHz, Pyr-d5)

(a)

1H-1H cosy of compound 17 (800MHz, Pyr-d5)

(b)

HSQC of compound 17 (800MHz, Pyr-d5)

(a)

HMBC of compound 17 (800MHz, Pyr-d5)

(b)

TOCSY of compound 17 (800MHz, Pyr-d5)

NOESY of compound 17 (800MHz, Pyr-d5)

Extracted ion chromatograms of Novel steviol glycoside 1 (Stevia leaf extract) and chemically synthesized product (β-form of Compound 15)

MS/MS and MS³ fragmented mass spectra of Novel steviol glycoside 1 (Stevia leaf extract) and chemically synthesized product (β-form of Compound 15)

Extracted ion chromatograms of Novel steviol glycoside 2 (Stevia leaf extract) and chemically synthesized product (β-form of Compound 17)

MS/MS and MS³ fragmented mass spectra of Novel steviol glycoside 2 (Stevia leaf extract) and chemically synthesized product (β-form of Compound 17)

Selected ion chromatogram of biosynthesized sample at m/z of 1095.4

Selected ion chromatogram of biosynthesized sample at m/z of 1257.5

US 11,873,521 B2

STEVIOL GLYCOSIDE AND PRODUCTION METHOD THEREFOR, AND SWEETENER COMPOSITION CONTAINING SAME

TECHNICAL FIELD

The present invention relates to a novel steviol glycoside, a method for producing the same, and a sweetener composition containing the same. Furthermore, the present invention also relates to a food or beverage, a plant, an extract thereof and a flavor controlling agent containing the novel steviol glycoside.

BACKGROUND ART

Leaves of *Stevia rebaudiana* contain a secondary metabolite called Steviol which is one type of diterpenoids, where steviol glycoside provides sweetness that is nearly 300 times the sweetness of sugar and is therefore utilized as a calorieless sweetener in the food industry. The demand for calorieless sweeteners is growing day by day as obesity has become a serious social problem worldwide and also for the sake of health promotion and reduction in the medical expenditure. Currently, aspartame and acesulfame potassium, which are artificially synthesized amino acid derivatives, are utilized as artificial sweeteners, but natural calorieless sweeteners like the steviol glycosides are expected to be safer and more likely to gain public acceptance.

The major steviol glycosides from stevia are ultimately glycosylated to a glycoside named rebaudioside A (Reb.A) that has four sugar moieties (FIG. 1). Stevioside, namely, a tri-glycosylated steviol glycoside and a precursor of Reb.A, is the most abundant glycoside. These two glycosides are the main substances responsible for the sweetness of stevia. Stevioside accounts for the largest content in stevia leaves and is known to provide sweetness that is about 250-300 times the sweetness of sugar. Reb.A. is a tetra-glycosylated steviol glycoside that has strong sweetness (350-450 times sugar) with good taste quality. They have been drawing attention as calorieless sweeteners. Besides them, existence of glycosides that are considered to be reaction intermediates and analogs having different types of sugar moieties are known. For example, while all of the four glycoside sugar moieties of Reb.A are glucose, rebaudioside C (Reb.C) is known to have rhamnose instead of glucose attached to C-2 of glucose at C-13, and rebaudioside F (Reb.F) is known to have xylose attached at the same position.

To date, attempts have been made to obtain a stevia plant having a higher Reb.A content than wild-type stevia plants by breeding or the like since taste quality of Reb.A, in which all of the four glycoside sugar moieties are glucose, is good (for example, Patent document 1).

PRIOR ART DOCUMENT

Patent Document

Patent document 1: Japanese Patent No. 3436317

SUMMARY OF INVENTION

Problem to be Solved by the Invention

Meanwhile, some of the stevia cultivers resulting from breeding may contain a minute amount of a steviol glycoside whose structure is not yet identified, where the presence of such steviol glycoside present in minute quantity may potentially be contributing to the flavor characteristic of the stevia extract. Moreover, although researches have been made thus far on steviol glycosides obtained by further attaching glucose to Reb.A and on cultivers containing the same, not much research has been made at this point on a cultiver containing an abundant amount of a steviol glycoside having rhamnose like Reb.C and on such a steviol glycoside.

Accordingly, the objective of the present invention is to determine the structure of a novel steviol glycoside present in minute quantity that affects the taste quality, and to identify the characteristics of its taste quality. In addition, further objectives of the present invention are to provide a novel steviol glycoside, a method for producing the same, and a sweetener composition containing the same.

Means for Solving the Problem

The present inventors have gone through extensive investigation to solve the above-described problem, and as a result of which succeeded in determining the structure of the novel steviol glycoside present in minute quantity that affects the taste quality. The present invention was made based on the above-described finding.

EFFECT OF THE INVENTION

The present invention can provide a novel steviol glycoside present in minute quantity that affects the taste quality. Furthermore, the present invention can also provide a method for producing the novel steviol glycoside, and a sweetener composition, a food or beverage, a plant, an extract thereof and a flavor controlling agent containing the novel steviol glycoside.

MODES FOR CARRYING OUT THE INVENTION

Figure 1:
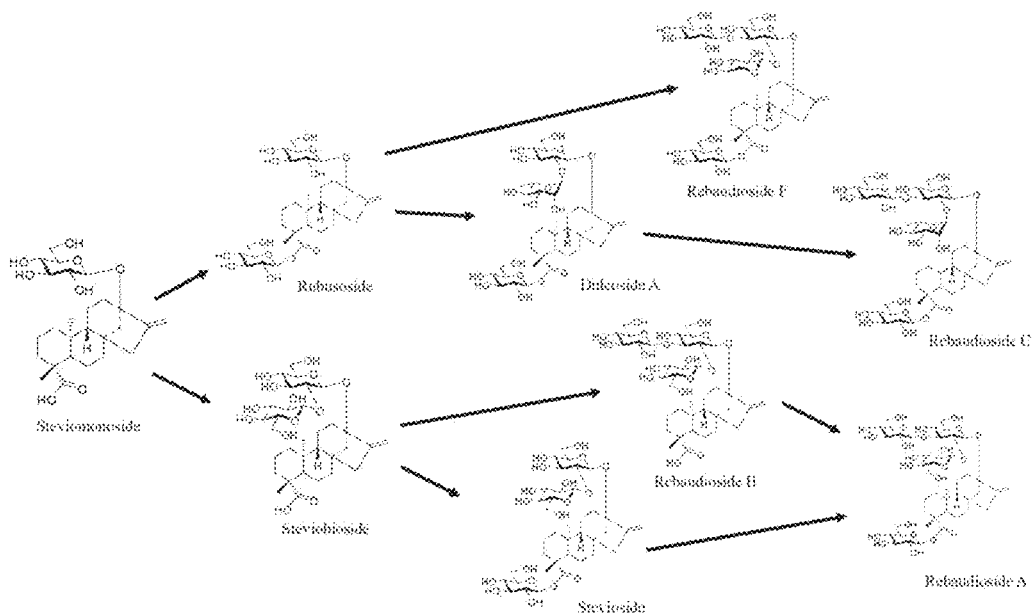
FIG. 1 illustrates a diagram showing structures and names of steviol glycosides.

Hereinafter, the present invention will be described in detail. The following embodiment is provided for illustrating the present invention and not with the intention of limiting the present invention solely to this embodiment. The present invention may be carried out in various modes without departing from the scope thereof. All of the documents, publications, patent publications and other patent documents cited herein are incorporated herein by reference.

The terms "rebaudioside" and "Reb." as used herein have the same meaning and both refer to "rebaudioside". Similarly, the terms "dulcoside" and "dulcoside" as used herein have the same meaning and both refer to "dulcoside".

1. Novel Steviol Glycoside

For the first time, the present inventors identified the structure of a minute amount of a novel steviol glycoside that affects taste quality. The novel steviol glycoside of the present invention (hereinafter, also referred to as the "glycoside of the present invention") is a compound represented by Formula (1):

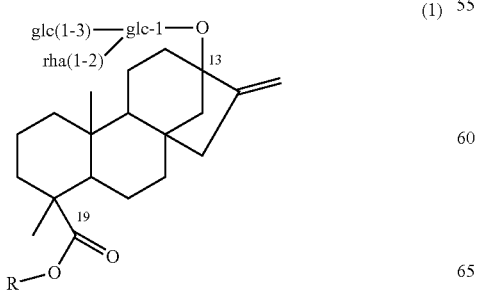

(1)

or a derivative, a salt or a hydrate thereof, wherein R represents a sugar chain of Formula (2) or (3); and

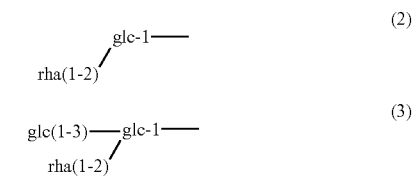

glc represents glucose, and rha represents rhamnose.

As represented above, the glycoside of the present invention has a sugar chain containing two glucose moieties and one rhamnose moiety at C-13 of steviol, and a sugar chain containing one glucose moiety and one rhamnose moiety, or two glucose moieties and one rhamnose moiety at C-19.

Furthermore, as represented above, glc represents glucose and rha represents rhamnose. "Glc" as used herein may be α- or β-glucose while rha may be α- or β-rhamnose. Alternatively, "glc" as used herein may be α- and β-glucose while rha may be α- and β-rhamnose. Moreover, "glc-1-" indicates that the carbon atom at C-1 of glucose is joined to steviol via a glycosidic bond, and "glc(1-3)-glc-1-" indicates that the carbon atom at C-3 of glucose represented by "glc-1-" is joined to a carbon atom at C-1 of another glucose via a glycosidic bond. Furthermore, "rha(1-2)-glc-1-" indicates that the carbon atom at C-2 of glucose represented by "glc-1-" is joined to a carbon atom at C-1 of rhamnose via a glycosidic bond.

Herein, among the compounds represented by Formula (1), those in which R has a sugar chain of Formula (2) are referred to as "Glycoside A" while those in which R has a sugar chain of Formula (3) are referred to as "Glycoside B".

Examples of Glycoside A include glycosides having the structures represented by Formulae (11) and (12).

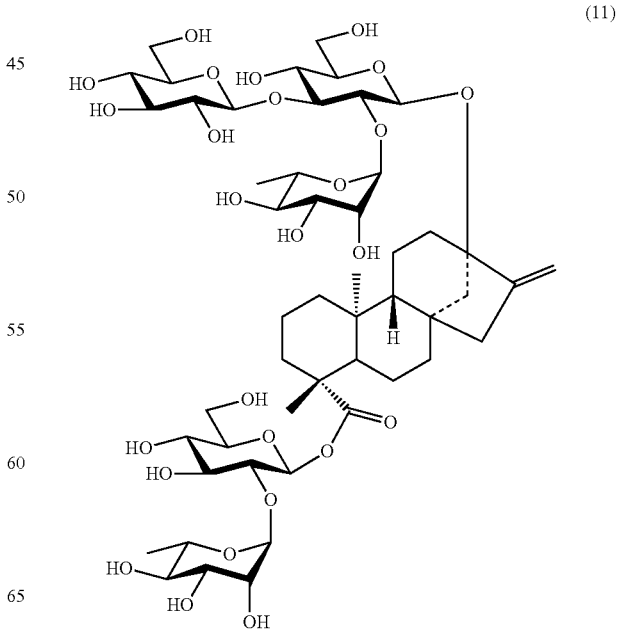

(11)

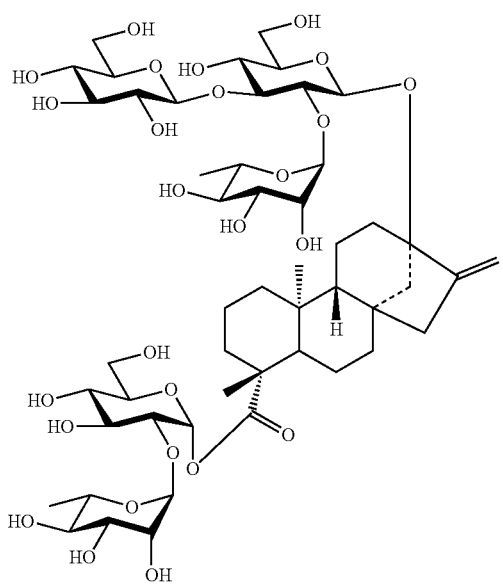
(12)

In Glycoside A represented by Formula (11), glucose is joined to the carboxylic group at C-19 of steviol via a β-glycosidic bond, whereas in Glycoside A represented by Formula (12), glucose is joined to the carboxylic group at C-19 of steviol via an α-glycosidic bond.

Examples of Glycoside B include glycosides having the structures represented by Formulae (13) and (14).

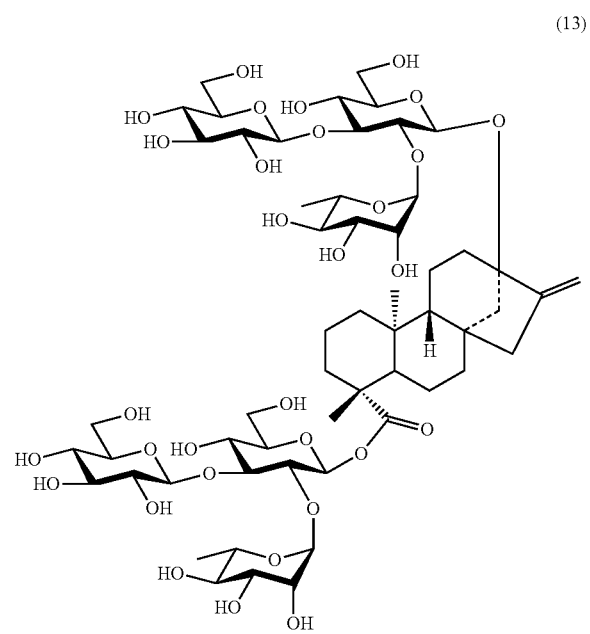
(13)

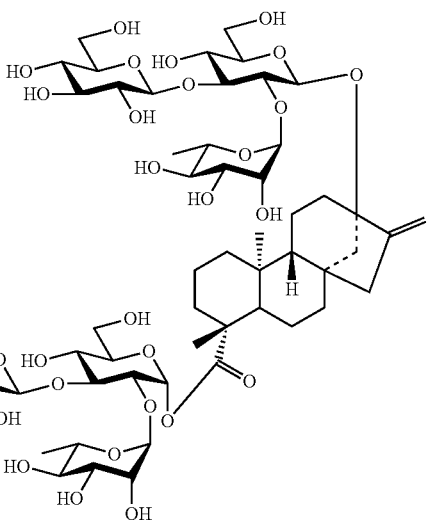
(14)

In Glycoside B represented by Formula (13), glucose is joined to the carboxylic group at C-19 of steviol via a β-glycosidic bond, whereas in Glycoside B represented by Formula (14), glucose is joined to the carboxylic group at C-19 of steviol via an α-glycosidic bond.

The glycoside of the present invention also comprises isomers such as the α- and β-forms as described above. Therefore, the glycoside of the present invention may comprise only those of the α-form, only those of the β-form or a mixture of the α- and β-forms. The glycoside of the present invention has the β-form in a proportion of preferably 80% or more, more preferably 90% or more, still more preferably 95% or more, and particularly preferably 99% or more. The α- and β-forms can be isolated/purified by a known method such as high-performance liquid chromatography (HPLC), ultra (high) performance liquid chromatography (UPLC), or the like.

The glycoside of the present invention may not only be the compound represented by Formula (1) but may also be a derivative, a salt or a hydrate thereof. The term "derivative" as used herein refers to a compound resulting from a structural change of a minor moiety of the compound, for example, a compound in which some of the hydroxyl groups are substituted with other substituents. Therefore, derivatives of the compound represented by Formula (1) include compounds in which some of the hydroxyl groups contained in the compound have been substituted with a substituent selected from hydrogen, a halogen, an alkyl group, an alkenyl group, an alkynyl group, an aryl group, an amino group, a cyano group or the like. As used herein, a "salt of the compound represented by Formula (1)" refers to a physiologically acceptable salt, for example, a sodium salt, of the compound represented by Formula (1). Furthermore, a "hydrate of the compound represented by Formula (1)" as used herein refers to a compound resulting from addition of a water molecule to the compound represented by Formula (1).

While the glycoside of the present invention is not particularly limited, it may be a plant-derived product, a chemically synthesized product or a biosynthetic product. For example, it may be isolated and purified from a plant with abundant Reb.C, or it may be obtained by chemical synthesis or biosynthesis. Details of a method for producing a glycoside of the present invention will be described later herein.

The glycoside of the present invention is sweeter than sugar (sucrose), has taste quality such as early sweetness onset and lingering aftertaste as good as sugar, and can affect the taste quality of foods/beverages in a small amount. Thus, the glycoside of the present invention can be used as a novel sweetener.

A glycoside in a preferable aspect of the present invention is selected from Glycoside A or Glycoside B. Glycoside B is sweeter than sugar (sucrose), has early sweetness onset, has sweet lingering as good as sugar, and is highly water soluble. Accordingly, it can favorably be used as a sweetener in various applications as will be described later. Glycoside A, although not much sweet as Glycoside B, is sweeter than sugar (sucrose), has early sweetness onset, and has sweet lingering as good as sugar. Similar to Glycoside B, Glycoside A can also favorably be used as a sweetener in various applications. Since it has lower water solubility than Glycoside B, it can particularly favorably be used in a lacto-fermented beverage, a suspended fruit juice drink, and a turbid beverage. It can also favorably be used for adjusting sweetness of a pharmaceutical product or the like. While not wishing to be bound by any theory, a low water solubility can suppress bitterness sensed by tongue while enhancing the stimulating feeling going down the throat, and thus advantageous for enhancing the body of the beverage.

2. Sweetener Composition Containing Novel Steviol Glycoside

In one aspect of the present invention, a sweetener composition containing the compound represented by Formula (1), or a derivative, a salt or a hydrate thereof (hereinafter, also referred to as the "sweetener composition of the present invention") is provided. The sweetener composition of the present invention is not particularly limited as long as it contains the compound represented by Formula (1), or a derivative, a salt or a hydrate thereof, and it may be a composition containing an extract containing the compound represented by Formula (1), or a derivative, a salt or a hydrate thereof.

The amount of the glycoside of the present invention contained in the sweetener composition of the present invention is not particularly limited.

Alternatively, the sweetener composition of the present invention is preferably a composition containing the glycoside of the present invention in a larger amount than the amount in a wild-type stevia or stevia extract by at least 0.01%. As mentioned above, the glycoside of the present invention was detected for the first time in a cultiver containing abundant Reb.C, and it is not contained in a wild-type stevia or an extract thereof at all or, if any, contained in an amount of the detection limit or less.

The sweetener composition of the present invention may further contain other steviol glycosides. For example, the sweetener composition of the present invention may contain, in addition to the glycoside of the present invention, one or more types of steviol glycosides selected from the group consisting of rebaudioside A, rebaudioside B, rebaudioside C, rebaudioside D, rebaudioside E, rebaudioside F, rebaudioside I, rebaudioside J, rebaudioside K, rebaudioside N, rebaudioside M, rebaudioside O, rebaudioside Q, rebaudioside R, dulcoside A, dulcoside C, rubusoside, steviol, steviol monoside, steviol bioside and stevioside. Herein, "dulcoside C" refers to a compound having the following structure.

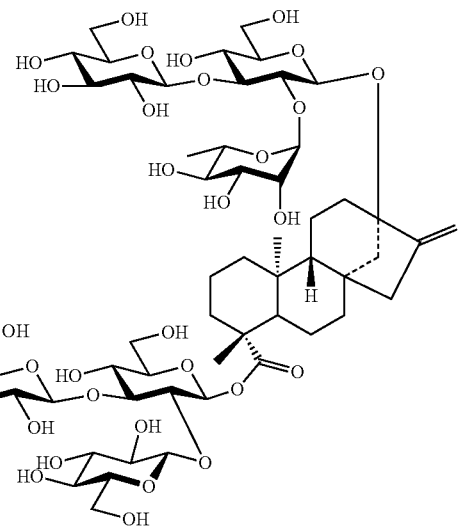

In a case where other steviol glycoside is contained, the composition ratio of the glycoside of the present invention and other steviol glycoside is preferably 0.01:9.99-6:4 in a mass ratio.

The sweetener composition of the present invention may further contain a general sweetener. Examples of such a general sweetener include natural sweeteners such as fructose, sugar, fructose-glucose syrup, glucose, maltose, sucrose, high-fructose syrup, sugar alcohol, oligosaccharide, honey, pressed sugarcane juice (brown sugar syrup), starch syrup, Lo Han Kuo (*Siraitia grosvenorii*) powder, Lo Han Kuo extract, licorice powder, licorice extract, *Thaumatococcus daniellii* seed powder and *Thaumatococcus daniellii* seed extract, and artificial sweeteners such as acesulfame potassium, sucralose, neotame, aspartame and saccharin. Among them, natural sweeteners are preferably used from the aspect of imparting clean taste, easy drinkability, natural flavor and moderately rich taste, where fructose, glucose, maltose, sucrose and sugar are particularly preferably used. Either a single type or a plurality of types of these sweetness ingredients may be used.

3. Food/Beverage Containing Novel Steviol Glycoside

In one aspect of the present invention, a food or beverage containing the compound represented by Formula (1), or a derivative, a salt or a hydrate thereof (hereinafter, also referred to as the "food or beverage of the present invention") is provided. The food or beverage of the present invention is not particularly limited as long as it contains the compound represented by Formula (1), or a derivative, a salt or a hydrate thereof, and it may be a food or beverage containing an extract or a sweetener composition containing the compound represented by Formula (1), or a derivative, a salt or a hydrate thereof. As used herein, a food or beverage refers to foods and beverages. Therefore, in some embodiments, the present invention provides a novel food or beverage, and a method for producing said food or beverage.

While the amount of the glycoside of the present invention contained in the food or beverage of the present invention differs depending on the specific food or beverage, it is preferably around 0.0004%-0.8% and particularly preferably 0.04%-0.4%. As long as the content lies within this range, the lingering aftertaste can advantageously be suppressed.

The food or beverage of the present invention may further contain other steviol glycosides. For example, the sweetener composition of the present invention may contain, in addition to the glycoside of the present invention, one or more types of steviol glycosides selected from the group consisting of rebaudioside A, rebaudioside B, rebaudioside C, rebaudioside D, rebaudioside E, rebaudioside F, rebaudioside I, rebaudioside J, rebaudioside K, rebaudioside N, rebaudioside M, rebaudioside O, rebaudioside Q, rebaudioside R, dulcoside A, dulcoside C, rubusoside, steviol, steviol monoside, steviol bioside and stevioside.

In a case where other steviol glycoside is contained, the composition ratio of the glycoside of the present invention and other steviol glycoside is preferably 0.01:9.99-6:4 in a mass ratio.

The food or beverage of the present invention may further contain a general sweetener. Examples of such a general sweetener include natural sweeteners such as fructose, sugar, fructose-glucose syrup, glucose, maltose, sucrose, high-fructose syrup, sugar alcohol, oligosaccharide, honey, pressed sugarcane juice (brown sugar syrup), starch syrup, Lo Han Kuo (*Siraitia grosvenorii*) powder, Lo Han Kuo extract, licorice powder, licorice extract, *Thaumatococcus daniellii* seed powder and *Thaumatococcus daniellii* seed extract, and artificial sweeteners such as acesulfame potassium, sucralose, neotame, aspartame and saccharin. Among them, natural sweeteners are preferably used from the aspect of imparting clean taste, easy drinkability, natural flavor and moderately rich taste, where fructose, glucose, maltose, sucrose and sugar are particularly preferably used. Either a single type or a plurality of types of these sweetness ingredients may be used.

Examples of the food of the present invention include, but not particularly limited to, a confection, a bread, cereal flour, noodles, rice, a processed agricultural/forestry food, a processed livestock product, a processed fishery product, a milk/dairy product, an oil-and-fat/processed oil-and-fat product, seasoning or other food material.

Examples of the beverage of the present invention include, but not particularly limited to, a carbonated beverage, a non-carbonated beverage, an alcoholic beverage, a non-alcoholic beverage, a beer-taste beverage such as beer or non-alcohol beer, a coffee beverage, a tea beverage, a cocoa beverage, a nutritious beverage and a functional beverage.

The beverage of the present invention may be heat sterilized and packaged to be prepared as a packaged beverage. Examples of such package include, but not particularly limited to, a PET bottle, an aluminum can, a steel can, a paper package, a chilled cup, and a bottle. In a case where heat sterilization is to be performed, the type of heat sterilization is not particularly limited. For example, heat sterilization may be performed by employing a common technique such as UHT sterilization, retort sterilization or the like. While the temperature during the heat sterilization process is not particularly limited, it is, for example, 65-130° C., and preferably 85-120° C., for 10-40 minutes. Sterilization, however, can be carried out at an appropriate temperature for a several seconds, for example, 5-30 seconds, without problem as long as the same sterilizing value as that under the above-described conditions can be earned.

4. Plant Containing Novel Steviol Glycoside and Extract Thereof

In one aspect of the present invention, a plant containing the novel steviol glycoside and an extract thereof are provided. Furthermore, in another aspect of the present invention, a food or beverage, preferably a beverage, containing the plant of the present invention or an extract of said plant is provided. While the amount of the glycoside of the present invention contained in the plant of the present invention is not particularly limited, it is preferably 0.001%-1.000% and more preferably 0.01%-0.80%.

Preferably, the plant of the present invention is a plant that contains the glycoside of the present invention in a larger amount than a wild-type stevia species by 0.01% or more. As described above, the steviol glycoside of the present invention is not contained in a wild-type stevia at all or, if any, contained in an amount of the detection limit or less.

The phrase "contains the glycoside of the present invention in a larger amount than a wild-type stevia species by 0.01% or more" means that, with respect to an amount (concentration) of the glycoside of the present invention contained per unit quantity (e.g., 10 ml) of a liquid extract from fresh leaves (undried leaves) of a wild-type stevia plant, an amount (concentration) of the glycoside of the present invention contained in an equal unit quantity of a liquid extract from fresh leaves (undried leaves) of the plant of the present invention (the same amount as that of the liquid extract from the leaves of the wild-type stevia plant) is higher by 0.01% or more. Here, the plant of the present invention may contain the glycoside of the present invention in a larger amount than a wild-type stevia species by 0.02% or more, 0.03% or more, 0.04% or more, 0.05% or more, 0.07% or more, 0.09% or more, 0.10% or more, 0.15% or more, 0.20% or more, 0.40% or more, 0.60% or more, 0.80% or more, 1.0% or more, 1.50% or more, 2.00% or more, 4.00% or more, 6.00% or more, 8.00% or more, or 10.00% or more.

Moreover, the phrase "the proportion of the glycoside of the present invention among the total steviol glycosides is 0.01% or more" means that the glycoside of the present invention exists at a percentage of 0.01% or more with respect to the content of the total steviol glycosides existing in the liquid extract from the fresh leaves (undried leaves) of the stevia plant of the present invention. Here, the total steviol glycosides neither contain unknown steviol glycosides nor any steviol glycoside existing in an amount less than the detection limit. Preferably, the total steviol glycosides consist of rebaudioside A, rebaudioside B, rebaudioside C, rebaudioside D, rebaudioside E, rebaudioside F, rebaudioside I, rebaudioside J, rebaudioside K, rebaudioside N, rebaudioside M, rebaudioside O, rebaudioside Q, rebaudioside R, dulcoside A, dulcoside C, rubusoside, steviol, steviol monoside, steviol bioside and stevioside.

While the content of the glycoside of the present invention in the plant of the present invention is as described above, in a case where dried leaves are obtained from the plant of the present invention, the glycoside of the present invention may exist in an amount of 0.01 wt % or more, 0.02 wt % or more, 0.03 wt % or more, 0.04 wt % or more, 0.05 wt % or more, 0.07 wt % or more, 0.10 wt % or more, 0.15 wt % or more, 0.20 wt % or more, 0.30 wt % or more, 0.50 wt % or more, 0.60 wt % or more, 0.80 wt % or more, 1.00 wt % or more, 2.00 wt % or more, 4.00 wt % or more, 6.00 wt % or more, 8.00 wt % or more, or 10.00 wt % or more with respect to the weight of said dried leaves.

Here, dried leaves of the plant of the present invention refer to those obtained by drying fresh leaves of the plant of the present invention to reduce their water content to 10 wt % or less, 7 wt % or less, 5 wt % or less, 4 wt % or less, 3 wt % or less, 2 wt % or less, or 1 wt % or less. Preferably, the water content of the dried leaves of the plant of the present invention is 3-4 wt %.

An example of the plant of the present invention include a plant with abundant Reb.C. As described above, the steviol glycoside of the present invention is not contained in a wild-type stevia at all or, if any, contained in an amount of the detection limit or less. Meanwhile, the present inventors found out that the steviol glycoside of the present invention is contained in a larger amount in a plant having abundant Reb.C. Therefore, the novel steviol glycoside and the extract thereof also comprise such a plant with abundant Reb.C and an extract thereof.

An example of such a plant with abundant Reb.C includes, but not particularly limited to a high-rebaudioside C-containing non-recombinant stevia plant which contains rebaudioside C in a larger amount than a wild-type stevia species by 20% or more, and whose proportion of rebaudioside C among the total steviol glycosides is 40% or more (hereinafter, also referred to as a "high-Reb.C plant").

An example of such a high-Reb.C plant include a high-rebaudioside C-containing non-recombinant stevia plant which contains rebaudioside C in a larger amount than a wild-type stevia species by 20% or more, and whose proportion of rebaudioside C among the total steviol glycosides is 40% or more.

A high-Reb.C plant is a cultiver derived from a plant of a wild-type stevia, in which genetic mutation has occurred to increase rebaudioside C. Examples of such genetic mutation include, but not particularly limited to, genetic mutation induced under naturally occurring conditions, genetic mutation induced by a non-recombinational technique and genetic mutation induced by genetic recombination.

A high-Reb.C plant can be screened, for example, by detecting gene polymorphism in the tissue of the plant. Herein, "screening" means to identify and select a high-Reb.C plant among other plant bodies.

The high-Reb.C plant may also be screened according to a screening method that includes a step of identifying a polymorphism of A in the wild type being altered to T at the 60th nucleotide of the nucleotide sequence represented by SEQ ID NO:11 in the genome of a test plant, The plant of the present invention not only comprises the whole plant but may also comprise plant organs (for example, leaf, petal, stem, root, seed, etc.), plant tissues (for example, epidermis, phloem, parenchyma, xylem, vascular bundles, palisade tissue, spongy tissue, etc.), various forms of plant cells (for example, suspension cultured cells), a protoplast, a leaf piece, callus and the like.

In addition, the plant of the present invention may also comprise a tissue culture or a plant cell culture. This is because such a tissue culture or plant cell culture may be cultured to regenerate a plant. Examples of the tissue culture or the plant cell culture of the plant of the present invention include, but not limited to, an embryo, meristematic cells, pollen, a leaf, a root, a root apex, a petal, a protoplast, a leaf piece and callus.

An extract of the plant of the present invention can be obtained by reacting a fresh or dried leaf of the plant of the present invention with an appropriate solvent (an aqueous solvent such as water or an organic solvent such as alcohol, ether or acetone). For extraction conditions, see the method described in WO2016/090460 or a method described in the example below.

Preferably, the extract of the plant of the present invention contains the glycoside of the present invention in a larger amount than a wild-type stevia by 0.01% or more, where the proportion of the glycoside of the present invention among the total steviol glycosides is 0.01% or more. Here, the phrase "contains the glycoside of the present invention in a larger amount than a wild-type stevia by 0.01% or more" means the same as described above. Similarly, the phrase the "proportion of the glycoside of the present invention among the total steviol glycosides is 0.01% or more" also means the same as described above.

5. Flavor Controlling Agent Containing Novel Steviol Glycoside

Although the novel steviol glycoside of the present invention is contained in a stevia extract in a minute quantity, it is considered to have an influence on the flavor the stevia extract. While not wishing to be bound by any theory, addition of a small amount of the steviol glycoside of the present invention is presumably capable of controlling the flavor of a food or beverage. Therefore, in one aspect of the present invention, a flavor controlling agent containing the above-described compound represented by Formula (1) or a derivative, a salt or a hydrate thereof is provided.

As used herein, a "flavor controlling agent" refers to a substance that can be added to a food or beverage to control the flavor of the food or beverage. Preferably, the flavor controlling agent of the present invention can be added to a food or beverage so as to control the flavor of the food or beverage itself without the consumers recognizing the taste of the flavor controlling agent itself. For example, since the steviol glycoside of the present invention has good sweet lingering as compared to conventional steviol glycosides, it can be used as a flavor controlling agent for controlling the sweet lingering of the food or beverage.

The flavor controlling agent of the present invention preferably contains, in addition to the above-described compound represented by Formula (1) or a derivative, a salt or a hydrate thereof, one or more types of other sweeteners, Examples of such sweetener include: one or more types of steviol glycosides selected from the group consisting of rebaudioside A, rebaudioside B, rebaudioside C, rebaudioside D, rebaudioside rebaudioside F, rebaudioside 1, rebaudioside J, rebaudioside K, rebaudioside N, rebaudioside M, rebaudioside 0, rebaudioside Q, rebaudioside R, dulcoside A, dulcoside C, rubusoside, steviol, steviol monoside, steviol bioside and stevioside; natural sweeteners such as fructose, sugar, fructose-glucose syrup, glucose, maltose, sucrose, high-fructose syrup, sugar alcohol, oligosaccharide, honey, pressed sugarcane juice (brown sugar syrup), starch syrup, Lo Han Kuo (*Siraitia grosvenorii*) powder, a Lo Han Kuo extract, licorice powder, a licorice extract, *Thaumatococcus daniellii* seed powder and a *Thaumatococcus daniellii* seed extract; and artificial sweeteners such as acesulfame potassium, sucralose, neotame, aspartame and saccharin.

6. Method for Producing Novel Steviol Glycoside

As described above, the steviol glycoside of the present invention can be produced by (A) isolation/purification from a plant, (B) a chemical synthesis, or (C) a biosynthesis. Hereinafter, each of them will be described.

(A) Isolation/Purification from Plant

Since the plant of the present invention contains the novel steviol glycoside of the present invention, the novel steviol glycoside can be isolated/purified from said plant. A fresh or dried leaf of the plant of the present invention is allowed to react with an appropriate solvent (an aqueous solvent such as water or an organic solvent such as alcohol, ether or acetone) to extract the novel steviol glycoside in a liquid extract state. For extraction conditions and else, see the method described in WO2016/090460 or the method described in the example below.

Furthermore, the resulting liquid extract may be subjected to a known method such as a gradient of ethyl acetate or other organic solvent: water, high performance liquid chromatography (HPLC), or ultra (high) performance liquid chromatography (UPLC) to isolate/purify the novel steviol glycoside.

The content of the novel steviol glycoside in the plant can be determined by the method described in WO2016/090460 or the method described in the example below. Specifically, the content can be measured by sampling fresh leaves from the plant of the present invention and subjecting the leaves to LC-MS/MS.

(B) Chemical Synthesis

A method for producing the steviol glycoside of the present invention through chemical synthesis will be described in detail hereinbelow.

Steviol glycosides have structures in which different sugar moieties (glucose, rhamnose, xylose, etc.) are attached to the aglycone, i.e., steviol, via various linkage forms (linkage positions and conformations). Therefore, a steviol glycoside of interest can be obtained via various synthetic pathways depending on the selected starting material. Those skilled in the art to which the present invention pertains, however, would understand that the time and the yield for obtaining the compound of interest greatly vary depending on the synthetic pathways.

This time, the present inventors found out a novel method for producing a steviol glycoside of the present invention with higher selectivity and higher yield via a specific synthetic pathway. According to the method for producing the steviol glycoside of the present invention, a chemical synthesis of the steviol glycoside proceeds by separating the steviol glycoside into a "steviol glycoside" and a "sugar hemiacetal" as shown in Scheme 1.

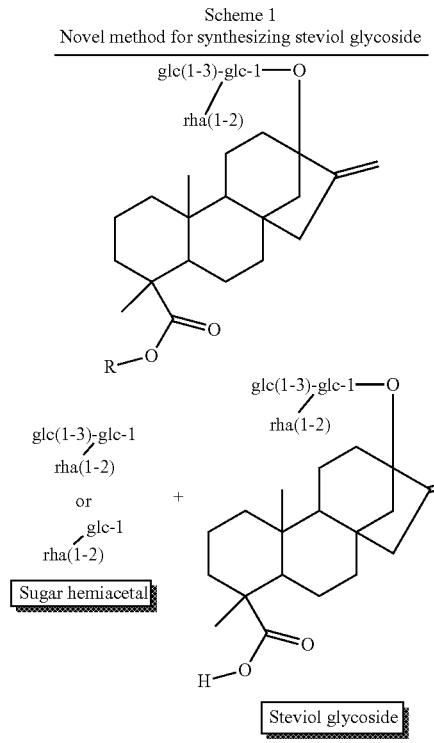

The steviol glycoside can be prepared by deriving from an existing natural substance (rebaudioside, dulcoside, stevioside, steviol bioside, rubusoside, etc. Meanwhile, the sugar hemiacetal can be prepared either from an existing natural substance or by a chemical synthesis. The present inventors found that the steviol glycoside of interest can be obtained with good yield and extremely high β-selectivity by condensing the steviol glycoside and the sugar hemiacetal through the Mitsunobu reaction.

In one aspect of the present invention, a method for producing the compound represented by Formula (1) is provided where the method comprises the steps of:

(A) preparing Intermediate 1 represented by Formula (5):

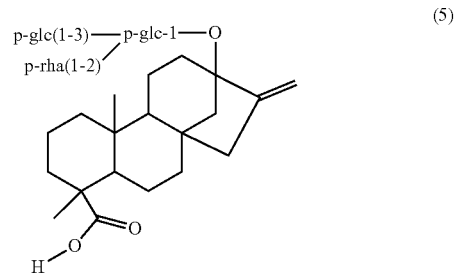

(5)

wherein p-glc represents glucose in which at least one hydroxyl group is protected by a protecting group, and p-rha represents rhamnose in which at least one hydroxyl group is protected by a protecting group, from rebaudioside C represented by Formula (4):

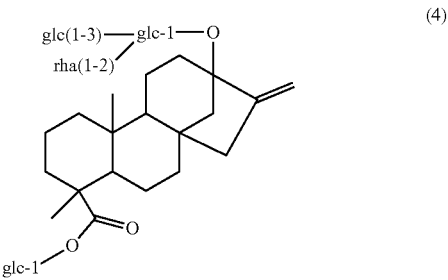

(4)

wherein glc represents glucose and rha represents rhamnose;

(B) preparing Intermediate 2 represented by Formula (6) or Intermediate 3 represented by Formula (7) from a glucopyranoside derivative:

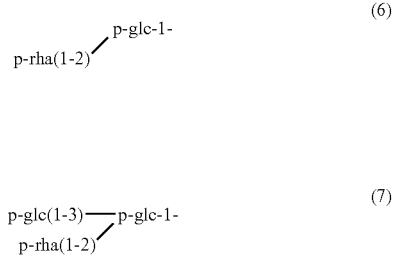

(6)

(7)

wherein p-glc represents glucose in which at least one hydroxyl group is protected by a protecting group, and p-rha represents rhamnose in which at least one hydroxyl group is protected by a protecting group; and (C) allowing Intermediate 1 to react with Intermediate 2 or 3 in the presence of a phosphine reagent and an azo compound to obtain Intermediate 4 represented by Formula (8):

(8)

wherein, $R_1$ represents a sugar chain of Formula 9 or (10); and (9)

(10)

p-glc represents glucose in which at least one hydroxyl group is protected by a protecting group, and p-rha represents rhamnose in which at least one hydroxyl group is protected by a protecting group.

Herein, examples of the protecting group include an acyl protecting group, a trisubstituted silyl group, an acetal protecting group and an ether protecting group. Preferable examples include a trisubstituted silyl group (a trimethylsilyl group, a triethylsilyl group, a t-butyldimethylsilyl group, etc.) and an acyl protecting group (an acetyl group, a benzoyl group, etc.).

Hereinafter, one specific aspect of the method for producing the steviol glycoside of the present invention will be described, but the method for producing the glycoside of the present invention should not be limited to this aspect.

(A) First Step (Synthesis of Steviol Glycoside)

A steviol glycoside can be obtained, for example, by following Scheme 2 below using naturally occurring rebaudioside C (dulcoside B) as a starting material.

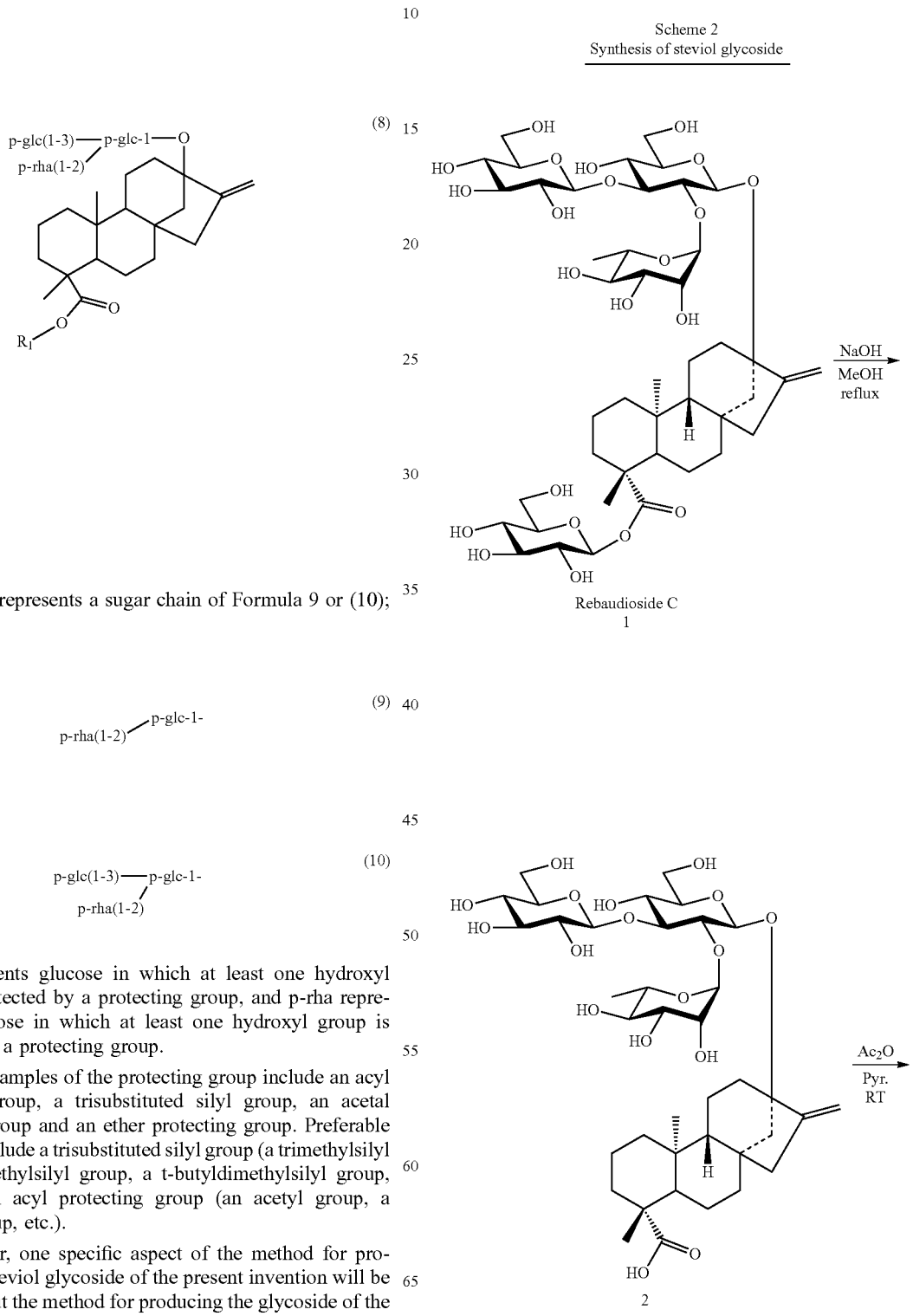

Scheme 2
Synthesis of steviol glycoside

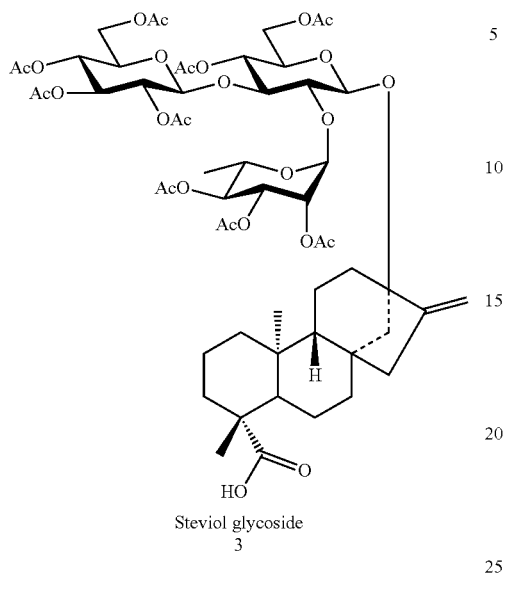

First, rebaudioside C is dissolved in a solvent such as methanol and water, added with a strong base such as sodium hydroxide, and refluxed at 60° C.-120° C. for 2 hours or longer so that the glucose molecule is removed from C-19 of rebaudioside C to give Compound 2 above. In doing so, the solvent may be evaporated after neutralizing the reaction solution with a cation exchange resin or the like.

Compound 2 is further dissolved in a solvent such as pyridine, and added with acetic anhydride or the like to protect the hydroxyl groups contained in Compound 2, thereby obtaining Compound 3 (Intermediate 1).

(B) Second Step (Synthesis of Disaccharide or Trisaccharide Hemiacetal)

A disaccharide hemiacetal or a trisaccharide hemiacetal can be obtained, for example, by using a commercially available glucopyranoside derivative as a starting material. Syntheses of a disaccharide hemiacetal (Step 2a) and a trisaccharide hemiacetal (Step 2b) are shown in Schemes 3 and 4, respectively.

Scheme 3 showing synthesis of a disaccharide hemiacetal (Step 2a) is as follows.

First, 4-methoxyphenyl 3-O-benzyl-4,6-O-benzylidine-β-D-glucopyranoside (Compound 4), Compound 5 and molecular sieves (MS) are dissolved in a solvent such as dichloromethane, added with trifluoromethanesulfonic acid (acid catalyst), and agitated at 25° C.-80° C. for 2 hours or longer to give Compound 6.

Subsequently, Compound 6 is dissolved in a solvent such as ethanol or THF, added with a catalyst such as palladium hydroxide at room temperature, and agitated in an hydrogen atmosphere at room temperature for 2 hours or longer to complete the reaction. Then, the catalyst is removed, by filtration to give Compound 7. Compound 7 is dissolved in a solvent such as pyridine, added with acetic anhydride at room temperature, and agitated at room temperature for 12-36 hours. Thereafter, the solution is concentrated under a reduced pressure, added with acetonitrile and water, added with an oxidant such as cerium ammonium nitrate, and agitated for 5 minutes to 2 hours to give Compound 8 (Intermediate 2).

Scheme 4 showing synthesis of a trisaccharide hemiacetal (Step 2b) is as follows.

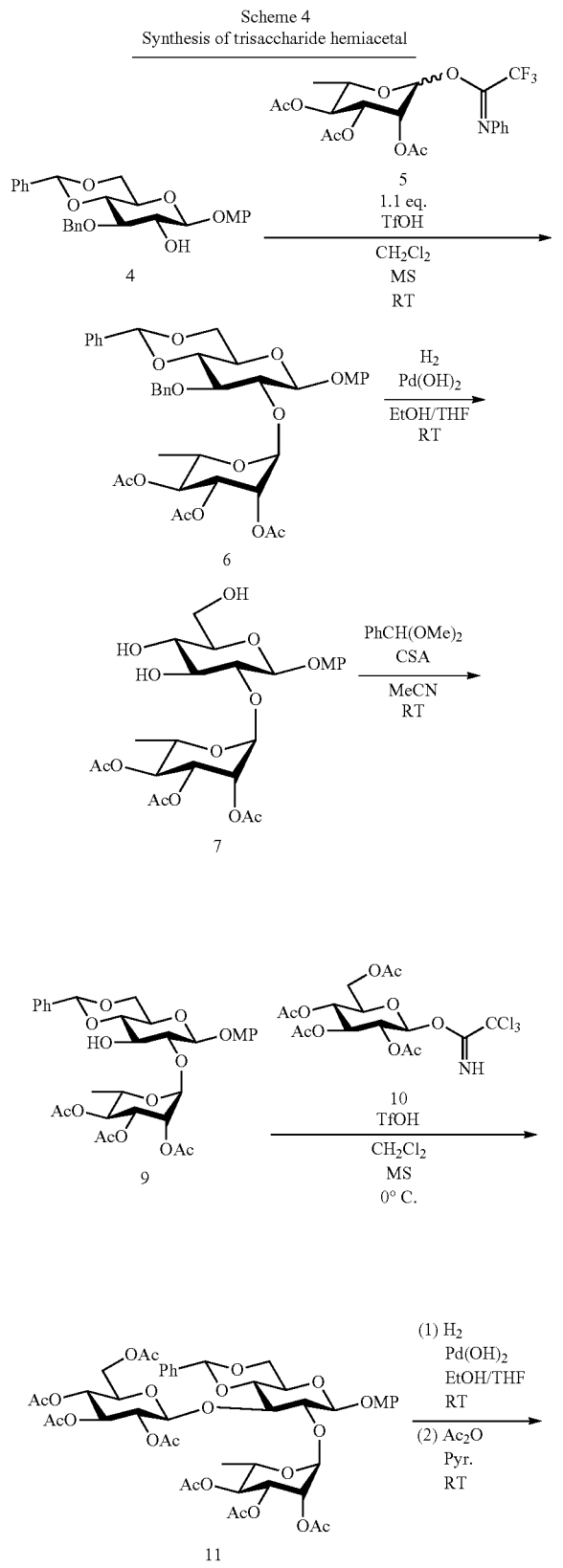

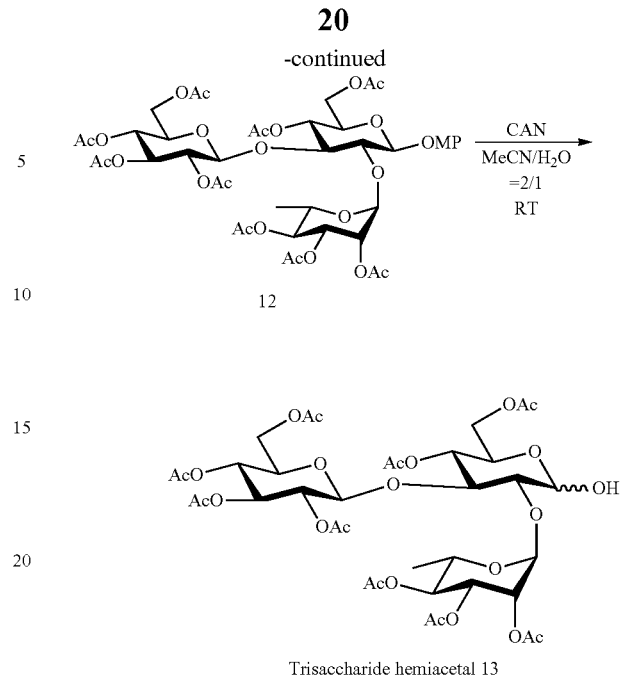

Trisaccharide hemiacetal 13

First, 4-methoxyphenyl 3-O-benzyl-4,6-O-benzylidine-β-D-glucopyranoside (Compound 4), Compound 5 and molecular sieves (MS) are dissolved in a solvent such as dichloromethane, added with trifluoromethanesulfonic acid (acid catalyst), and agitated at 25° C.-80° C. for 2 hours or longer to give Compound 6.

Subsequently, Compound 6 is dissolved in a solvent such as ethanol or THF, added with a catalyst such as palladium hydroxide at room temperature, and agitated in an hydrogen atmosphere at room temperature for 2 hours or longer to complete the reaction. Then, the catalyst is removed by filtration to give Compound 7. Compound 7 is dissolved in acetonitrile, added with benzaldehyde dimethyl acetal at room temperature, and agitated for 2 hours or longer to give Compound 9.

Compounds 9 and 10 and molecular sieves (MS) are dissolved in a solvent such as dichloromethane, added with trifluoromethanesulfonic acid at room temperature, and agitated at 0° C. for 3-9 hours to give Compound 11. The resulting Compound 11 is dissolved in a solvent such as ethanol or THF, added with a catalyst such as palladium hydroxide at room temperature, and agitated in an hydrogen atmosphere at room temperature for 2 hours or longer to complete the reaction. Then, the resultant dissolved in a solvent such as pyridine, added with acetic anhydride at room temperature, and agitated at room temperature for 12-36 hours to give Compound 12. Thereafter, the solution is concentrated under a reduced pressure, added with acetonitrile and water, added with an oxidant such as cerium ammonium nitrate, and agitated for 5 minutes to 2 hours, thereby obtaining Compound 13 (Intermediate 3).

(C) Third Step (Synthesis of Compound Represented by Formula (1))

The compound represented by Formula (1) can be synthesized, for example, by following Scheme 5 or 6 below using Compound 3 (Intermediate 1) and Compound 8 or 13 (Intermediate 2 or 3) obtained in Steps 1 and 2 (2a or 2b) above.

Scheme 5
Synthesis of compound represented by Formula (1)
(Glycoside A)
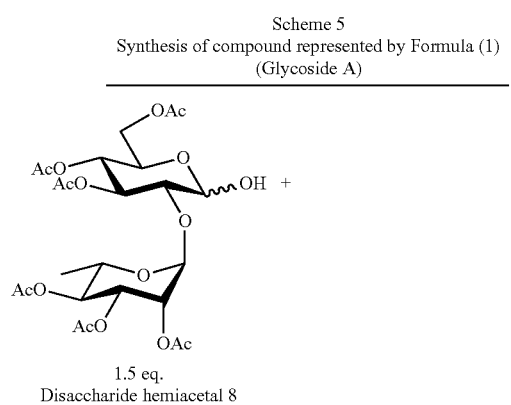
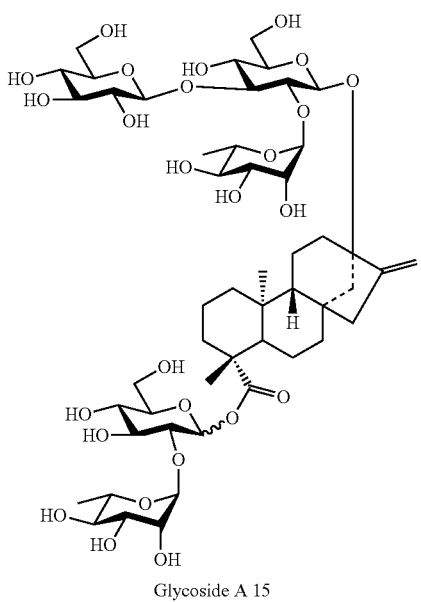
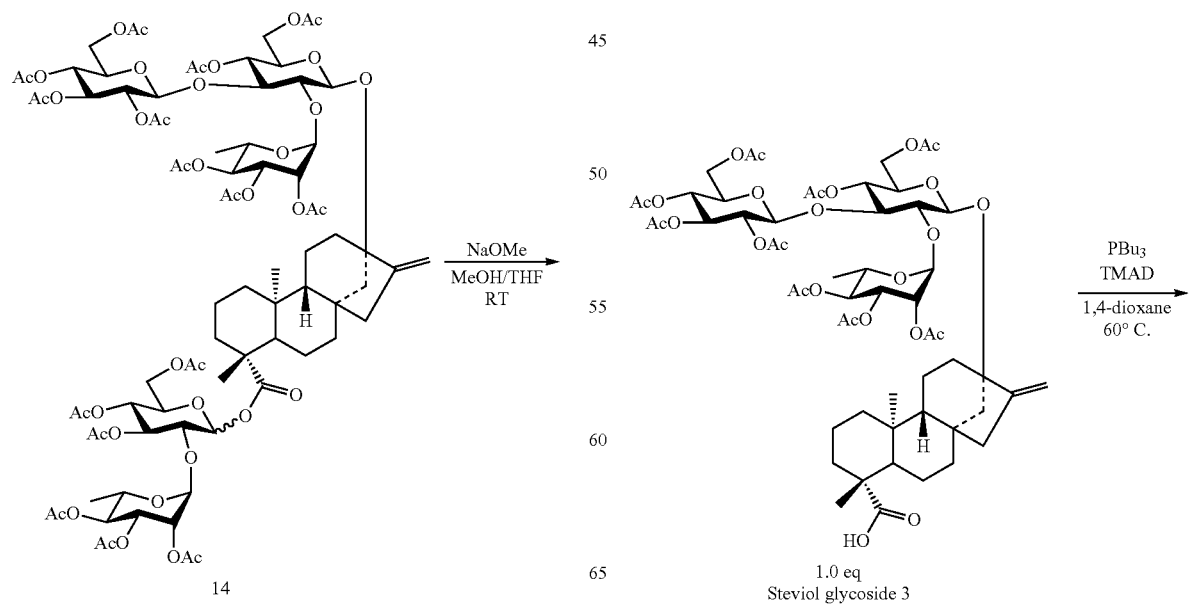

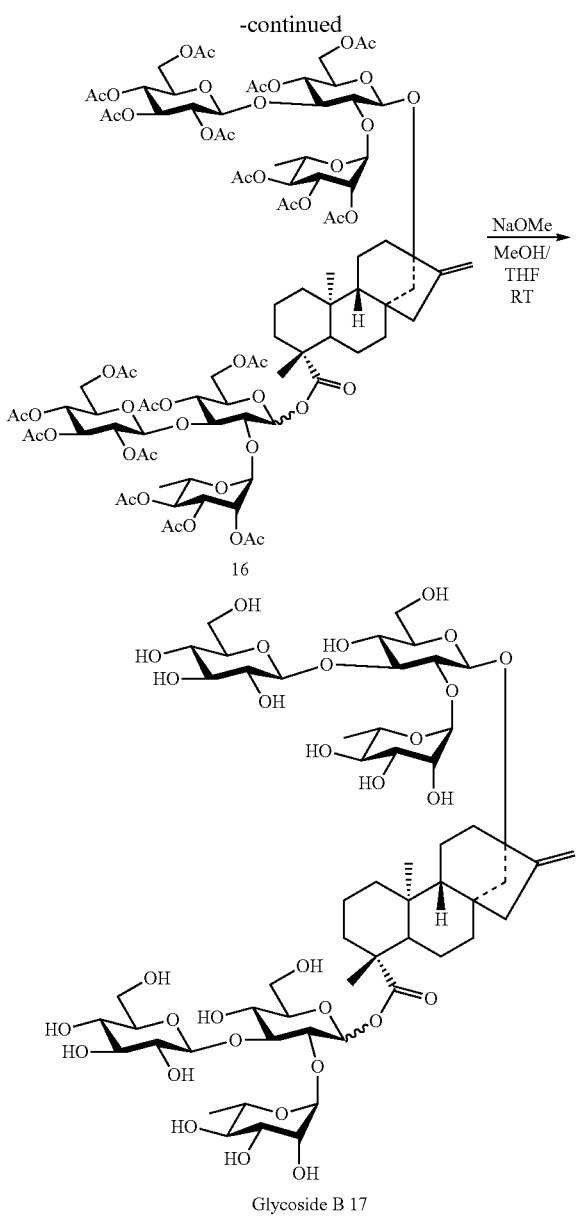

Glycoside B 17

First, the disaccharide or trisaccharide hemiacetal and the Steviol glycoside obtained in Steps 1 and 2 (2a or 2b) are allowed to undergo the Mitsunobu reaction so as to obtain a glycoside in which the disaccharide or trisaccharide hemiacetal is selectively attached to the carboxylic group at C-19 of steviol. Specifically, these compounds are dissolved in 1,4-dioxane, added with a phosphine reagent such as tributylphosphine or triphenylphosphine and an azo compound such as 1,1'-azobis (N,N'-dimethylformamide) (TMAD) at room temperature, and agitated at 50° C.-80° C. for 2 hours or longer to give Compound 14 or 16. Finally, the protecting groups of Compound 14 or 16 are deprotected to give the compound represented by Formula (1) (Glycoside A. or B).

(3) Biosynthesis
(C) Biosynthesis

The steviol glycoside of the present invention can also be generated by transferring a polynucleotide coding for a predetermined protein into a host cell derived from a bacterium, a plant, an insect, a non-human mammal or the like, and using steviol, a steviol glycoside, UDP-glucose and/or DP-rhamnose as a substrate. Steviol, a steviol glycoside, UDP-glucose or UDP-rhamnose as the substrate may be either provided or biosynthesized in the cell. While examples of the predetermined protein include stevia-derived UGT85C2 (whose amino acid sequence is represented by SEQ ID NO:2), UGT74G1 (whose amino acid sequence is represented by SEQ ID NO:4), UGT91D2 (whose amino acid sequence is represented by SEQ ID NO:6), UGT76G1 (whose amino acid sequence is represented by SEQ ID NO:8) and *Arabidopsis thaliana*-derived UDP-rhamnose synthase AtRHM2 (whose amino acid sequence is represented by SEQ ID NO: 0), it is not limited thereto as long as it has an equivalent activity.

The above-described protein is an enzyme derived from *Arabidopsis thaliana* or stevia, which is expected to be highly active in an environment outside plant cells such as *Arabidopsis thaliana* and stevia (for example, in an extracellular environment, or inside a host cell other than stevia). In this case, the polynucleotide coding for the above-described protein (for example, UGT85C2 gene is represented by SEQ ID NO:1, UGT74G1 gene is represented by SEQ ID NO:3, UGT91D2 gene is represented by SEQ ID NO:5, UGT76G1 gene is represented by SEQ ID NO:7 and AtRHM2 gene is represented by SEQ ID NO:9) is transferred into a host cell derived from a bacterium, a fungus, a plant, an insect or a non-human mammal so as to allow expression of the protein of the present invention, to which steviol, a steviol glycoside, UDP-glucose or UDP-rhamnose as the substrate is provided to generate the compound of the present invention. Alternatively, depending in the host, the above-described protein is expressed in the host cell, to which an appropriate substrate is provided to generate the compound of the present invention.

In one aspect of the present invention, a method for producing the novel steviol glycoside of the present invention is provided, where the method is characterized by use of a non-human transformant that has been introduced with at least one of polynucleotides (a) to (g).

(a) A polynucleotide coding for a protein that has 90% or higher identity with the amino acid sequence of SEQ ID NO:2 and that has an activity of adding glucose to the hydroxyl group at C-13 of the steviol glycoside.

(b) A polynucleotide coding for a protein that has 90% or higher identity with the amino acid sequence of SEQ ID NO:4 and that has an activity of adding glucose to the carboxylic acid at C-19 of the steviol glycoside.

(c) A polynucleotide coding for a protein that has 90% or higher identity with the amino acid sequence of SEQ ID NO:6 and that has an activity of adding rhamnose to glucose attached to C-13 of the steviol glycoside via a 1→2 linkage.

(d) A polynucleotide coding for a protein that has 90% or higher identity with the amino acid sequence of SEQ ID NO:8 and that has an activity of adding glucose to C-3 of glucose at C-13 of the steviol glycoside via a 1→3 linkage.

(e) A polynucleotide coding for a protein that has 90% or higher identity with the amino acid sequence of SEQ ID NO:6 and that has an activity of adding glucose to glucose at C-19 of the steviol glycoside via a 1→2 linkage.

(f) A polynucleotide coding for a protein that has 90% or higher identity with the amino acid sequence of SEQ ID NO:8 and that has an activity of adding glucose to glucose at C-19 of the steviol glycoside via a 1→3 linkage.

(g) A polynucleotide coding for a protein that has 90% or higher identity with the amino acid sequence of SEQ ID NO:1.0 and that has an activity of generating UDP-rhamnose from UDP-glucose.

In a preferable aspect of the present invention, polynucleotides independently having 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher sequence identity with the nucleotide sequences of the sequence numbers mentioned in (a) to (g) above can be used.

In another preferable aspect of the present invention, proteins that independently have an amino acid sequence having 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher sequence identity with the amino acid sequences of the sequence number mentioned in (a) to (g) above and that has the predetermined activity described in (a) to (g) above can be used, Preferably, a polynucleotide coding for the above-described protein is introduced into a host while being inserted into an appropriate expression vector. The polynucleotides may individually be inserted into separate vectors.

An appropriate expression vector is generally made to contain:
(i) a promoter that allows transcription in the host cell
(ii) a polynucleotide of the present invention linked to said promoter; and
(iii) an expression cassette that is involved in transcription termination and polyadenylation of RNA molecules and that contains, as a component thereof, a signal that functions in the host cell.

Examples of a method for preparing an expression vector include, but not particularly limited to, a method that uses a plasmid, a phage, a cosmid or the like, and DNA molecules having necessary components.

The specific type of the vector is not particularly limited, and any vector that allows expression in the host cell can suitably be selected. Specifically, a promoter sequence is suitably selected according to the type of the host cell to ensure expression of the polynucleotide of the present invention, and a vector obtained by integrating this promoter sequence and the polynucleotide of the present invention into a plasmid or the like is used as an expression vector.

The expression vector of the present invention includes expression controlling regions (for example, a promoter, a terminator and/or an origin of replication and the like) depending on the type of the host into which it is introduced. A promoter used in a bacterial expression vector may be a common promoter (for example, a trc promoter, a tac promoter, a lac promoter, etc.), a promoter used for a yeast may be, for example, a glyceraldehyde-3-phosphate dehydrogenase promoter, a PH05 promoter, a GAL1/10 promoter or the like, and a promoter for filamentous fungi may be, for example, amylase, trpC or the like. Moreover, examples of a promoter for expressing the gene of interest in a plant cell include a cauliflower mosaic virus 35S RNA promoter, a rd29A gene promoter, a rbcS promoter, and a mac-1 promoter in which the enhancer sequence of the cauliflower mosaic virus 35S RNA promoter is provided at the 5' end of a promoter sequence of Agrobacterium-derived mannopine synthase. A promoter for an animal cell host may be a viral promoter (for example, a SV40 early promoter, a SV40 late promoter, etc.). Examples of a promoter that is inducibly activated in response to external stimuli include a mouse mammary tumor virus (MMTV) promoter, a tetracycline responsive promoter, a metallothionein promoter and a heat shock protein promoter.

Preferably, the expression vector contains at least one selectable marker. As such a marker, an auxotrophic marker (LEU2, URA3, HIS3, TRP1, ura5, niaD), a drug resistance marker (hygromycin, zeocin), a geneticin resistance gene (G418r), a copper resistance gene (CUP1) (Marin et al., Proc. Natl. Acad., Sci. USA. vol. 81, p. 337, 1984), a cerulenin resistance gene (fas2m, PDR4) (Junji Inokoshi et al., Journal of Japanese Biochemical Society, vol. 64, p. 660, 1992; Hussain et al., Gene, vol. 101, p. 149, 1991, respectively) or the like can be used.

As a method for transforming a host cell, a generally employed known method can be employed. For example, an electroporation method (Mackenxie, D. A. et al., Appl. Environ. Microbiol., vol. 66, p. 4655-4661, 2000), a particle delivery method (Japanese Unexamined Patent Application Publication No. 2005-287403), a spheroplast method (Proc. Natl. Acad. Sci. USA, vol. 75, p. 1929, 1978), a lithium acetate method (J. Bacteriology, vol. 153, p. 163, 1983), a method described in Methods in yeast genetics, 2000 Edition: A Cold Spring Harbor Laboratory Course Manual, or the like can be performed although the present invention is not limited thereto.

In addition, as to general molecular biological processes, see "Sambrook and Russell, Molecular Cloning: A Laboratory Manual Vol. 3, Cold Spring Harbor Laboratory Press 2001", "Methods in Yeast Genetics, A laboratory manual (Cold Spring Harbor Laboratory Press, Cold Spring Harbor, NY)" and the like.

A non-human transformant obtained as described above can be cultured so as to allow the non-human transformant to produce a steviol glycoside. Such a non-human transformant is preferably a yeast. Moreover, the non-human transformant is preferably cultured in a medium containing steviol. The accumulated steviol glycoside can be extracted/purified to obtain the steviol glycoside of the present invention.

EXAMPLES

[Isolation of Novel Steviol Glycoside]

Extracts obtained from the leaves of four lines of novel stevia plant bodies (Sample 1 (EM3-4), Sample 2 (EM2-27-8), Sample 3 (EM2-27-15) and Sample 4 (EM2-II)) developed at Suntory Global Innovation Center (SIC) were subjected to high performance liquid chromatography (HPLC) separation-mass spectrometry (MS) for the screening analysis of the steviol glycosides contained in the stevia plant bodies based on the molecular weights of steviol glycosides that had a sugar chain formed of D-glucopyranosyl (Glc), L-rhamnopyranosyl (Rha) and xylopyranosyl (Xyl). Here, Sample 1 is a high-Reb.C plant having a genome polymorphism of A in the wild type being altered to T at the 60th nucleotide of the nucleotide sequence represented by SEQ ID NO:11 in the genome. A statistical analysis of the correlation between the phenotype having a high-Reb.C concentration and the polymorphism of SEQ ID NO:11 revealed that said polymorphism had a statistic correlation with the phenotype having a high-Reb.C concentration.

A process for preparing a test liquid was as follows: 10.0 mg each of lyophilized dried stevia leaves was weighed into a glass vial, to which 1.0 mL of water/methanol (1/1 vol/vol) was added as an extracting solvent, and then the resultant was subjected to ultrasonic irradiation in an ultrasonic cleaner (AS ONE, AS52GTU) at a set temperature of 25° C. for 20 minutes, thereby obtaining a liquid extract of a steviol glycoside from the stevia leaves. The resultant was further 10-fold diluted with water/methanol and filtrated through a filter with a pore size of 0.45 μm (Nacalai tesque, Cosmonice filter S (solvent)) before being subjected to HPLC-MS.

For the HPLC part of HPLC-MS, Nexera LC-30AD (Shimadzu Corporation) was used as a liquid delivery unit LC pump, and SM-C18 (4.6×250 mm) (from Imtakt) as a separation column. Liquid delivery of the LC mobile phase was carried out by using 0.2% acetic acid-containing Milli-Q water as mobile phase A and methanol as mobile phase B, where the binary gradient was such that the concentration of the mobile phase B was constantly maintained at 10% during 0-5 minutes, shifted from 10% to 70% in the next 15 minutes, and then shifted from 70% to 100% in the following 5 minutes, and the gradient was finally ended by maintaining the concentration of the mobile phase B at 100% for 5 minutes. The flow rate of the mobile phase was 0.4 mL/min, and the stevia leaf liquid extract that had been diluted and filtrated with a filter was injected for 5 μL.

For the MS part, triple quadrupole mass spectrometer LCMS-8030 (Shimadzu Corporation) equipped with an electrospray ionization (ESI) ion source was used. The mass spectrometry measurement was carried out in a selected ion monitoring (SIM) mode by selecting the negative ion measurement mode and the m/z values. The m/z values were selected by calculation based on the molecular weights of the steviol glycosides that had sugar chains formed of D-glucopyranosyl (Glc), L-rhamnopyranosyl (Rha) and xylopyranosyl (Xyl). Accordingly, m/z=641.2 (Glc (2)), 773.2 (Glc (2), Xyl (1)), 787.2 (Glc (2), Rha (1)), 803.2 (Glc (3)), 935.3 (Glc (3), Xyl (1)), 949.3 (Glc (3), Rha (1)), 965.3 (Glc (4)), 1095.4 (Glc (3), Rha (2)), 1097.4 (Glc (4), Xyl (1)), 1111.4 (Glc (4), Rha (1)), 1127.4 (Glc (5)), 1257.5 (Glc (4), Rha (2)), 1259.5 (Glc (5), Xyl (1)), 1273.5 (Glc (5), Rha (1)), 1289.5 (Glc (6)), 1435.6 (Glc (6), Rha (1)) were selected. Furthermore, a high purity reagent, rebaudiosides A, B, D, F, M, N and O, stevioside, and dulcosides A and B available were also measured under the same conditions so as to confirm the negative ion m/z values and the retention time in HPLC. The peak areas (arbitrary unit) of the mainly detected steviol glycosides are shown in Table 1.

chromatogram of the steviol glycoside (m/z 1257.5) in which the modified sugar chain contained four glucose moieties (Glc) and two rhamnose moieties (Rha). Specifically, the peak at Rt 28.50 minutes shown in FIG. 3 was a unknown substance. For Sample 4 whose rebaudioside C content was lower than the content of rebaudioside A and whose sugar chain elongation was shorter than other samples, the peak value at Rt 28.50 minutes was lower than the detection limit.

[Structural Analysis of Novel Steviol Glycoside]

According to the present invention, structural analyses of Novel steviol glycosides 1 and 2 detected in a cultiver with high rebaudioside C content were performed according to the following procedure.

(i) Structural deduction by a fragmentation analysis through high performance liquid chromatography (HPLC)-high resolution mass spectrometry (MS), MS/MS, and three-stage ion fragmentation ($MS^3$ fragmentation).

(ii) Chemical synthesis of the deduced steviol glycoside standard products via chemical reaction.

(iii) Structural confirmation by matching with the chemically synthesized standard products with respect to the retention time and the fragmented pattern from HPLC-high resolution MS and $MS^3$ fragmentation Hereinafter, each of Steps (i)-(iii) above will be described in detail.

(i) Structural deduction by a fragmentation analysis through high performance liquid chromatography (HPLC)-high resolution mass spectrometry (MS), MS/MS, and three-stage ion fragmentation ($MS^3$ fragmentation)

A process for preparing test liquids were as follows: 10.0 mg each of lyophilized dried stevia leaves was weighed into a glass vial, to which 1.0 mL of water/methanol (1/1 vol/vol) was added as an extracting solvent, and then the resultant was subjected to ultrasonic irradiation in an ultrasonic cleaner (AS ONE, AS52GTU) at a set temperature of 25° C. for 20 minutes, thereby obtaining a liquid extract of a steviol

TABLE 1

Peak areas (arbitrary unit) observed by STM measurement in HPLC-MS

| Compound name | Rebaudioside A | Rebaudioside C | Rebaudioside D | Rebaudioside M | Dulcoside C | Novel steviol glycoside 1 m/z 1095.4 | Novel steviol glycoside 2 m/z 1257.5 | Rebaudioside N |
|---|---|---|---|---|---|---|---|---|
| Retention time (min) | 29.60 | 29.96 | 28.00 | 28.66 | 27.70 | 28.73 | 28.50 | 28.18 |
| Peak area (Sample 1) | 29,669,582 | 30,122,062 | 1,428,384 | 1,030,603 | 140,947 | 76,369 | 242,070 | 772,570 |
|  | 46.92% | 47.63% | 2.26% | 1.63% | 0.22% | 0.12% | 0.38% | 1.22% |
| Peak area (Sample 2) | 23,762,676 | 24,201,473 | 2,253,735 | 1,029,837 | 97,388 | 94,330 | 292,157 | 1,211,504 |
|  | 45.13% | 45.97% | 4.28% | 1.96% | 0.18% | 0.18% | 0.55% | 2.30% |
| Peak area (Sample 3) | 15,386,726 | 5,872,656 | 3,585,775 | 3,296,579 | 89,988 | 0 | 86.845 | 896.549 |
|  | 52.82% | 20.16% | 12.31% | 11.32% | 0.31% | 0.00% | 0.30% | 3.08% |
| Peak area (Sample 4) | 16,070,017 | 10,339,094 | 1,404,429 | 74,413 | 0 | 17,634 | 0 | 308,709 |
|  | 56.96% | 36.64% | 4.98% | 0.26% | 0.00% | 0.06% | 0.00% | 1.09% |

Figure 2:
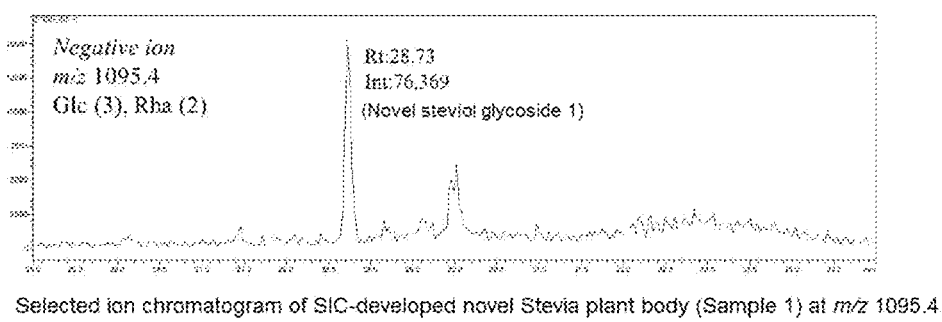
FIG. 2 illustrates a diagram showing a selected ion chromatogram of Sample 1 at m/z of 1095.4.

FIG. 2 shows a selected ion chromatogram of Sample 1 (EM3-4) at m/z of 1095.4. A peak of a molecular weight that had never been reported was observed in the selected ion chromatogram of the steviol glycoside (m/z 1095.4) in which the modified sugar chain contained three glucose moieties (Glc) and two rhamnose moieties (Rha). Specifically, the peak at Rt 28.73 minutes shown in FIG. 2 was a unknown substance.

For Sample 3 whose rebaudioside C content was lower than the content of rebaudioside A and whose sugar chain elongation was shorter than other samples, the peak value at Rt 28.73 minutes was lower than the detection limit.

Figure 3:
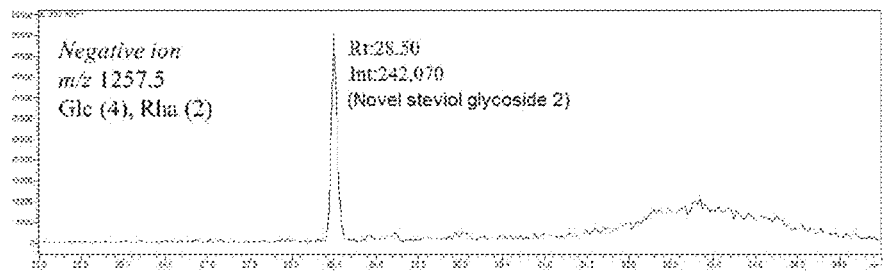
FIG. 3 illustrates a diagram showing a selected ion chromatogram of Sample 1 at m/z of 1257.5.

FIG. 3 shows a selected ion chromatogram of Sample 1 (EM3-4) at m/z of 1257.5. A peak of a molecular weight that had never been reported was observed in the selected ion glycoside from the stevia leaves. The resultant was further 10-fold diluted with water/methanol and filtrated through a filter with a pore size of 0.45 μm (Nacalai tesque, Cosmonice filter S (solvent)) before being subjected to HPLC-MS.

In an equipment configuration for high performance liquid chromatography-electrospray ionization-high resolution mass spectrometry (HPLC-ESI-HRMS), equipment for HPLC was configured by using Prominence LC-20AD (Shimadzu Corporation) as a liquid delivery unit LC pump and SM-C18 (4.6×250 mm) (from Imtakt) as a separation column. The LC mobile phase was delivered using 0.2% acetic acid-containing Milli-Q water as mobile phase A and methanol as mobile phase B, where the binary gradient was such that the concentration of the mobile phase B was constantly maintained at 10% during 0-5 minutes, shifted from 10% to 70% in the next 15 minutes, and further shifted from 70% to 100% in the following 5 minutes. Finally, the concentration of the mobile phase B was maintained at 100% for 5 minutes to end. The flow rate of the mobile phase was 0.4 mL/min, and the stevia leaf liquid extract that had been diluted and subsequently filtrated with a filter was injected for 20 μL. For the mass spectrometry part, Orbitrap Elite MS (from Thermo Fisher Scientific) equipped with an ESI ion source was used. The mass spectrometry measurement was carried out in a negative ion measurement mode at m/z in a range of 150-2000 with resolution set to 60,000. The MS/MS measurement was carried out by selecting the targeted m/z of 1095.4 or 1257.5 and in a CID mode where fragmentation was induced by collision with an inert gas. The ion with the highest intensity in the MS/MS spectrum was targeted for $MS^3$. Irradiation of energy required for fragmentation was performed at the standard collision energy unique to the apparatus, i.e., 35.

In order to study the fragmented pattern of Novel steviol glycosides 1 and 2, standard samples rebaudiosides A, D and M with known structures were subjected to MS/MS and $MS^3$ fragmentation pattern analyses. As a result, MS/MS of the novel steviol glycoside gave data showing that the highest ion intensity appeared at the peak where all sugar chains attached to C-19 via an ester bond were released. This result represents the total molecular weight of the sugar chains attached to the carbon of C-19 via an ester bond.

Figure 4:
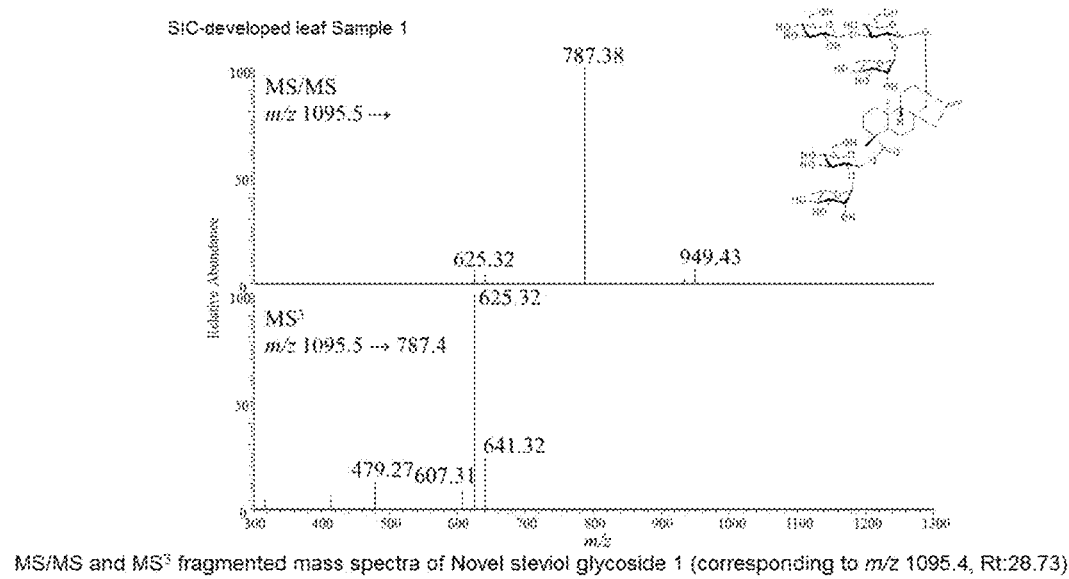
FIG. 4 illustrates a diagram showing MS/MS and MS$^3$ fragmented mass spectra of Novel steviol glycoside 1.

The MS/MS and $MS^3$ fragmented mass spectra of Novel steviol glycoside 1 (corresponding to m/z 1095.4, Rt:28.73) are shown in FIG. 4. In the MS/MS spectrum of the novel steviol glycoside, the main peak was detected at m/z of 787.38 corresponding to release of one Glc moiety and one Rha moiety. From these results, the number of sugar chains attached to the carbon of C-19 via an ester bond was found to be one Glc moiety and one Rha moiety. In order to acquire further structural information, a $MS^3$ spectrum was acquired by fragmenting the main peak at m/z of 787.4 obtained by MS/MS. As a result, a spectrum having the same peak pattern as the MS) spectrum of rebaudioside C (949.4→187.4→) was acquired. Accordingly, the sugar chains attached to C-13 were presumed to be the same as rebaudioside C. The deduced structure is shown in FIG. 4.

Figure 5:
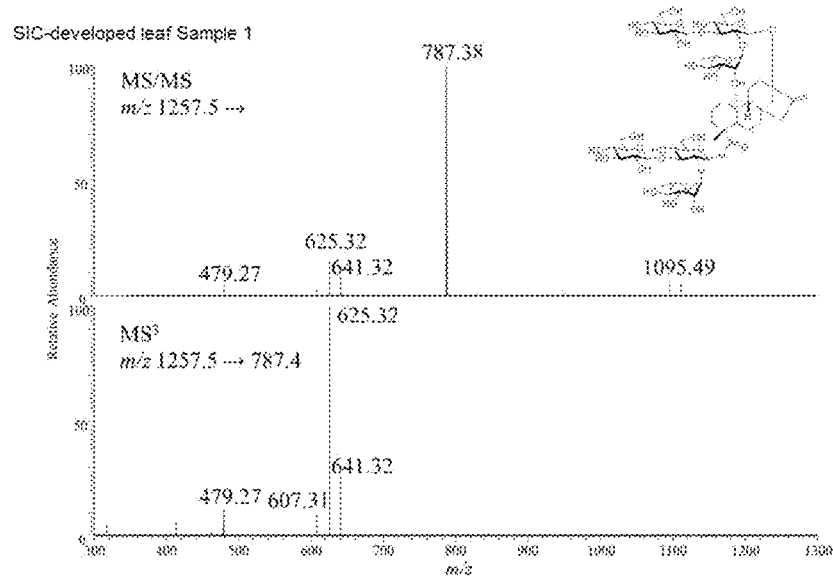
FIG. 5 illustrates a diagram showing MS/MS and MS$^3$ fragmented mass spectra of Novel steviol glycoside 2.
Figure 6:
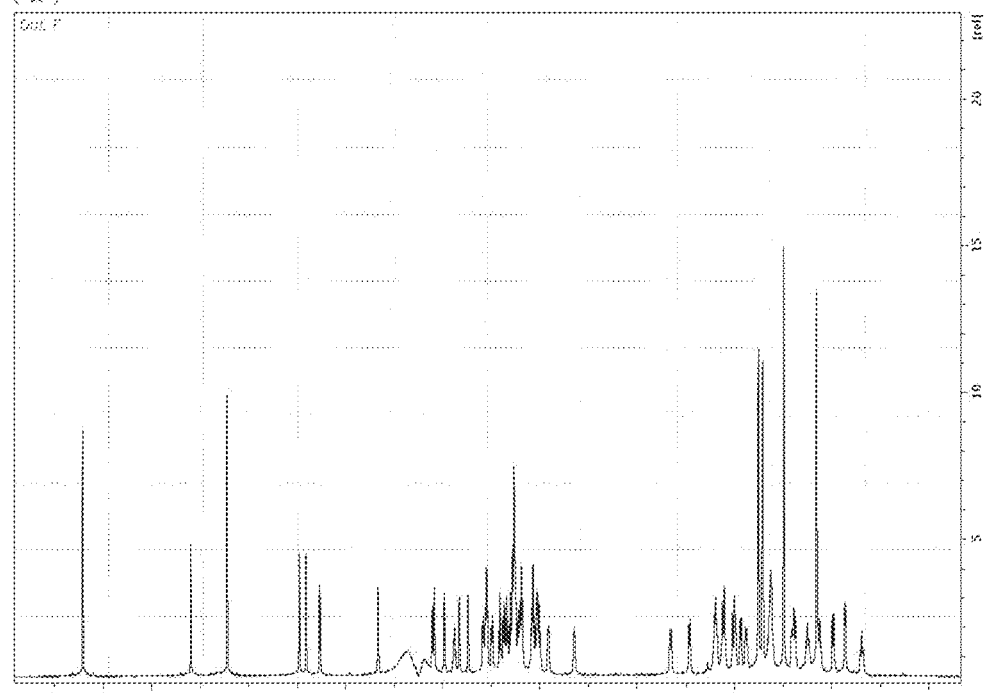
FIG. 6 illustrates (a) a diagram showing a $^1$H-NMR spectrum of Compound 15 (800 MHz, Pyr-d5); and (b) a diagram showing a $^{13}$C-NMR spectrum of Compound 15 (200 MHz, Pyr-d5)
Figure 6:
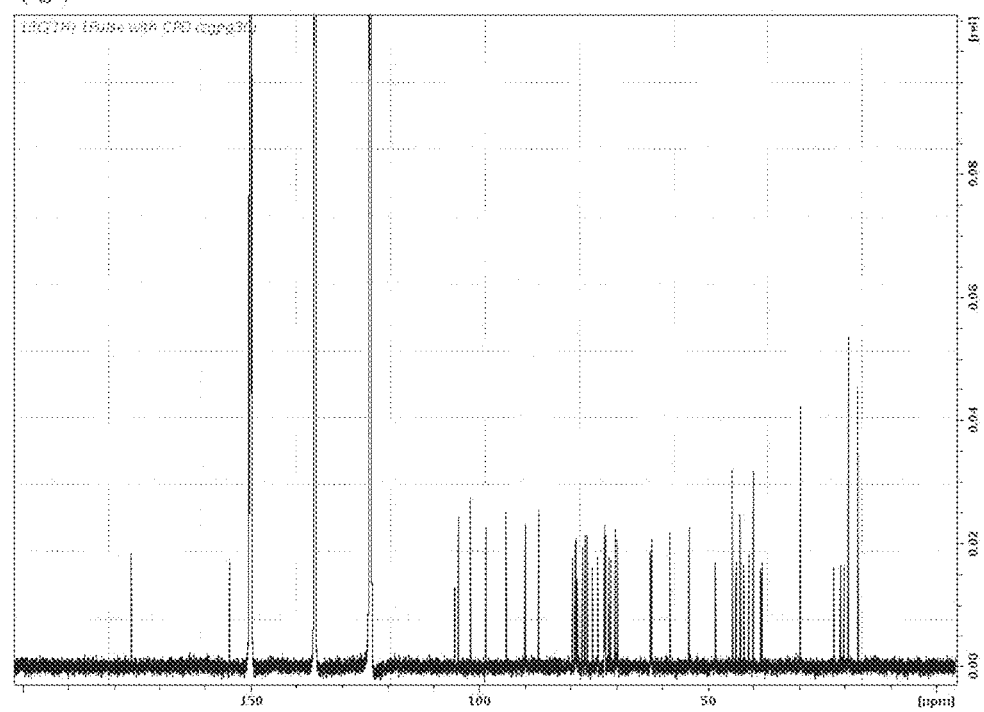
Figure 7:
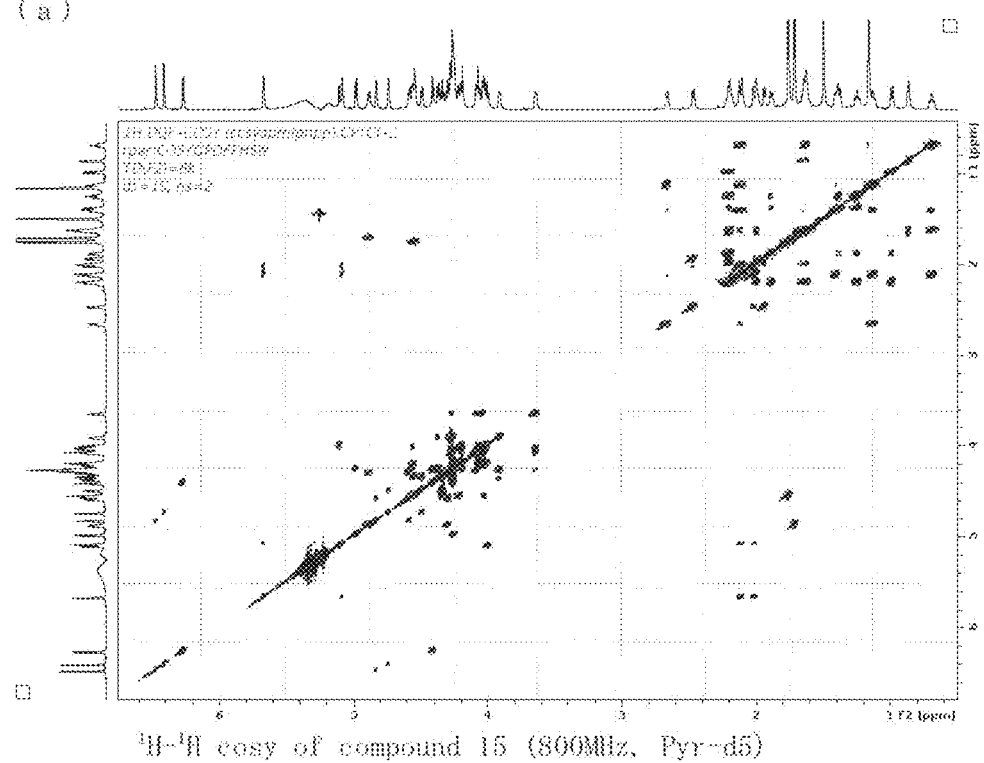
FIG. 7 illustrates (a) a diagram showing a $^1$H-$^1$H cosy spectrum of Compound 15 (800 MHz, Pyr-d5); and (b) a diagram showing a HSQC spectrum of Compound 15 (800 MHz, Pyr-d5).
Figure 7:
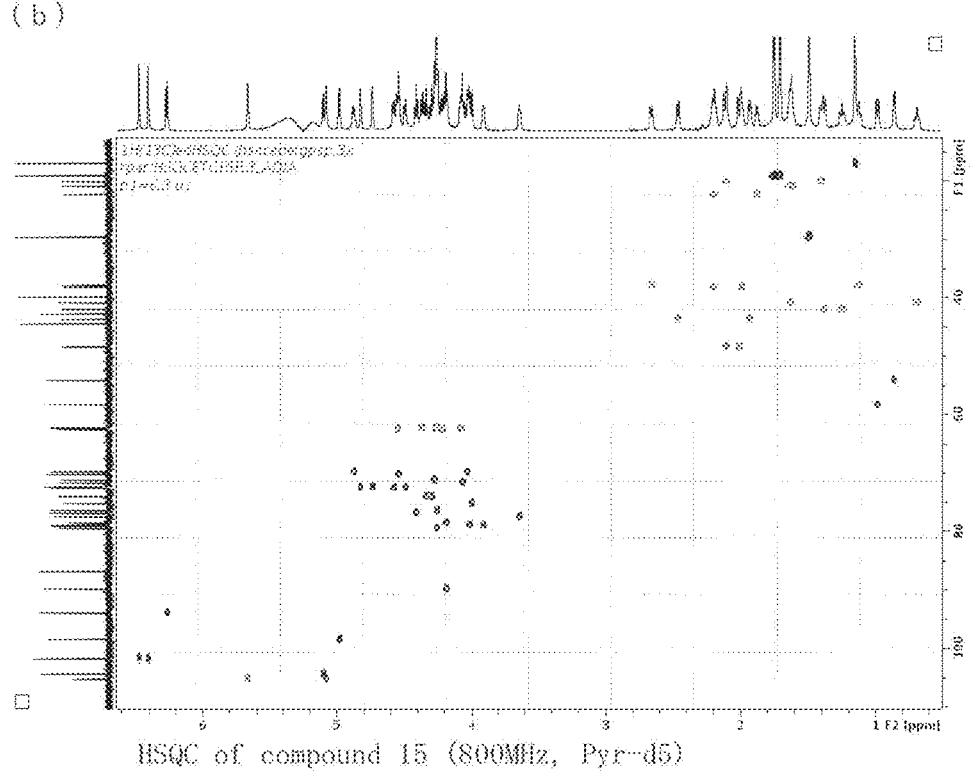
Figure 8:
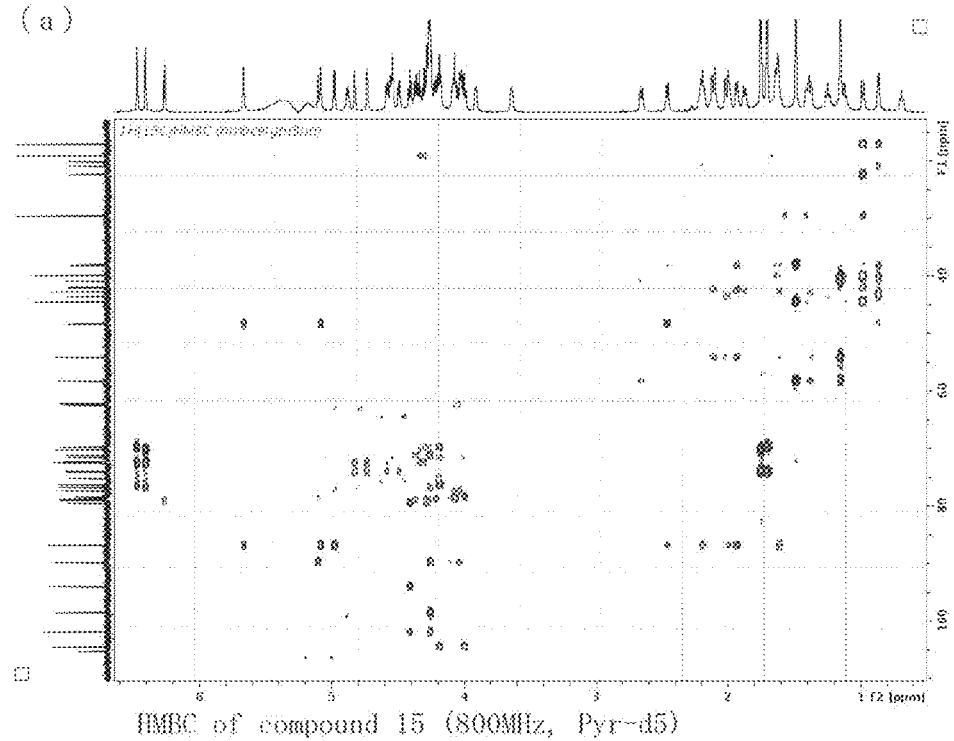
FIG. 8 illustrates (a) a diagram showing a HMBC spectrum of Compound 15 (800 MHz, Pyr-d5); and (b) a diagram showing a TOCSY spectrum of Compound 15 (800 MHz, Pyr-d5).
Figure 8:
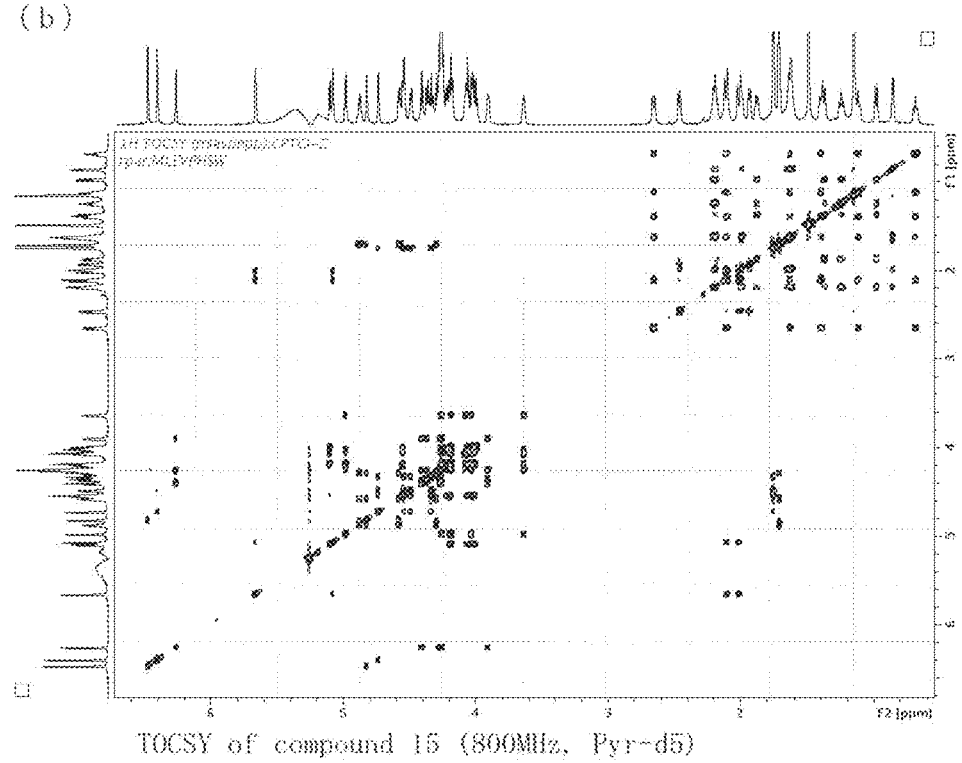
Figure 9:
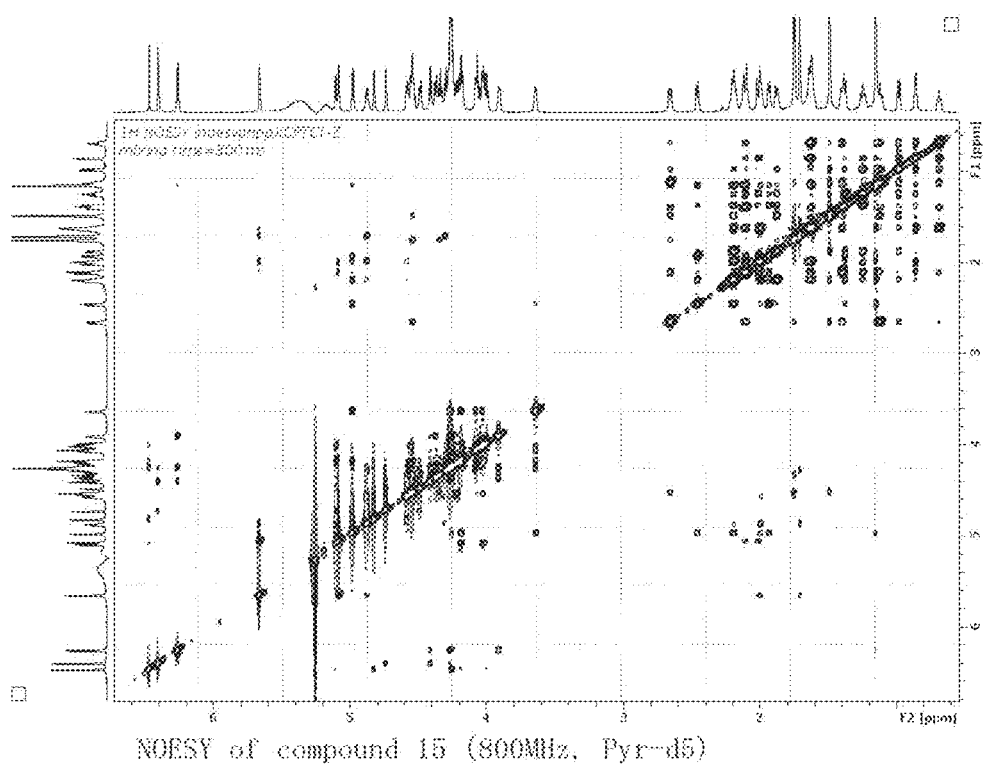
FIG. 9 illustrates a diagram showing a NOESY spectrum of Compound 15 (800 MHz, Pyr-d5).
Figure 10:
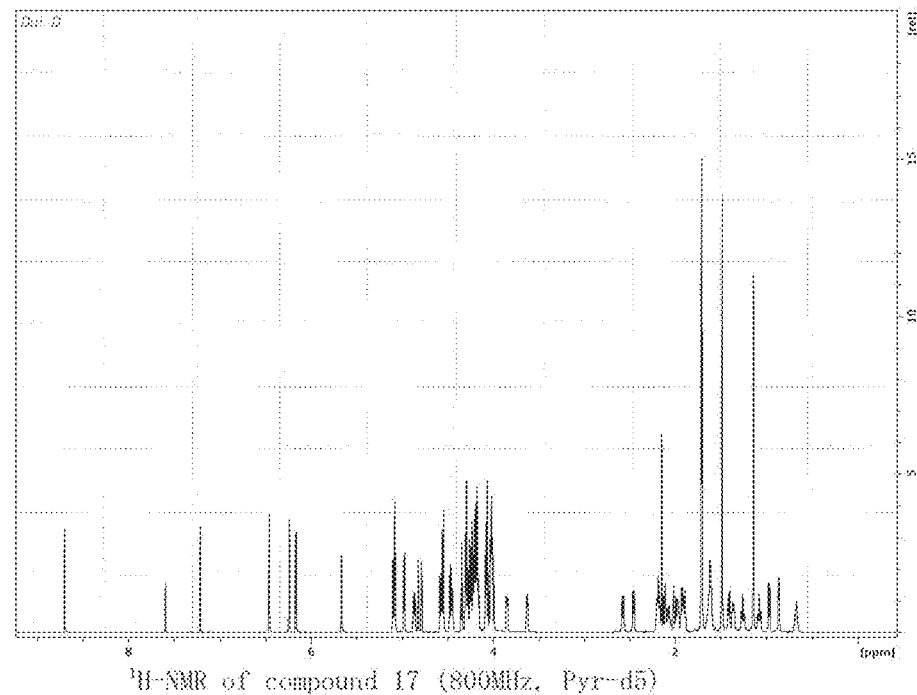
FIG. 10 illustrates (a) a diagram showing a $^1$H-NMR spectrum of Compound 17 (800 MHz, Pyr-d5); and (b) a diagram showing a $^{13}$C-NMR spectrum of Compound 17 (200 MHz, Pyr-d5)
Figure 10:
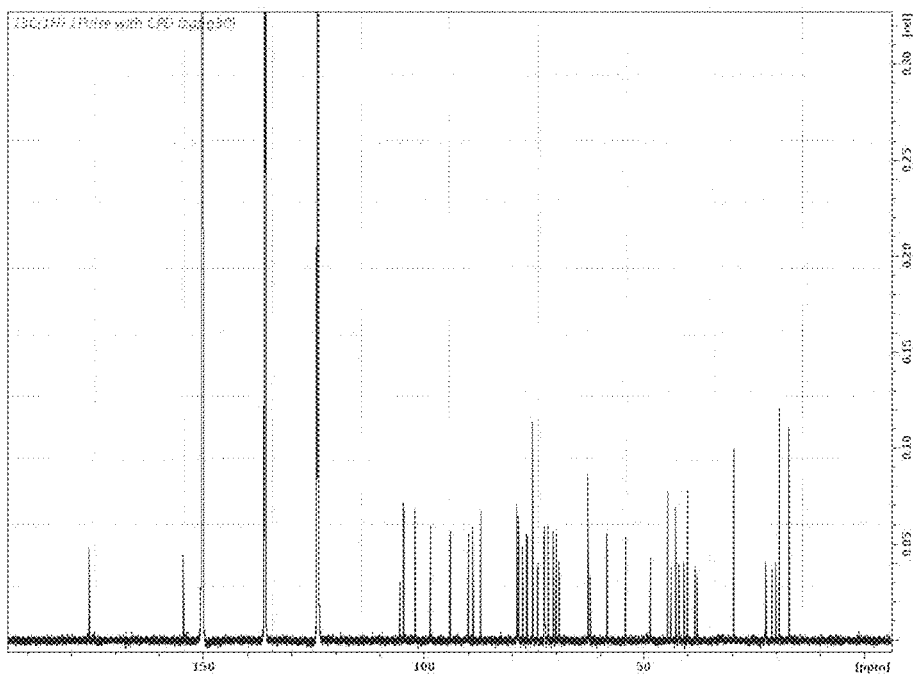
Figure 11:
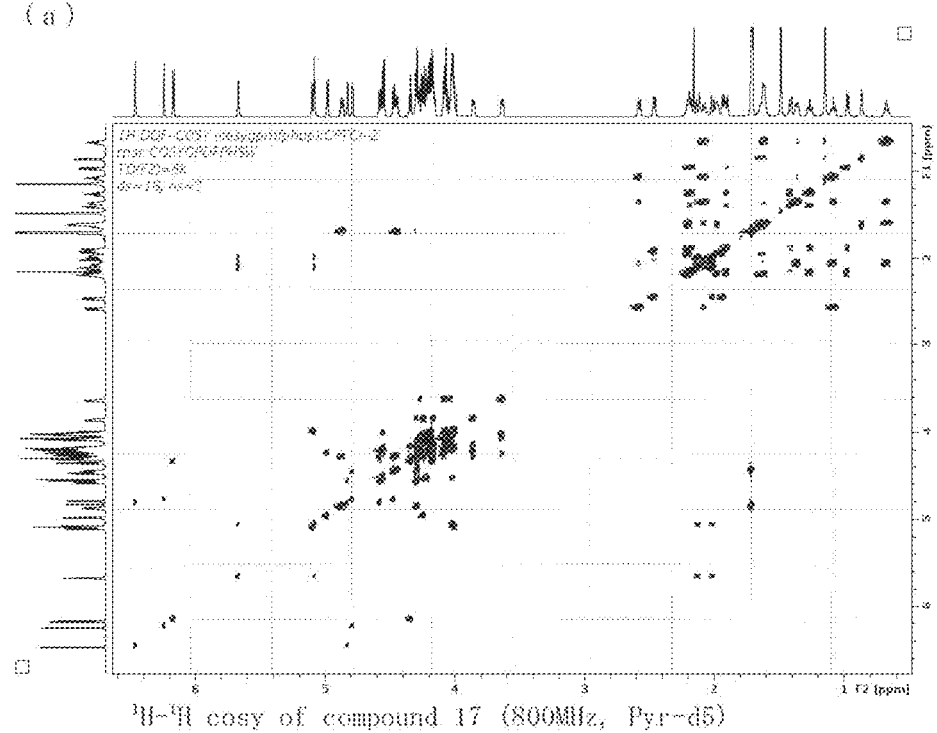
FIG. 11 illustrates (a) a diagram showing a $^1$H-$^1$-H cosy spectrum of Compound 17 (800 MHz, Pyr-d5) and (b) a HSQC spectrum of Compound 17 (800 MHz, Pyr-d5)
Figure 11:
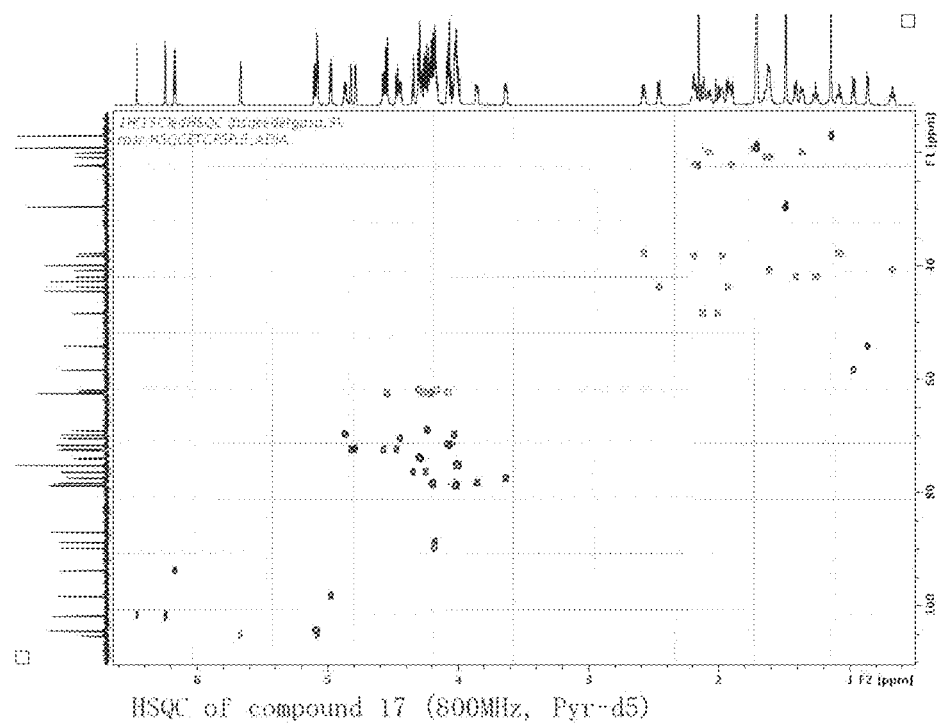
Figure 12:
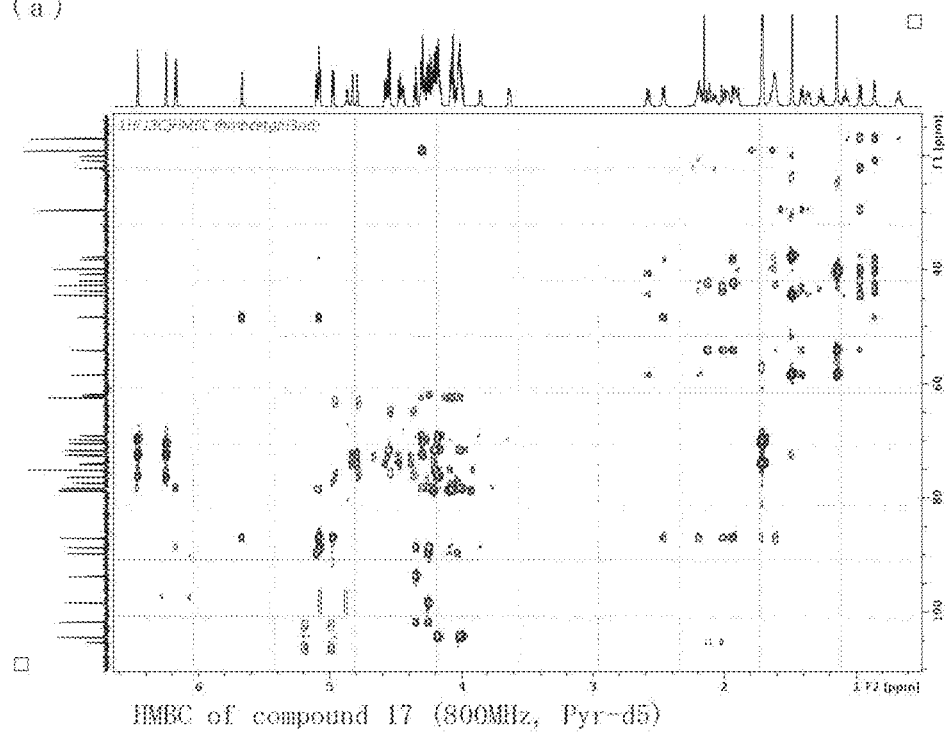
FIG. 12 illustrates (a) a diagram showing a HMBC spectrum of Compound 17 (800 MHz, Pyr-d5); and (b) a diagram showing a TOCSY spectrum of Compound 17 (800 MHz, Pyr-d5).
Figure 12:
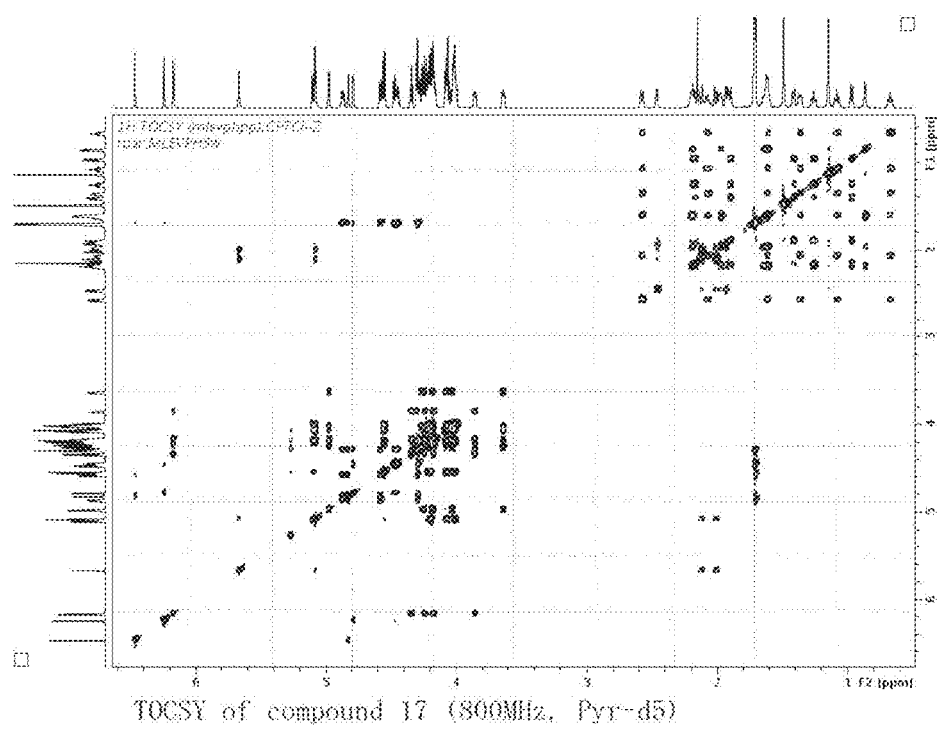
Figure 13:
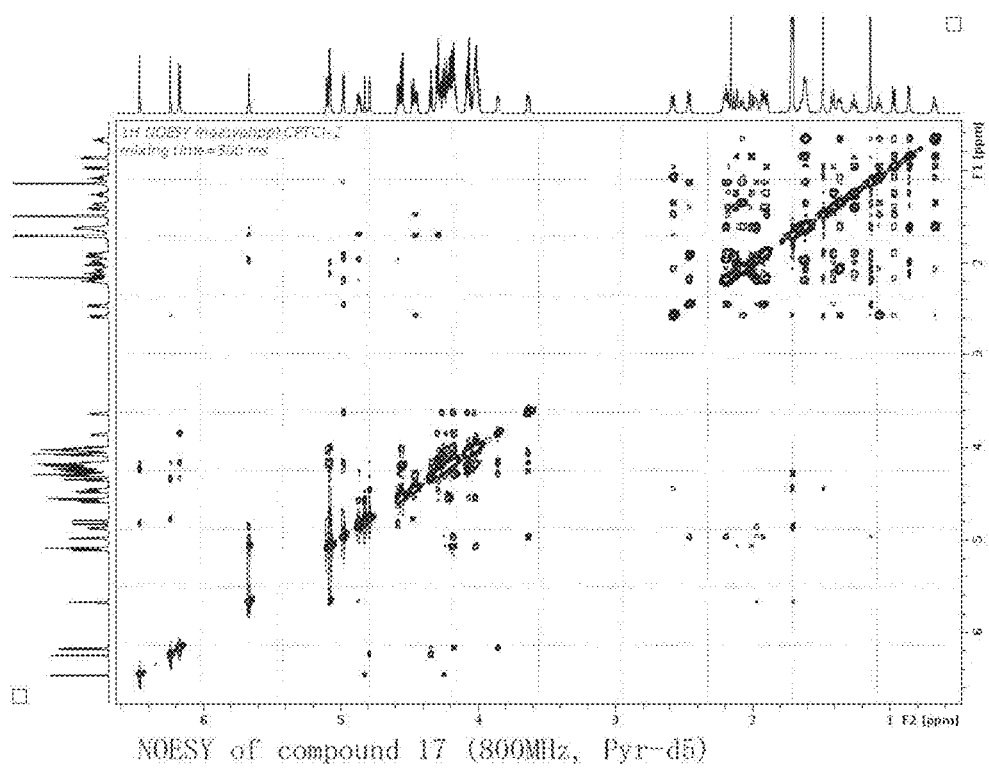
FIG. 13 illustrates a diagram showing a NOESY spectrum of Compound 17 (800 MHz, Pyr-d5).

The MS/MS and $MS^3$ fragmented mass spectra of Novel steviol glycoside 2 (corresponding to m/z 1257.5, Rt:28.50) are shown in FIG. 5. In the MS/MS spectrum of the novel steviol glycoside, the main peak was detected at m/z of 787.38 corresponding to release of two Glc moieties and one Rha moiety. From these results, the number of sugar chains attached to the carbon of C-19 via an ester bond was found to be two Glc moieties and one Rha moiety. In order to acquire further structural information, a $MS^3$ spectrum was acquired by fragmenting the main peak at m/z of 787.4 obtained by MS/MS. As a result, a spectrum having the same peak pattern as the $MS^3$ spectrum of rebaudioside C (949.4→787.4→) was acquired. Accordingly, the sugar chains attached to C-13 were presumed to be the same as rebaudioside C. The deduced structure is shown in FIG. 5.

(ii) Chemical synthesis of deduced steviol glycoside standard product by chemical reaction

[Synthesis of Novel Steviol Glycoside 1]

(1) Outline of Synthetic Pathways

Scheme 7
Strategy for synthesizing Novel steviol glycoside 1

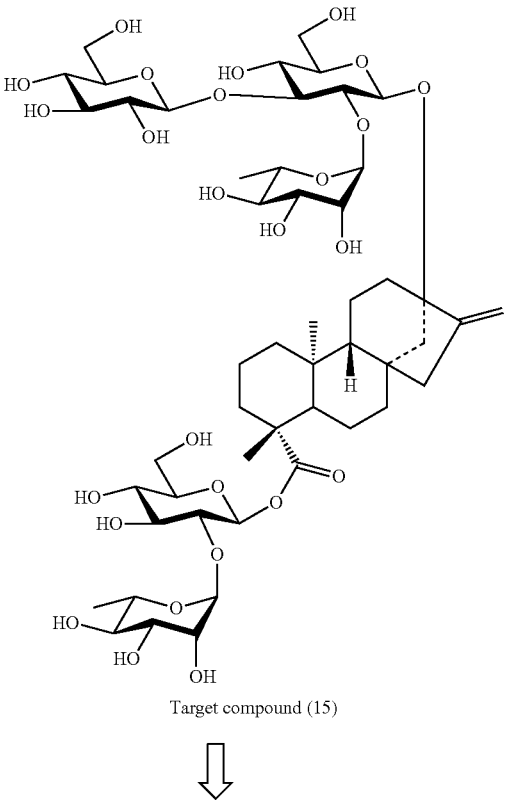

Target compound (15)

⇩

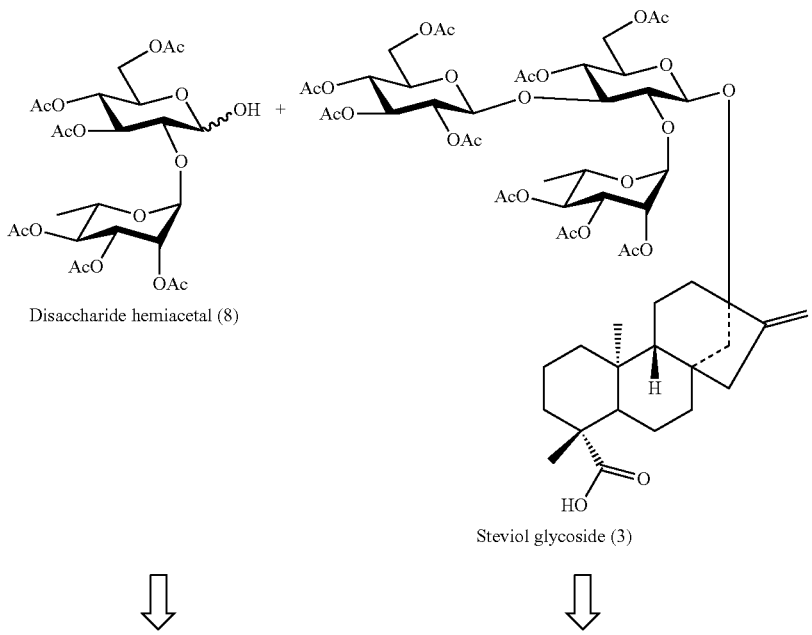

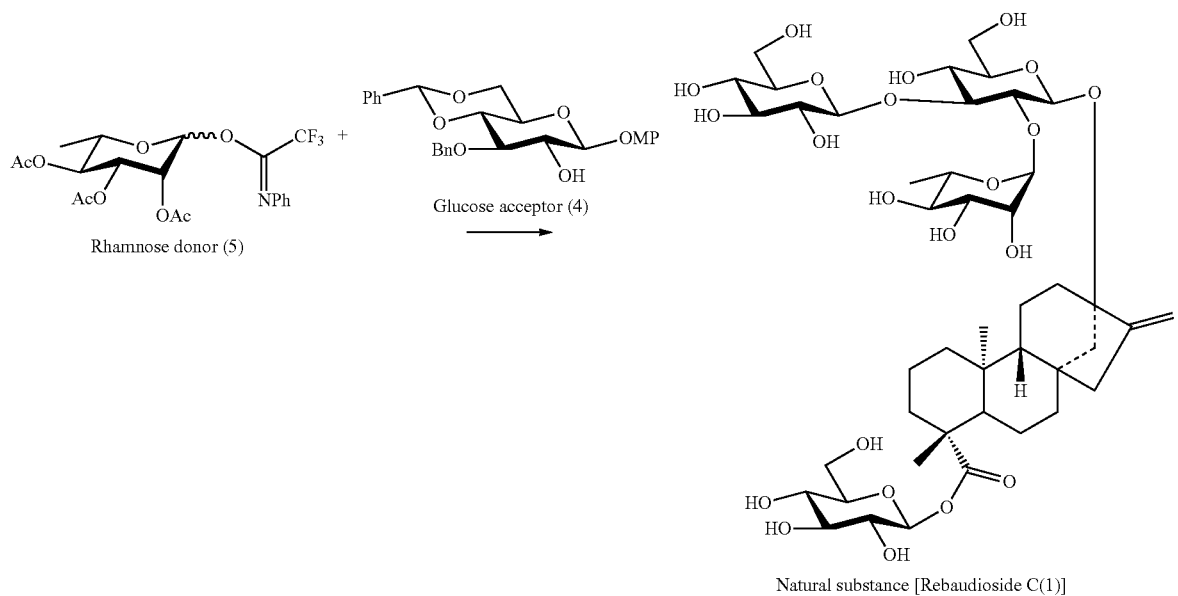

As can be appreciated from Scheme 7, for the synthesis of Novel steviol glycoside 1 (Compound 15), the steviol glycoside (Compound 3) and the disaccharide hemiacetal (Compound 8) were condensed via the Mitsunobu reaction to obtain the backbone of Novel steviol glycoside 1 (Compound 15). For synthesis of the steviol glycoside, a known natural substance, rebaudioside C (Compound 1), was purchased from Ark Pharm, the ester bond at C-19 of steviol was subjected to alkaline hydrolysis and then the hydroxyl groups of the sugar chain were protected with acetyl (Ac) groups to obtain the steviol glycoside. For synthesis of the disaccharide hemiacetal, a disaccharide backbone was produced by condensation reaction between an appropriately protected glucose acceptor (Compound 4) and a rhamnose donor (Compound 5), and the protecting group at the anomeric carbon of the reducing end was deprotected to give the disaccharide hemiacetal. The resulting steviol glycoside and disaccharide hemiacetal were subjected to condensation via the Mitsunobu reaction, where the reaction proceeded with good yield and high β-selectivity of 75% (α/β=1/20). The protecting groups of the resulting compound were deprotected, thereby obtaining Novel steviol glycoside 1 (15).

Next, each of the synthesis steps will be described.

(2) Synthesis of Steviol Glycoside

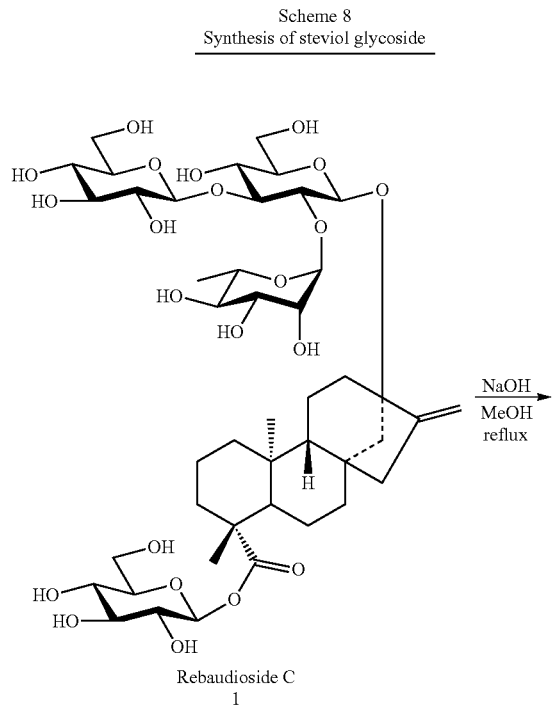

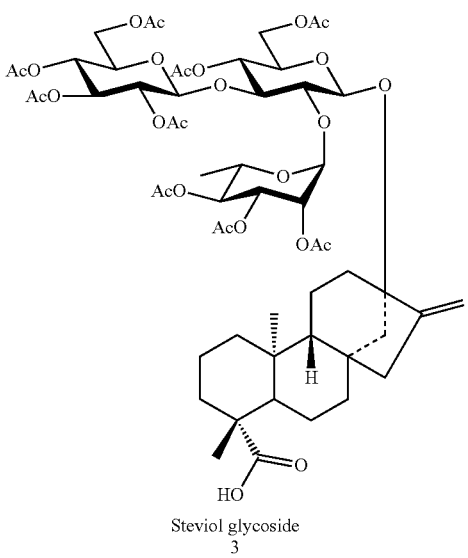

As can be appreciated from Scheme 8, for synthesis of the steviol glycoside (Compound 3), rebaudioside C (Compound 1) (1.0 g, 1.05 mmol) purchased from Ark Pharm was dissolved in methanol (10 mL) and water (10 mL), added with 4 mol/L of sodium hydroxide (2.6 mL, 10.4 mmol) at room temperature, and refluxed at 100° C. for 20 hours. After confirming the completion of the reaction by TLC (chloroform/methanol/water=5/4/0.1, Rf value=0.9), the reaction solution was neutralized with cation exchange resin Dowex MAC-3 hydrogen form (SIGMA-ALDRICH) (pH 7). After the resin was removed by filtration, the resultant was concentrated under a reduced pressure. The resulting syrup was dried for 18 hours by end using a vacuum pump to give Compound 2 (828 mg, quant.).

Compound 2 (828 mg, 1.05 mmol) was dissolved in pyridine (20 mL), added with acetic anhydride (5 mL) at room temperature and agitated at room temperature for 48 hours. After confirming the completion of the reaction by TLC (ethyl acetate/hexane=2/1, Rf value=0.5), a saturated sodium hydrogen carbonate solution (5 mL) was added, and the reaction solution was concentrated under a reduced pressure. The resulting syrup was subjected to silica gel column chromatography and an eluate (ethyl acetate/hexane=2/1) was used to give Compound 3 (1.1 g, 92%).

[Compound 3]

$^1$H-NMR (CDCl$_3$, 400 MHz) δ 0.81 (m, 2H), 0.83-1.45 (complex, 19H), 1.39-1.91 (complex, 24H), 1.91-235 (s, 30H), 3.58 (m, 1H), 3.71-3.81 (complex, 4H), 3.95-4.12 (complex, 7H), 4.34-4.46 (complex, 3H), 4.56-4.66 (complex, 4H), 4.69-4.92 (complex, 7H), 5.05-5.14 (complex, 5H), 5.23-5.38 (complex, 6H), 5.45 (s, 1H); $^{13}$C-NMR (CDCl$_3$, 100 MHz) δ 15.9, 17.3, 19.1, 20.5, 20.7, 20.8, 20.9, 21.1, 21.5, 21.7, 29.1, 37.8, 38.0, 39.5, 40.7, 41.4, 42.2, 43.8, 48.4, 53.8, 56.8, 61.6, 63.0, 65.5, 66.8, 68.0, 68.6, 69.3, 69.6, 69.8, 70.5, 70.9, 71.6, 71.9, 72.4, 72.8, 73.9, 74.9, 81.3, 87.3, 96.6, 96.8, 99.2, 99.4, 125.4, 128.3, 129.1, 137.9, 151.9, 168.9, 169.2, 169.5, 169.6, 169.8, 170.1, 170.2, 170.3, 170.6, 170.9, 176.8, 183.4.

(3) Synthesis of Disaccharide Hemiacetal

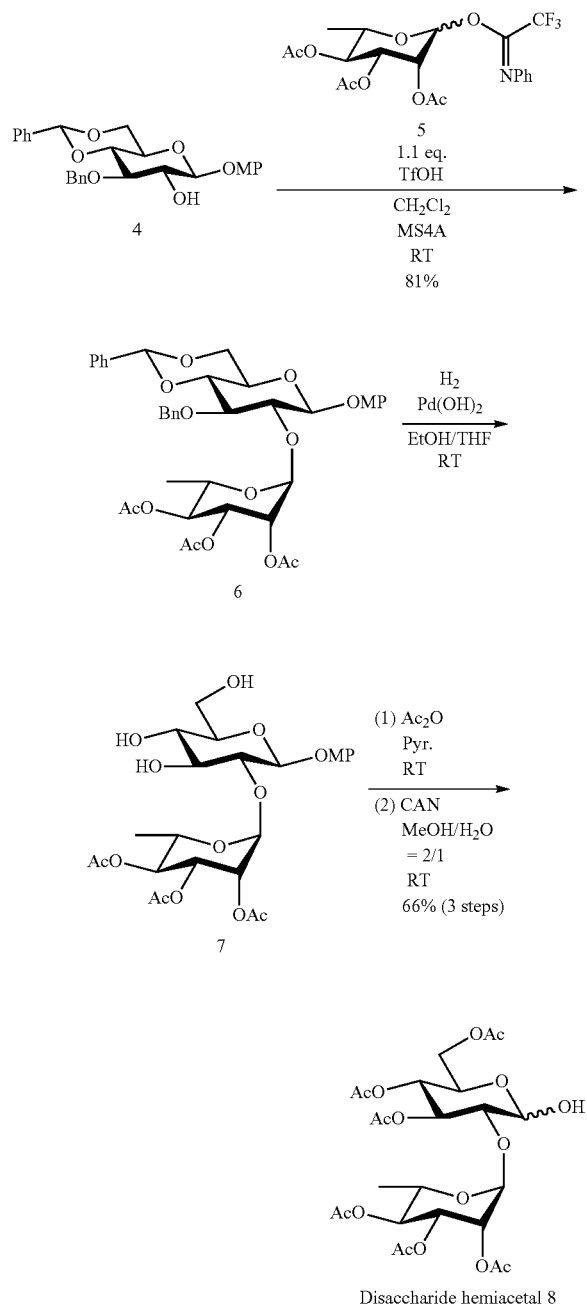

Disaccharide hemiacetal 8

As can be appreciated from Scheme 9, for synthesis of the disaccharide hemiacetal (Compound 8), 4-methoxyphenyl 3-O-benzyl-4,6-O-benzylidine-β-D-glucopyranoside (Compound 4) (3.0 g, 6.46 mmol) purchased from Tokyo Chemical Industry, Compound 5 (3.3 g, 7.10 mmol) and 4A molecular sieves (6.0 g) were dissolved in dichloromethane (136 mL), added with trifluoromethanesulfonic acid (114 μL, 1.29 mmol) at room temperature, and agitated at room temperature for 18 hours. After confirming the completion of the reaction by TLC (ethyl acetate/hexane=1/2, Rf value=0.5), the resultant was neutralized with triethylamine (100 μL) (pH 8), 4 Å molecular sieves 21) was removed by filtration, and the resultant was concentrated under a reduced pressure. The resulting syrup was subjected to silica gel column chromatography and an eluate (ethyl acetate/hexane=1/1.5) was used to give Compound 6 (3.9 g, 81%).

[Compound 6]
$^1$H-NMR (CDCl$_3$, 400 MHz) δ 1.18 (d, J=6.4 Hz, 3H, H-6 of Rha), 1.96 (s, 3H, OAc), 1.98 (s, 3H, OAc), 2.07 (s, 3H, OAc), 3.51 (m, 1H, H-5), 3.73-3.81 (complex, 5H, H-4, H-6, OMe), 3.83-3.96 (complex, 2H, H-2, H-3), 4.28 (m, 1H, H-5 of Rha), 4.36 (m, 1H, H-6'), 4.70 (d, 1H, CH$_2$Ph), 4.95 (d, 1H, CH$_2$Ph), 4.99 (d, J=7.2 Hz, 1H, H-1), 5.03 (t, 1H, H-4 of Rha), 5.20 (dd, 1H, H-3 of Rha), 5.32 (s, 1H, H-1 of Rha), 5.34 (m, 1H, H-2 of Rha), 5.57 (s, 1H, CHPh), 6.90 (dd, 4H, OMePh), 7.21-7.49 (complex, 10H, Ph); $^{13}$C-NMR (CDCl$_3$, 100 MHz) δ 14.2, 17.4, 20.8, 20.9, 21.0, 22.8, 31.7, 55.8, 66.2, 66.7, 68.8, 69.4, 69,5, 71.0, 75.2, 76.7, 77.5, 81,7, 81.8, 98.4, 100.8, 101.4, 114.8, 118.3, 126.1, 127.9, 128.4, 128.5× 2, 129.2, 137.2, 137.9, 150.8, 155.7, 169.9, 170.1, 170.2.

Compound 6 (3.9 g, 5.29 mmol) was dissolved in ethanol (27 mL) and THF (27 mL), added with palladium hydroxide (2.0 g) at room temperature, and agitated in an hydrogen atmosphere at room temperature for 18 hours. After confirming the completion of the reaction by TLC (chloroform/methanol=10/1, Rf value=0.2), palladium hydroxide was removed by filtration and the filtrate was concentrated under a reduced pressure to give Compound 7 (2.9 g, quant.).

Compound 7 (1.1 g, 1.97 mmol) was dissolved in pyridine (20 mL), added with acetic anhydride (740 μL, 7.88 mmol) at room temperature, and agitated at room temperature for 24 hours. After confirming the completion of the reaction by TLC (ethyl acetate/hexane=1/1, Rf value=0.6), azeotropic distillation with toluene (30 mL) was repeated for three times. Subsequently, the resultant was concentrated under a reduced pressure and the resulting syrup was dissolved in acetonitrile (14 mL) and water (7.0 mL), added with cerium ammonium nitrate (3.2 g, 5.91 mmol) at room temperature, and agitated at room temperature for 30 minutes. After confirming the completion of the reaction by TLC (ethyl acetate/hexane=1.5/1, Rf value=0.5), the resultant was diluted with ethyl acetate, the organic layer was washed with water and a saturated aqueous sodium hydrogen carbonate solution, and dried with magnesium sulfate. Magnesium sulfate was removed by filtration and the resultant was concentrated under a reduced pressure. The resulting syrup was subjected to silica gel column chromatography and an eluate (ethyl acetate/hexane=1/1) and (toluene/ethyl acetate=3/1) were used to give Compound 8 (721 mg, 66%, 3 steps).

[Compound 8]
$^1$H-NMR (CDCl$_3$, 400 MHz) δ 1.16-1.19 (complex, 4.5H, H-6α of Rha, H-6β of Rha), 1.97-2.34 (complex, 27 H, OAc), 3.58 (t, 0.5H, H-2β), 3.72-3.75 (complex, 1.5H, H-2α, H-5β), 4.00 (m, 1H, H-4α of Rha), 4.05-4.16 (complex, 1.5H), 4.21-4.27 (complex, 3H), 4.76 (d. J=7.6 Hz, 0.5H, H-1β), 4.86 (s, 1H, H-1α of Rha), 4.91 (s, 0.5H, H-1β of Rha), 4.98-5.08 (complex, 4.614), 5.23-5.26 (complex, 2H), 5.34 (d, J=3.2 Hz, 1H, H-1α), 5.48 (t, 1H, H-3α): $^{13}$C-NMR (CDCl$_3$, 100 MHz) δ 17.2, 17.5, 20.7×2, 20.8×3, 20.9×2, 21.0, 21.6, 62.1, 62.2, 67.2, 67.3, 67.5, 68.5, 68.6, 68.7, 70.0, 70.4, 71.0, 74.2, 77.4, 77.9, 79.3, 92.0, 75.7, 98.4, 99.2, 125.4, 128.3, 129.1, 137.9, 169.8, 169.9×2, 170.0, 170.12, 170.2, 170.4, 170.9×2.

(4) Synthesis of Compound 15

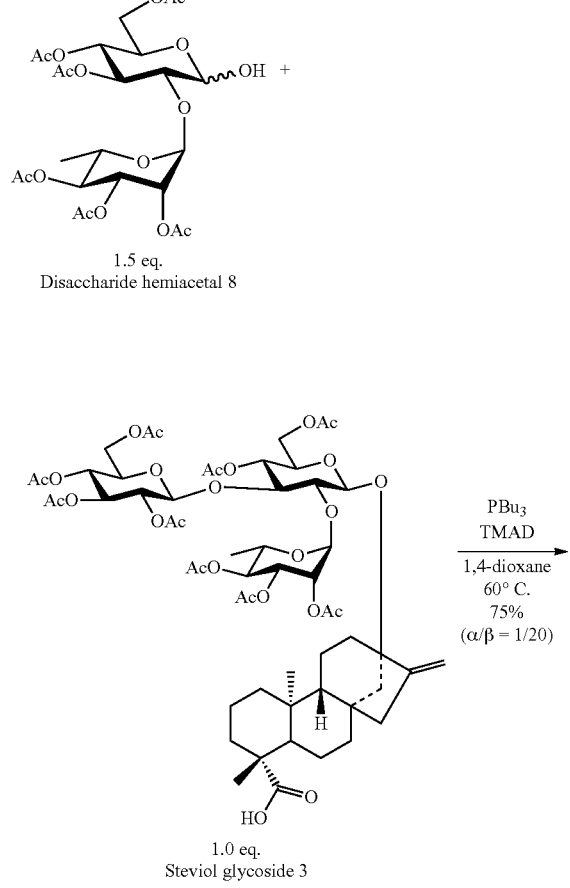

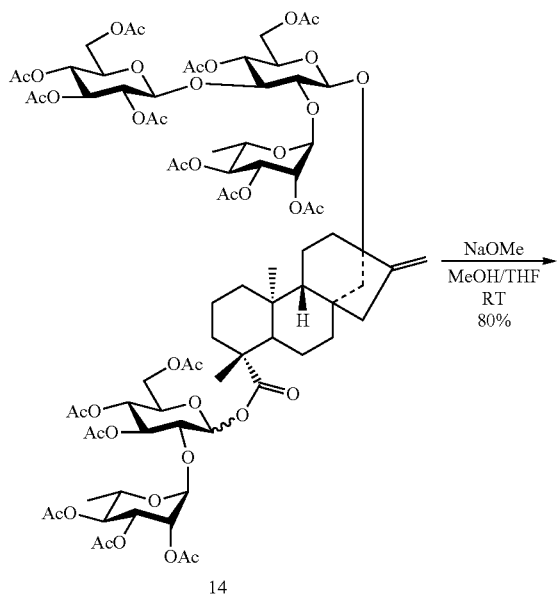

Target compound 15

As can be appreciated from Scheme 10, for synthesis of Compound 15, Compound 8 (291 mg, 0.503 mmol) and Compound 3 (391 mg, 0.335 mmol) were dissolved in 1,4-dioxane (17 mL), added with tributylphosphine (252 μL, 1.01 mmol) and 1,1'-azobis (N,N'-dimethylformamide) (TMAD) (173 mg, 1.01 mmol) at room temperature, and agitated at 60° C. for 6 hours. After confirming the completion of the reaction by TLC (toluene/ethyl acetate=1/1, Rf value=0.4), the resultant was diluted with ethyl acetate, the organic layer was washed with water, a saturated aqueous sodium hydrogen carbonate solution and saturated saline, and dried with magnesium sulfate. Magnesium sulfate was removed by filtration, and the resultant was concentrated under a reduced pressure. The resulting syrup was subjected to silica gel column chromatography and an eluate (toluene/ethyl acetate=1.5/1) was used to give Compound 14 (435 mg, 75%, α/β=1/20).

[Compound 14]

$^1$-H-NMR (CDCl$_3$, 400 MHz) δ 0.50-1.18 (complex, 7H), 1.15 (d, 3-H, H-6 of Rham), 1.24 (s, 3H), 1.40-2.32 (complex, 70H), 3.60 (m, 1H), 3.73 (m, 2H), 3.82-4.28 (complex, 1.0H), 4.40-4.48 (complex, 2H), 4.63 (d, J=7.6 Hz, 1H), 4.72 (d, J=8.0 Hz, 1H), 4.75-4.88 (complex, 3H), 4.98 (s, 1H), 5.01-5.18 (complex, 8H), 5.24-5.31 (complex, 4H), 5.32 (s, 1H), 5.71 (d, J=7.6 Hz, 1H, H-1β), 6.31 (d, J=3.0 Hz, 0.05H, H-1α) $^{13}$C-NMR (CDCl$_3$, 100 MHz) δ 16.6, 17.4, 17,6, 20.5, 20.7×2, 20.8×3, 20.9×3, 21.6, 29.0, 39.5, 42.5, 44.1, 53.8, 57.9, 61.7, 66.6, 67.4, 68.0, 68.3, 68.5, 68.7, 69.7, 69.8, 70.8, 71.1, 71.4, 71.9×2, 72.4, 72.9, 74.2, 75.1, 86.6, 92.2, 96.4, 96.9, 97.7, 99.3, 125.4, 128.3, 129.1, 152.9, 169.0, 169.5, 169.8×2, 169.9, 170.0, 170.1, 170.2×2, 170.3, 170.5, 170.6, 170.9×2, 174.6.

Compound 14 (435 mg, 0.252 mmol) was dissolved in methanol (2.0 mL) and THF (2.0 mL), added with sodium methoxide (0.5M in MeOH) (0.5 mL, 0.252 mmol) at room temperature, and agitated at room temperature for 18 hours. After confirming the completion of the reaction by TLC (chloroform/methanol/water=5/4/1, Rf value=0.4), the resultant was concentrated under a reduced pressure. The resulting syrup was subjected to gel filtration column (GE Healthcare, Sephadex LH-20, ethanol) to give Compound 15 (220 mg, 80%, α/β=1/20). Subsequently, the β-form of Compound 15 was isolated by preparative HPLC (C18 YMC HPLC column, 20 mM aqueous ammonium acetate solution/ 90% acetonitrile/10% water=70/30-10/90, 45 minutes), and subjected to lyophilization. The structural analysis data of Compound 15 by nuclear magnetic resonance (NMR) method is shown in FIGS. 6-9.

[Compound 15 (the β-form)]
$^1$H-NMR (pyridine-d5, 800 MHz) δ 0.68 (m, 1H), 0.86 (m, 1H), 0.98 (m, 1H), 1.11-1.15 (complex, 4H), 1.24 (m, 2H), 1.39 (m, 2H), 1.49 (s, 3H), 1.62 (m, 3H), 1.71 (d, 3H), 1.75 (d, 3H), 1.88 (m, 1H), 1.93 (m, 1H), 2.00 (m, 2H, 2.11 (m, 2H), 2.19 (m, 2H), 2.46 (m, 1H), 2.66 (m, 1H), 3.62 (m, 1H), 3.91 (m, 1H), 3.97-4.10 (complex, 5H), 4.17-4.42 (complex, 11H), 4.49 (m, 1H), 4.51-4.59 (complex, 3H), 4.73 (m, 1H), 4.82 (m, 1H), 4.87 (m, 1H), 4.98 (d, J=8.0 Hz, 1H), 5.08 (s, 1H), 5.10 (d, j=7.2 Hz, 1H), 5.66 (s, 1H), 6.26 (d, J=7.2 Hz, 1H), 6.41 (s, 1H), 6.47 (s, 1H); $^{13}$C-NMR (pyridine-d5, 200 MHz) δ 17.1, 19.2×2, 20.1, 20.9, 22.3, 29.6, 37.9, 38.2, 39.9, 40.9, 41.9, 42.8, 43.7, 44.5, 48.4, 54.1, 58.3, 62.3, 62.4, 62.5, 69.8×2, 70.2, 71.2, 71.6, 72.4, 72.5, 72.6, 74.0, 74.1, 75.2, 76.4, 76.8, 77.4, 78.5, 78.8, 79.0, 79.5, 86.9, 89.8, 94.0, 98.4, 101.8, 101.9, 104.4, 105.3, 154.5, 176.2.

$[α]_D$=-46.3° (c 0.05, MeOH)

MALDI-TOF-MS m/z found [M+Na]$^+$1119.5, $C_{50}H_{80}O_{26}$ calcd for [M+Na]$^+$ 1119.5.

[Synthesis of Novel Steviol Glycoside 2]
(1) Outline of Synthetic Pathways

Scheme 11
Strategy for synthesizing Novel steviol glycoside 2

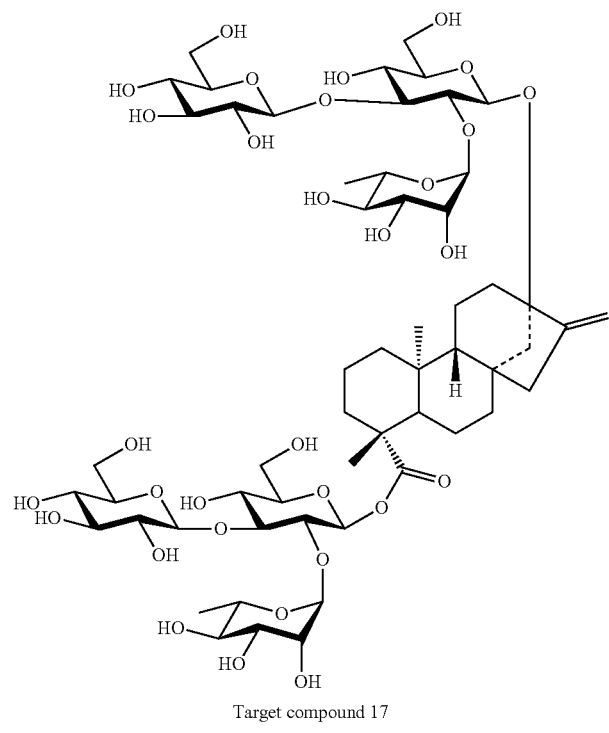

Target compound 17

-continued

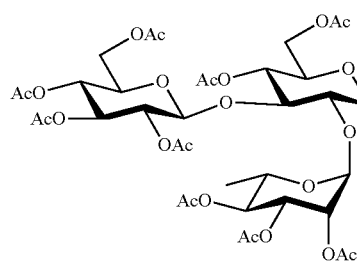

Trisaccharide hemiacetal 13

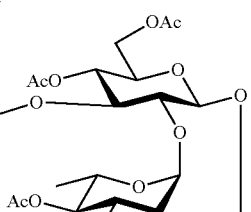

Steviol glycoside (3)

 

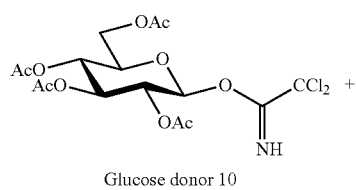

Glucose donor 10

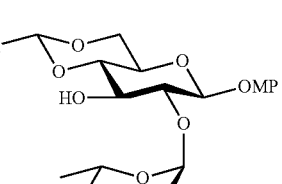

Disaccharide acceptor 9

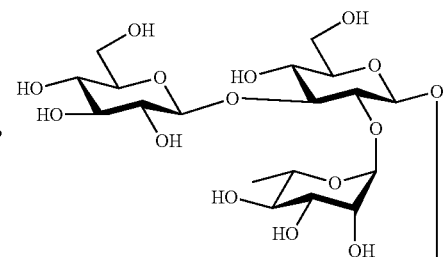

Natural substance [Rebaudioside C 1]

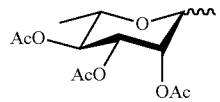

Rhamnose donor 5

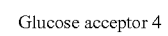

Glucose acceptor 4

As can be appreciated from Scheme 11, for the synthesis of Novel steviol glycoside 2 (Compound 17), the steviol glycoside (Compound 3) and the trisaccharide hemiacetal (Compound 13) were condensed via the Mitsunobu. reaction to obtain the backbone of Novel steviol glycoside 2. For synthesis of the steviol glycoside, a known natural substance, rebaudioside C (Compound 1), was purchased from Ark Pharm., the ester bond at C-19 of steviol was subjected to alkaline hydrolysis and then the hydroxyl groups of the sugar chain were protected with acetyl (Ac) groups to obtain the steviol glycoside. For synthesis of the trisaccharide hemiacetal, a disaccharide acceptor (Compound 9) was synthesized by condensation reaction between an appropriately protected glucose acceptor (Compound 4) and a rhamnose donor (Compound 5), which was subjected to condensation reaction with a glucose donor (Compound 10) to give the trisaccharide backbone. The protecting group at the anomeric carbon of the reducing end of the resulting trisaccharide was deprotected to give the trisaccharide hemiacetal. The steviol glycoside and the trisaccharide hemiacetal were subjected to condensation via the Mitsunobu reaction, where the reaction proceeded with good yield and high β-selectivity of 44% (α/β=1/10). The protecting groups of the resulting compound were deprotected, thereby obtaining Novel steviol glycoside 2.

Next, each of the synthesis steps will be described.

(2) Synthesis of Steviol Glycoside

Steviol glycoside was synthesized in the same manner as "Synthesis of Novel steviol glycoside 1".

(3) Synthesis of Trisaccharide Hemiacetal

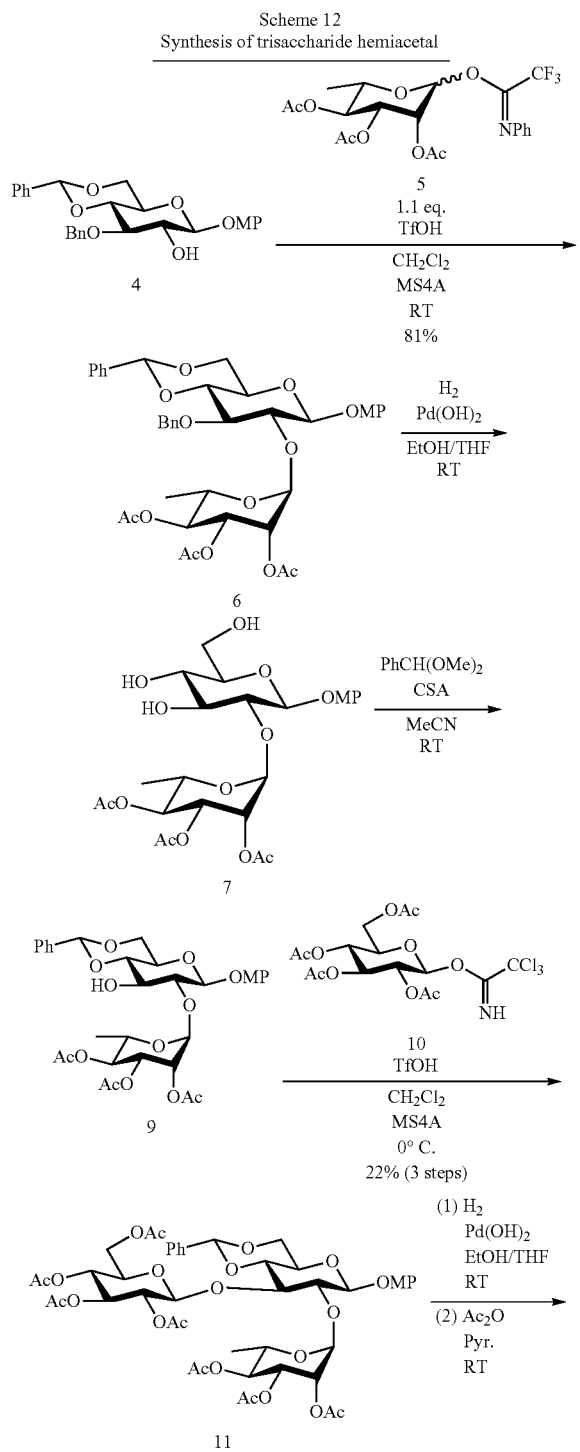

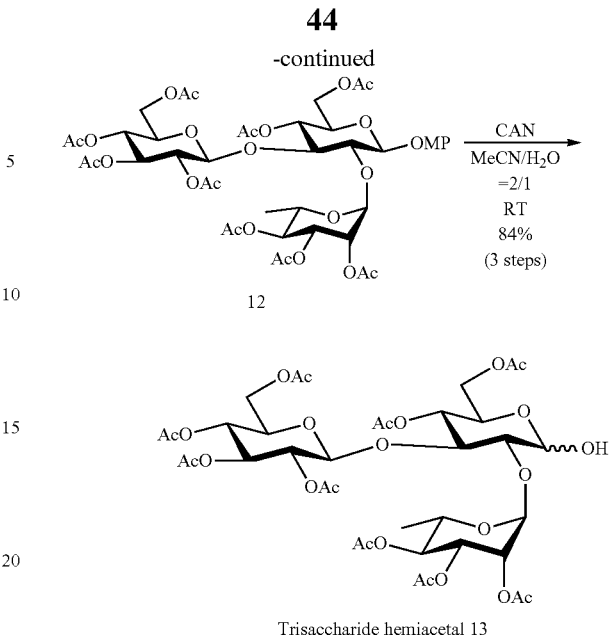

Trisaccharide hemiacetal 13

As can be appreciated from Scheme 12, Compounds 6 and 7 were obtained in the same manner as "Synthesis of Novel steviol glycoside 1".

Compound 7 (1.7 g, 3.04 mmol) was dissolved in acetonitrile (30 mL), added with benzaldehyde dimethyl acetal (681 μL, 4.57 mmol) at room temperature, and agitated at room temperature for 2 hours. The completion of the reaction was confirmed by TLC (ethyl acetate/hexane=1/1, Rf value=0.7). The resultant was neutralized with triethylamine (2 mL) (pH 8), and then concentrated under a reduced pressure to give Compound 9 (2.0 g).

Compound 9 (2.0 g, 3.04 mmol), Compound 10 (1.6 g, 3.34 mmol) and 4A molecular sieves (4.0 g) were dissolved in dichloromethane (64 mL), added with trifluoromethanesulfonic acid (114 μL, 1.29 mmol) at room temperature, and agitated at 0° C. for 6 hours. After confirming the completion of the reaction by TLC (ethyl acetate/hexane=1/1, Rf value=0.4), the resultant was neutralized with triethylamine (100 μL) (pH 8), 4 Å molecular sieves was removed by filtration, and the resultant was concentrated under a reduced pressure. The resulting syrup was subjected to silica gel column chromatography and an eluate (ethyl acetate/hexane=1/2) was used to give Compound 11 (650 mg, 22%, 3 steps).

[Compound 11]

(CDCl$_3$, 400 MHz) δ 1.16 (d, J=6.0 Hz, 1H, H-6 of Rha), 1.94-2.19 (complex, 21H, OAc), 3.43-3.52 (complex, 2H), 3.62-3.81 (complex, 5H, OMe), 3.96-4.04 (complex, 2H), 4.07-4.18 (complex, 3H), 4.28-4.35 (complex, 2H), 4.86 (d, J=8.0 Hz, 1H, H-1), 4.94-4.98 (complex, 2H, H-1), 5.01-5.11 (complex, 2H), 5.16-5.21 (complex, 2H), 5.28 (s, 2H, H-1 of Rha), 5.52 (s, 1H, PhCH), 6.90 (dd, 4H, PhOMe), 7.31-7.49 (complex, 5H, Ph); $^{13}$C-NMR (CDCl$_3$, 100 MHz) δ 14.3, 17.3, 20.4, 20.7, 209×3, 21.0, 21.1, 55.8, 60.5, 62.0, 66.3, 66.9, 68.3, 68.7, 69.3, 69.4, 70.7, 71.6, 71.9, 72.9, 78.9, 81.0, 97.7, 99.3, 100.7, 101.6, 114.8, 118.4, 126.2, 128.4, 129.4, 137.1, 150.7, 155.8, 169.4, 169.5, 170.0, 170.2, 170.4, 170.5, 170.8, 171.2.

Compound 11 (627 mg, 0.642 mmol) was dissolved in ethanol (3 mL) and THF (3 mL), added with palladium hydroxide (1.0 g) at room temperature, and agitated in an hydrogen atmosphere at room temperature for two hours, After confirming the completion of the reaction by TLC (ethyl acetate/hexane=2/1, Rf value=0.2), palladium hydroxide was removed by filtration, and the filtrate was concentrated wider a reduced pressure. Subsequently, the resultant was dissolved in pyridine (6.4 mL), added with acetic anhydride (182 µL, 1.93 mmol) at room temperature, and agitated at room temperature for 18 hours. After confirming the completion of the reaction by TLC (ethyl acetate/hexane=2/1, Rf value=0.7), azeotropic distillation with toluene (20 mL) was repeated for three times. Subsequently, the resultant was concentrated under a reduced pressure. The resulting syrup was dissolved in acetonitrile (4 mL) and water (2 mL), added with cerium ammonium nitrate (1.0 g, 1.87 mmol) at room temperature, and agitated at room temperature for 30 minutes. After confirming the completion of the reaction by TLC (toluene/ethyl acetate=1/1, Rf value=0.3), the resultant was diluted with ethyl acetate, the organic layer was washed with water and a saturated aqueous sodium hydrogen carbonate solution, and dried with magnesium sulfate. Magnesium sulfate was removed by filtration, and the resultant was concentrated wider a reduced pressure. The resulting syrup was subjected to silica gel column chromatography and an eluate (toluene/ethyl acetate=1/1) was used to give Compound 13 (468 mg, 84%, 3 steps).

[Compound 13]

$^1$H-NMR (CDCl$_3$, 400 MHz) δ 1.18 (d, J=6.4 Hz, 1H, H-6 of Rha), 1.93-2.19 (complex, 27H, OAc), 3.60 (t, 1.6H, H-2β), 3.68 (m, 1.2H, H-5H), 3.78 (m, 1.4H, H-5'β), 3.97 (t, 1H, H-3β), 4.03 (dd, 1H, H-6'β), 4.15 (m, 2.3H, H-6β, H-6β), 4.22 (m, 1.2H, H-5β of Rha), 4.43 (dd, 1.2H, H-6'β), 4.67 (d, J=7.6 Hz, 1H, H-1β), 4.77 (d, J=8.0 Hz, 1H, H-1'β), 4.82-4.91 (complex, 2.4H, H-4β, H-2'β), 5.06-5.14 (complex, 2.3H, H-4'β, H-4β of Rha), 5.16 (s, 1H, H-1 of Rha), 5.26-5.33 (complex, 2.4H, H-3'β, H-3β of Rha), 5.39 (m, 1.1H, H-2β of Rha); $^{13}$C-NMR (CDCl$_3$, 100 MHz) δ 17.3, 17.5, 20.6, 20.7×2, 20.8×3, 20.9×2, 21.6, 29.8, 31.1, 61.7, 61.8, 62.4, 67.4, 67.6, 67.9, 68.0, 68.1×2, 68.3, 68.8×2, 69.5, 69.9, 70.6×2, 71.5, 71.8, 71.9, 72.1, 72.3, 72.8, 73.0, 75.5, 79.9, 80.1, 80.5, 91.9, 95.8, 98.1, 98.9, 99.6, 99.8, 125.4, 128.4, 129.2, 169.1, 169.4, 169.5, 169.6, 169.7, 170.0×3, 170.1, 170.4, 170.5×2, 170.7.

(4) Synthesis of Compound 17

Scheme 13
Synthesis of Novel steviol glycoside 2 (Compound 17)

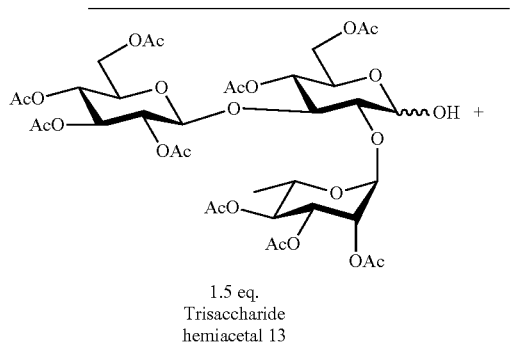

1.5 eq.
Trisaccharide hemiacetal 13

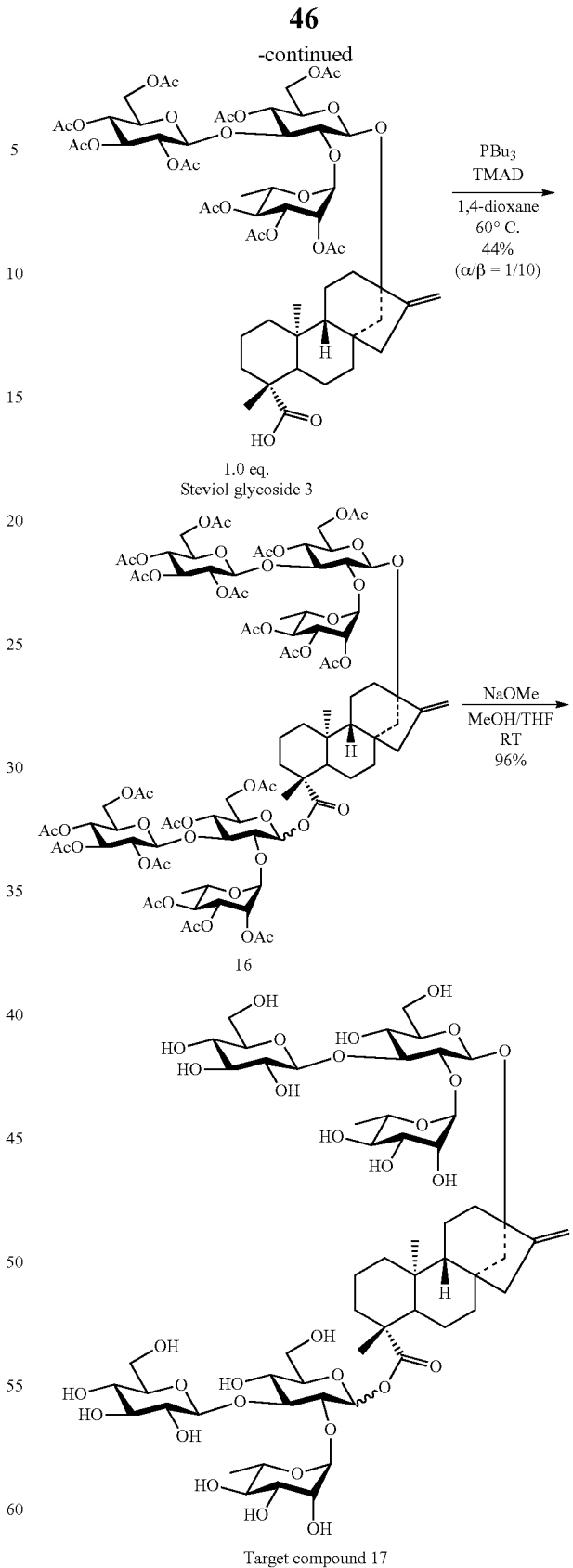

Target compound 17

As can be appreciated from Scheme 13, for synthesis of Compound 17, Compound 13 (468 mg, 0.540 mmol) and Compound 3 (420 mg, 0.360 mmol) were dissolved in 1,4-dioxane (18 mL), added with tributylphosphine (270 µL, 1.08 mmol) and 1,1'-azobis (N,N'-dimethylformamide) (TMAD) (186 mg, 1.08 mmol) at room temperature, and agitated at 60° C. for 6 hours. After confirming the completion of the reaction by TLC (toluene/ethyl acetate=1/1, Rf value=0.4), the resultant was diluted with ethyl acetate, the organic layer was washed with water, a saturated aqueous sodium hydrogen carbonate solution and saturated saline, and dried with magnesium sulfate. Magnesium sulfate was removed by filtration, and the resultant was concentrated under a reduced pressure. The resulting syrup was subjected to silica gel column chromatography, and an eluate (toluene/ethyl acetate=1.5/1) and (toluene/acetone=3/1) were used to give Compound 16 (320 mg, 44%, α/β=1/10).

[Compound 16]

$^1$H-NMR (CDCl$_3$, 400 MHz) δ 0.45-1.18 (complex, 8H), 1.28 (d, 3H, H-6 of Rham), 1.40-1.81 (complex, 20H), 1.81-2.35 (complex, 54H, OAc), 3.60 (m, 1.2H), 3.71-3.78 (complex, 3H), 3.81-3.91 (complex, 2.4H), 3.98-4.20 (complex, 10H), 4.40-4.50 (complex, 3.4H), 4.62 (d, J=8.0 Hz, 1.1H, H-1), 4.73 (d, J=8.0 Hz, 1H, H-1), 4.75-4.91 (complex, 7H), 4.96-5.12 (complex, 7H), 5.17 (s, 1H, H-1 of Rha), 5.21-5.31 (complex, 6H), 5.32 (s, 1H, H-1 of Rha), 5.38 (t, 1.1H), 5.60 (d, J=8.0 Hz, 1H, H-1β), 6.22 (d, J=3.0 Hz. 0.1H, H-1α); $^{13}$C-NMR (CDCl$_3$, 100 MHz) δ 16.7, 17.5, 20.5, 20.7×2, 20.8×2, 20.9×2, 21.0, 21.6, 29.0, 39.6, 42.5, 44.0, 53.9, 58.1, 61.7, 66.7, 67.6, 68.0, 68.1, 68.3, 68.5, 69.8, 70.2, 70.7, 71.2, 71.4, 71.8, 71.9, 72.2, 72.4, 72.8, 72.9, 75.2, 80.3, 81.4, 86.6, 92.2, 96.4, 96.9, 99.3, 99.8, 125.4, 128.4, 129.2, 138.0, 152.9, 169.0, 169.3, 169.5×2, 169.6×2, 169.8, 170.1×3, 170.2, 170.5, 170.6, 170.9×2, 174.7.

Compound 16 (300 mg, 0.149 mmol) was dissolved in methanol (2.0 mL) and THF (2.0 mL), added with sodium methoxide (0.5 M in MeOH) (0.3 mL, 0.149 mmol) at room temperature, and agitated at room temperature for 3 hours. After confirming the completion of the reaction by TLC (chloroform/methanol/water=5/4/1, Rf value=0.5), the resultant was concentrated under a reduced pressure. The resulting syrup was subjected to gel filtration column (GE Healthcare, Sephadex L11-20, ethanol) to give Compound 17 (188 mg, 96%, α/β=1/10). Subsequently, the β-form of Compound 17 was isolated by preparative HPLC (C18 YMC HPLC column, 20 mM aqueous ammonium acetate solution/90% acetonitrile/10% water=70/30-10/90, 45 minutes), and subjected to lyophilization. The structural analysis data of Compound 17 by nuclear magnetic resonance (NMR) method is shown in FIGS. 10-13.

[Compound 17 (the β-form)]

$^1$-NMR (pyridine-d5, 800 MHz δ 0.67, (m. 1H), 0.86 (m, 1H), 0.96 (m, 1H), 1.07 (m, 1H), 1.14 (s, 3H), 1.26 (M, 1H), 1.36 (m, 1H), 1.41 (m, 1H), 1.48 (s, 3H), 1.61 (m, 3H), 1.70 (m, 6H), 1.87-2.21 (complex, 11H), 2.46 (m, 1H), 2.57 (m, 1H), 3.63 (m, 1H), 3.85 (m, 1H), 3.95-4.09 (complex, 8H), 4.14-4.31 (complex, 14H), 4.33 (m, 1H), 4.45 (m, 2H), 4.55 (m, 3H), 4.78 (m, 1H), 4.82 (m, 1H), 4.86 (m, 1H), 4.98 (d, J=8.0 Hz, 1H), 5.05-5.11 (complex, 3H), 5.66 (s, 1H), 6.17 (d, J=8.0 Hz, 1H), 6.24 (s, 1H), 6.46 (s, 1H); $^{13}$C-NMR (pyridine-d5, 200 MHz) δ 17.0, 19.2, 20.1, 20.9, 22.3, 29.6, 37.8, 38.3, 39.9, 40.8, 41.9, 42.7, 43.7, 44.5, 48.4, 54.2, 58.4, 61.9, 62.4, 62.5, 69.1, 69.8×2, 70.5, 71.6, 71.7, 72.3, 72.4, 72.5×2, 73.9, 74.1, 75.2, 76.4, 76.5, 77.5, 78.3, 78.4 78.5, 78.8×2, 86.9, 88.8, 89.8, 93.8, 98.4, 101.8, 101.9, 104.4, 104.5, 105.3, 154.4, 176.0.

[α]$_D$=-44.5° (c 0.1, MeOH)

MALDI-TOF-MS m/z found [M+Na]$^+$ 1281.4, C$_{56}$H$_{90}$O$_{31}$ calcd for [M+Na]$^+$ 1281.5.

Figure 14:
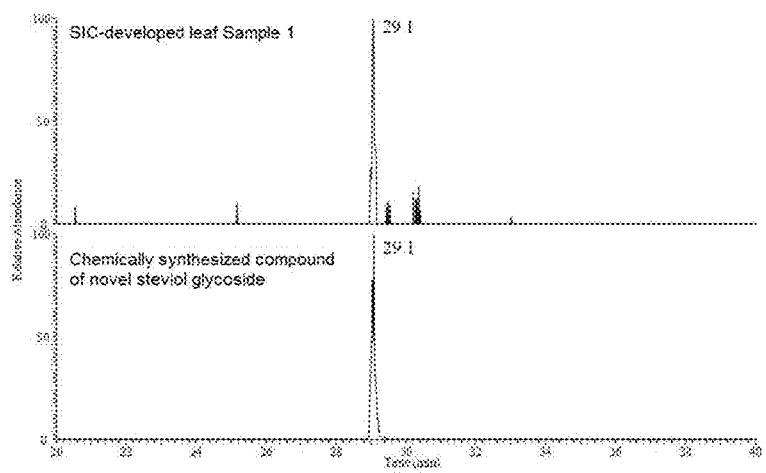
FIG. 14 illustrates a diagram showing extracted ion chromatograms of Novel steviol glycoside 1 (stevia leaf extract) and a chemically synthesized product (the β-form of Compound 15).
Figure 15:
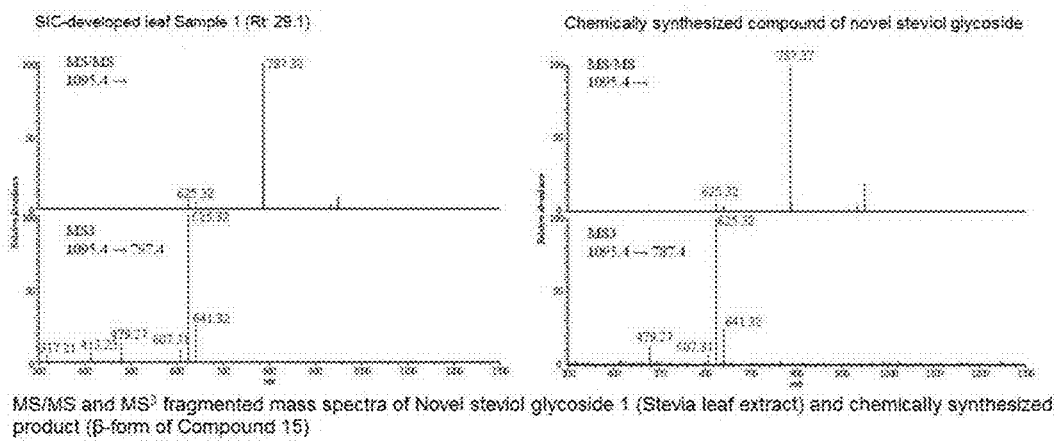
FIG. 15 illustrates Diagrams showing MS/MS and $MS^3$ fragmented mass spectra of Novel steviol glycoside 1 (stevia leaf extract) and a chemically synthesized product (the β-form of Compound 15).

(iii) Structural determination by matching with chemically synthesized standard product with respect to retention time and fragmented pattern from HPLC-high resolution MS/MS and MS$^3$ fragmentation The chemically synthesized product of Novel steviol glycoside 1 (the β-form of Compound 15) and stevia leaf liquid extracts were compared by HPLC-high resolution MS/MS and MS$^3$-fragmentation under the same conditions as (i). As a result, the peaks of the chemically synthesized product and the stevia leaf liquid extract were detected at the peak at the retention time of 29.1 minutes (FIG. 14). Moreover, they also matched in the respective MS/MS and MS$^3$ fragmented mass spectra (FIG. 15). From this result, Novel steviol glycoside 1 obtained from the liquid extract of the plant was confirmed to have the same structure as the β-form of Compound 15.

Figure 16:
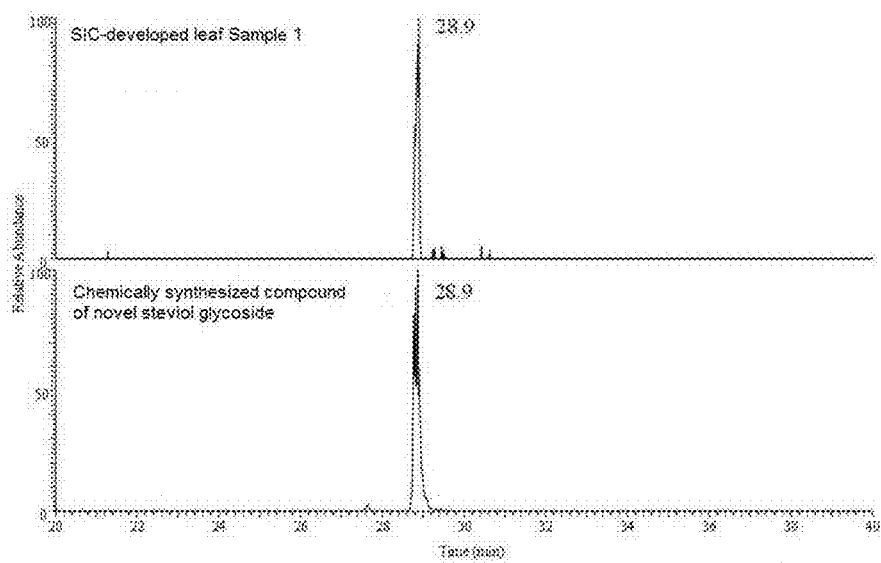
FIG. 16 illustrates a diagram showing extracted ion chromatograms of Novel steviol glycoside 2 (stevia leaf extract) and a chemically synthesized product (the β-form of Compound 17).
Figure 17:
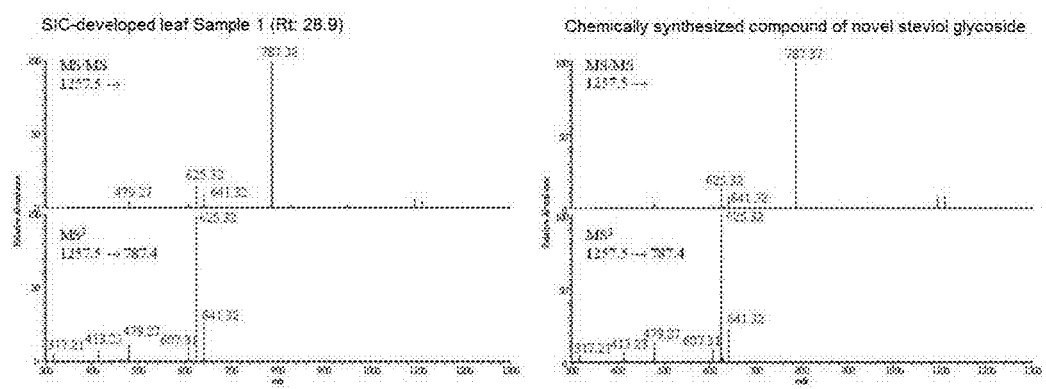
FIG. 17 illustrates Diagrams showing MS/MS and $MS^3$ fragmented mass spectra of Novel steviol glycoside 2 (stevia leaf extract) and a chemically synthesized product (the β-form of Compound 17).

In addition, the chemically synthesized product of Novel steviol glycoside 2 (the β-form of Compound 17) and the stevia leaf liquid extract were compared by HPLC-high resolution MS/MS and MS$^3$-fragmentation under the same conditions as (i). As a result, the peaks of the chemically synthesized product and the stevia leaf liquid extract were detected at the peak at the retention time of 28.9 minutes (FIG. 16). Moreover, they also matched in the respective MS/MS and MS$^3$ fragmented mass spectra (FIG. 17). From this result, Novel steviol glycoside 2 obtained from the liquid extract of the plant was confirmed to have the same structure as the β-form of Compound 17.

[Biosynthesis of Novel Steviol Glycoside]

A novel steviol glycoside was generated from steviol in yeast. First, a yeast that could coexpress four types of stevia-derived glycosylated enzyme genes UGT85C2, UGT91D2, UGT74G1 and UGT76G1 and *Arabidopsis thaliana*-derived UDP-rhamnose synthase gene AtRHM2 was bred.

Unless otherwise specified, the molecular biological processes employed in this example followed the methods described in Molecular Cloning (Sambrook et al., Cold Spring Harbour Laboratory Press, 2001).

In order to clone the four stevia-derived glycosylated enzyme genes, the following primer sets were synthesized to perform PCR using cDNA prepared from stevia leaves as a template.

```
Primer set for UGT85C2 gene amplification
CACC-NdeI-SrUGT85C2-Fw (NdeI-recognizing site
underlined):
                                      (SEQ ID NO: 12)
5'-CACCCATATGGATGCAATGGCTACAACTGAGAA-3'

BglII-SrUGT85C2-Rv (BglII-recognizing site
underlined):
                                      (SEQ ID NO: 13)
5'-AGATCTCTAGTTTCTTGCTAGCACGGTGATTT-3'

Primer set for UGT91D2 gene amplification
SrUGT91D2-pET15b-FW
                                      (SEQ ID NO: 35)
5'-TGCCGCGCGGCAGCCATATGTACAACGTTACTTATCATC-3'

SrUGT91D2-pET15b-RV
                                      (SEQ ID NO: 36)
5'-GTTAGCAGCCGGATCCTTAACTCTCATGATCGATGGCAA-3'

Primer set for UGT74G1 gene amplification
CACC-NdeI-SrUGT74G1-Fw (NdeI-recognizing site
underlined):
                                      (SEQ ID NO: 14)
5'-CACCCATATGGCGGAACAACAAAAGATCAAGAAAT-3'
```

-continued

BamHI-SrUGT74G1-Rv (BamHI-recognizing site
underlined):
(SEQ ID NO: 15)
5'-GGATCCTTAAGCCTTAATTAGCTCACTTACAAATT-3'

Primer set for UGT76G1 gene amplification
CACC-NdeI-SrUGT76G1-Fw (NdeI-recognizing site
underlined):
(SEQ ID NO: 16)
5'-CACCCATATGGAAAATAAAACGGAGACCA-3'

BamHI-SrUGT76G1-RV (BamHI-recognizing site
underlined):
(SEQ ID NO: 17)
5'-GGATCCTTACAACGATGAAATGTAAGAAACTA-3'

Stevia leaf cDNA was obtained by extracting total RNA from stevia leaves using RNeasy Plant Mini kit (QIAGEN), and subjecting 0.5 µg of them to reverse transcription (RT) reaction using Random Oligo-dT primer.

The PCR reaction solution (50 µl) had the following composition: 1 µl of stevia leaf-derived cDNA, 1×KOD plus buffer (TOYOBO), 0.2 mM dNTPs, 0.4 pmol/µl of each primer, 1 mM MgSO$_4$ and 1U heat resistant KOD plus polymerase. PCR reaction consisted of reaction at 95° C. for 5 minutes, followed by amplification by a total of 30 cycles of reaction at 94° C. for 0.5 minutes. 50° C. for 0.5 minutes and 68° C. for 2 minutes. Each PCR product was subjected to electrophoresis with 0.8% agarose gel and ethidium bromide staining, by which an amplification band of nearly 1.4 kb in size was obtained as presumed from each template DNA.

This PCR product was subcloned into pENTR-TOPO Directional vector (Invitrogen) according to a method recommended by the manufacturer. DNA Sequencer model 3100 (Applied Biosystems) was used for sequencing by a primer walking process with a synthesized oligonucleatide primer, thereby confirming that all of the UGT genes of interest, namely, UGT85C2, UGT91D2, UGT74G1 and UGT76G1 were cloned.

Construction of Yeast Expression Vector

The following primer sets were designed to integrate these UGT genes and *Arabidopsis thaliana*-derived UDP-rhamnose synthase gene AtRHM2 Biol Chem 2007, Oka et. al) into a yeast expression vector.

SrUGT85C2 set
Bgl2-UGT85C2-F (BglII-recognizing site
underlined):
(SEQ ID NO: 18)
5'-ACAGATCTATGGAATGCAATGGCTACAACTGAGA-3'

Sal-UGT85C2-R (SalI-recognizing site underlined):
(SEQ ID NO: 19)
5'-TAGTCGACTAGTTTCTTGCTAGCACGGTGATTTC-3'

SrUGT91D2 set
NotI-UGT91DIL3-F (NotI-recognizing site
underlined):
(SEQ ID NO: 20)
5'-AAGCGGCCGCATGTACAACGTTACTTATCATCAAAATTCAAA-3'

Pac-UGT91D1L3-R (PacI-recognizing site
underlined):
(SEQ ID NO: 21)
5'-CGTTAATTAACTCTCATGATCGATGGCAACC-3'

SrUGT74G1 set
Not-UGT74G1-F (NotI-recognizing site underlined):
(SEQ ID NO: 22)
5'-AAGCGGCCGCATGGCGGAACAACAAAAGATCAAG-3'

-continued

Pac-UGT74G1-R (PacI-recognizing site underlined):
(SEQ ID NO: 23)
5'-CGTTAATTAAGCCTTAATTAGCTCACTTACAAATTCG-3'

SrUGT76G1 set
Bam-UGT76G1-F (BamHI-recognizing site underlined):
(SEQ ID NO: 24)
5'-AAGGATCCATGGAAAATAAAACGGAGACCACCG-3'

Sal-UGT76G1-R (SalI-recognizing site underlined):
(SEQ ID NO: 25)
5'-GCGTCGACTTACAACGATGAAATGTAAGAAACTAGAGACTCTAA-3'

AtRHM2 set
Bam-AtRHM2-F (BamHI-recognizing site underlined):
(SEQ ID NO: 26)
5'-GGATCCATGGATGATACTACGTATAAGCCAAAG-3'

Xho-AtRHM2-R (XhoI-recognizing site underlined):
(SEQ ID NO: 27)
5'-CTCGAGTTAGGTTCTCTTGTTTGGTTCAAAGA-3'

The combinations of templates and primers, namely, template UGT85C2 and SrUGT85C2 set, template UGT91D2 and SrUGT91D2 set, template UGT74G1 and SrUGT74G1 set, template UGT76G1 and SrUGT76G1 set, and template AtAHM2 and AtAHM2 set, were used for PCR amplification using heat resistant KOD DNA polymerase (TOYOBO) and introduction of the restriction enzyme sites at both ends of each ORF. The resulting DNA fragment was subcloned using Zero Blunt-TOPO PCR cloning kit (Invitrogen), and sequenced using DNA Sequencer model 3100 (Applied Biosystems) by a primer walking process with a synthesized oligonucleotide primer to confirm that each of the UGT genes of interest was cloned.

In order to allow expressions of the above-described genes in yeasts by using pESC yeast expression system (Stratagene), the following expression vectors were constructed.

(1) Construction of plasmid pESC-URA-UGT56

UGT85C2 was cleaved with restriction enzymes BglII and SalI, and linked to vector pESC-URA (Stratagene) that had been cleaved with restriction enzymes BamHI and SalI to give plasmid pESC-URA-UGT-5. This plasmid pESC-URA-UGT-5 was cleaved with restriction enzymes NotI and PacI while UGT91 D2 was also cleaved with restriction enzymes NotI and PacI. The resultants were linked to give pESC-URA-UGT56.

(2) Construction of plasmid pESC-HIS-UGT78

UGT76G1 was cleaved with restriction enzymes BamHI and SalI, and linked to vector pESC-HIS (Stratagene) that had been cleaved with the same restriction enzymes to give plasmid pESC-HIS-UGT-8. This plasmid pESC-HIS-UGT-8 was cleaved with restriction enzymes NotI and PacI while UGT74G1 was also cleaved with NotI and PacI. The resultants were linked to give pESC-HIS-UGT78.

(3) Construction of plasmid pESC-TRP-AtRHM2

AtAHM2 was cleaved with restriction enzymes BamHI and XhoI while vector pESC-TRP (Stratagene) was cleaved with the same restriction enzymes. The resultants were linked to give plasmid pESC-TRP-AtAHM2.

Transformation of Yeast

Plasmids shown in Table 2 were introduced into *Saccharomyces cerevisiae* YPH499 strain (ura3-52 lys2-801$^{amber}$ade2-101$^{ochre}$ trp-Δ63 his3-Δ200 leu2-Δ1 a) as a host by lithium acetate technique. As transformed strains, those that survived in a SC-Trp-Ura-His agar medium (6.7 g of yeast nitrogen base without amino acids, 20 g of glucose, 1.3 g of amino acid powder mix-Trp-Ura-His and 20 g of Bacto agar, per 1 L) were selected.

TABLE 2

| Transformed strain | Plasmids introduced | Genes introduced |
|---|---|---|
| A-5678 | pESC-URA-UGT-56 | SrUGT85C2, SrUGT91D2 |
|  | pESC-HIS-UGT-78 | SrUGT74G1, SrUGT76G1 |
|  | pESC-TRP-AtAHM2 | AtAHM2 |

Here, the amino acid powder mix-Trp-Ura-His was prepared by mixing adenine sulfate (2.5 g), L-arginine hydrochloride (1.2 g), L-aspartic acid (6.0 g), L-glutamic acid (6.0 g), L-leucine (3.6 g), L-lysine (1.8 g), L-methionine (1.2 g), L-phenylalanine (3.0 g), L-serine (22.5 g), L-threonine (12 g), L-tyrosine (1.8 g) and L-valine (9.0 g).

Induction and Analysis of Expression of Transgene

The resulting transformed strain was cultured as follows.

First, for preliminary culture, each transformed strain was seeded in 10 ml of a SC-Trp-Ura-His liquid medium (SC-Trp-Ura-His agar medium without Bacto agar) and shake cultured at 30° C. for a day. Subsequently, for main culture, 1 ml of the preliminary culture solution was seeded into 10 ml of SG-Trp-Ura-His liquid medium (6.7 g of yeast nitrogen base without amino acids, 2.0 g of galactose and 1.3 g of amino acid powder mix-Trp-Ura-His, per 1 L) and shake cultured at 30° C. for two days.

In order to confirm whether or not the introduced gene was expressed in the transformed strain, cells were harvested from the culture solution to purify total RNA with RNeasy Mini Kit.

With 1 μg of total RNA, cDNA was synthesized using SuperScript II reverse transcriptase (Thermo Fischer Scientific) and random hexamer as a primer.

In order to confirm expression of the transgene, the following primers were prepared.

```
For confirming expression of UGT85C2
UGT85C2-r1:
                                      (SEQ ID NO: 28)
5'-CAAGTCCCCAACCAAATTCCGT-3'

For confirming expression of UGT91D2
UGT91D1L3-r1:
                                      (SEQ ID NO: 29)
5'-CACGAACCCGTCTGGCAACTC-3'

For confirming expression of UGT74G1
UGT74G1-r1:
                                      (SEQ ID NO: 30)
5'-CCCGTGTGATTTCTTCCACTTGTTC-3'

For confirming expression of UGT76G1
UGT76G1-r1:
                                      (SEQ ID NO: 31)
5'-CAAGAACCCATCTGGCAACGG-3'

For confirming expression of AtAHM2
AtAHM2-r1
                                      (SEQ ID NO: 32)
5'-GCTTTGTCACCAGAATCACCATT-3'

GAL10p region (promoter region)
PGAL10-f3:
                                      (SEQ ID NO: 33)
5'-GATTATTAAACTTCTTTGCGTCCATCCA-3'

GAL1p region (promoter region)
PGAL1-f3:
                                      (SEQ ID NO: 34)
5'-CCTCTATACTTTAACGTCAAGGAGAAAAAACC-3'
```

Expression of each transgene was confirmed by performing PCR by using ExTaq (Taraka Bio) with the following combination of primers and the previously synthesized cDNA as a template and subjecting the resulting product to agarose gel electrophoresis.

```
UGT85C2:
                                      (SEQ ID NO: 28)
UGT85C-r1
and
                                      (SEQ ID NO: 34)
PGAL1-f3

UGT91D2 or UGT9ID2L3:
                                      (SEQ ID NO: 29)
UGT91D1L3-r1
and
                                      (SEQ ID NO: 33)
PGAL10-f3

UGT74G1:
                                      (SEQ ID NO: 30)
UGT74G1-r1
and
                                      (SEQ ID NO: 34)
PGAL1-f3

UGT76G1:
                                      (SEQ ID NO: 31)
UGT76G1-r1
and
                                      (SEQ ID NO: 33)
PGAL10-f3

AtAHM2:
                                      (SEQ ID NO: 32)
AtAHM2-r1
and
                                      (SEQ ID NO: 33)
PGAL10-f3
```

Accordingly, expression of the transgene in the transformed strain was confirmed.

Production of Novel Steviol Glycoside

Culturing was performed under the same conditions as described above except that 0.5 μg or 2 μg of steviol (ChromaDex Inc.) was added to the liquid medium for the main culture per 1 ml of the medium. After culturing, the culture solution was separated into supernatant and cells by centrifugation. The culture supernatant was washed with acetonitrile, then subjected to a water-equilibrated Sep-Pak C18 column, washed with 20% acetonitrile, eluted with 80% acetonitrile, dried to solidify, and then dissolved in a small amount of 80% acetonitrile to prepare a glycoside sample. This glycoside sample was subjected to the following analysis.

Analysis by LC-MS

An analysis by LC-MS was carried out as described in the example under "Isolation of novel steviol glycoside".

Figure 18:
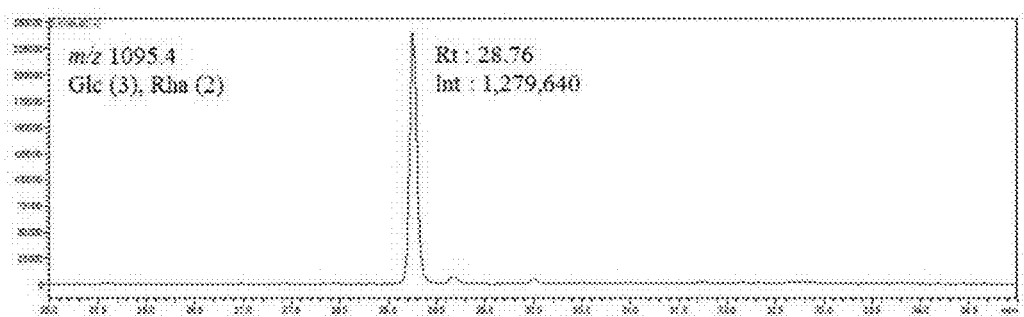
FIG. 18 illustrates a diagram showing a selected ion chromatogram of a sample obtained by biosynthesis at m/z of 1095.4.
Figure 19:
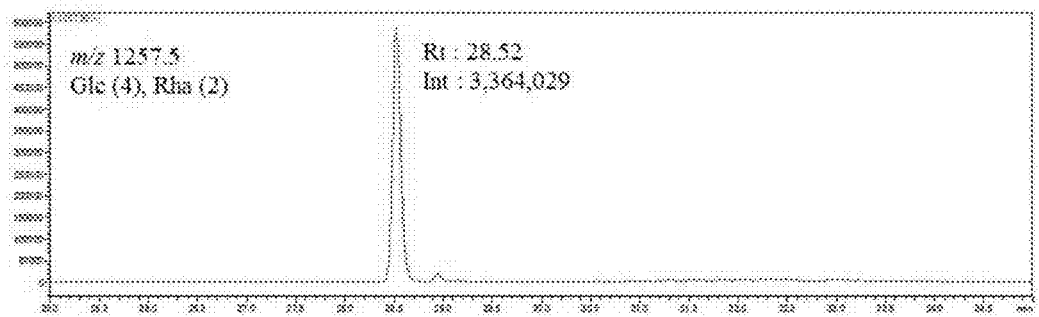
FIG. 19 illustrates a diagram showing a selected ion chromatogram of a sample obtained by biosynthesis at m/z of 1257.5.

The results are shown in FIGS. 18 and 19. Generation of Novel steviol glycosides 1 and 2 was confirmed in A-5678 strain. These results corresponded with the steviol glycosides resulting from the above-described chemical synthesis.

Evaluation of sweetness level of novel steviol glycoside

In order to evaluate the sweetness level of the novel steviol glycoside, samples were prepared by adding sucrose to pure water to give Brix of 0.5 to 3 in 0.5 increments. A sample was prepared by adding Compound 17 having the same structure as Novel steviol glycoside 2 to pure water to 1,700 ppm. Here, the ratio of the α-form and the β-form contained in Compound 17 was 1:10 (α:β, molar ratio).

Evaluation was conducted by selecting the sucrose-added sample having a sweetness intensity equivalent to that of the sample added with the novel steviol glycoside, where sensory evaluation was conducted by panelists trained about sensory attributes of sweeteners (5 members). As a result, the sample prepared by adding Novel glycoside 2 was found to have sweetness equivalent to that of the sucrose-added sample with Brix of 1. Therefore, the novel steviol glycoside of the invention was found to have a sweetness level of 14.7 with respect to sucrose. Although an accurate sweetness level was not acquired for Novel steviol glycoside 1 since it did not dissolve in water sufficiently, Novel steviol glycoside 1 was also confirmed to have sweetness as will be described below Sensory Evaluation of Novel Steviol Glycoside (Compound 17)

Figure 20:
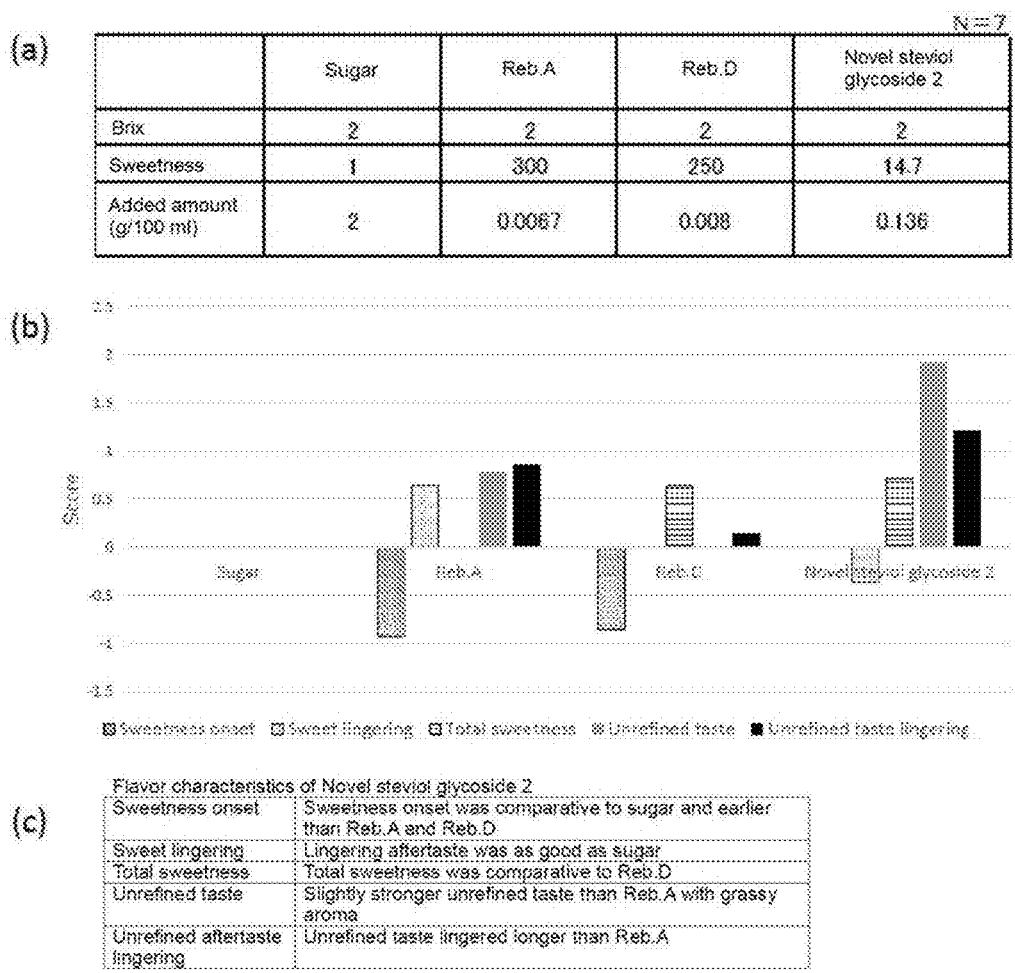
FIG. 20 illustrates Diagrams showing results of sensory evaluations for comparison of the novel steviol glycoside with rebaudioside A and rebaudioside D.

In order to evaluate the taste quality of various steviol glycosides, Reb.A, Reb.D and Compound 17 having the same structure as Novel steviol glycoside 2 were added to pure water at amounts indicated in FIG. 20 to prepare beverage samples. All of the beverage samples were adjusted to have final Brix of 2 in terms of sucrose, provided that the sweetness levels were Reb.A: 300, Reb.D: 250 and Novel glycoside 2 (Compound 17): 14.7.

The resulting beverage samples were subjected to sensory evaluation for rating attributes, namely, sweetness onset, sweet lingering, total sweetness, unrefined taste, and unrefined taste lingering. Unrefined taste as used herein refers to undesirable flavor other than sweetness such as bitterness and astringency. Panelists trained about sensory attributes of sweeteners (7 members: Suntory Beverage and Food Ltd.) evaluated based on the following evaluation criteria. Very weak (−3), weak (−2), slightly weak (−1), normal (0), slightly strong (+1), strong (+2) and very strong (+3). The results are shown in FIG. 20. The evaluation scores shown in the diagram are the average scores of the scores from the 7 panelists.

As a result of the sensory evaluation, Compound 17 having the same structure as Novel steviol glycoside 2 was found to have faster sweetness onset than the conventional sweeteners Reb.A and Reb.D and sweet lingering as good as sugar. It was also found to have total sweetness comparative to Reb.D.

Evaluation of Flavors of Novel Steviol Glycosides (Compounds 15 and 17) in Powder Forms Flavors of Novel steviol glycosides 1 and 2 in powder forms were evaluated. Specifically, Compounds 15 (corresponding to Novel steviol glycoside 1) and 17 (corresponding to Novel steviol glycoside 2) obtained by chemical syntheses were subjected to high performance liquid chromatography (HPLC) to isolate only the β-form, which was made into a powder form and subjected to flavor evaluation. Panelists trained about sensory attributes of sweeteners members: Suntory Beverage and Food Ltd.) evaluated. The results are shown in Table 3.

TABLE 3

Results from evaluating flavors of novel steviol glycosides (only β-form) in powder forms

| | Presence of sweetness | Flavor characteristics |
|---|---|---|
| Novel steviol glycoside 1 (Compound 15) | Present | Sweetness level was weaker than Novel steviol glycoside 2 Lingering aftertaste was stronger than Steviol glycoside 2, but with good finish |
| Novel steviol glycoside 2 (Compound 17) | Present | Flavor resembled the mixture No bitterness |

From the above results, both of Novel steviol glycosides 1 and 2 had sweetness and were found to be useful as sweeteners. Moreover, both glycosides had less undesirable flavor such as bitterness. Compound 17 had a flavor that resembled a. mixture of α- and β-forms used for evaluating the sweetness level.

The invention claimed is:

1. A food or beverage comprising a compound represented by Formula (13):

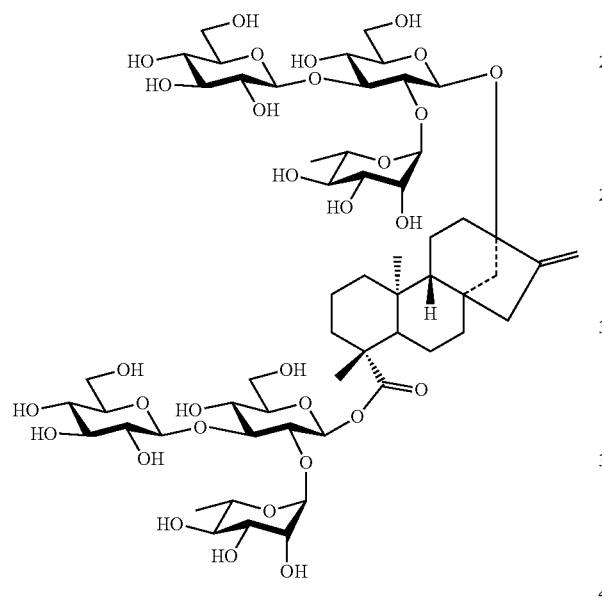

(13)

or a salt or a hydrate thereof, wherein the food or beverage further comprises one or more types of steviol glycosides selected from the group consisting of rebaudioside A, rebaudioside B, rebaudioside C, rebaudioside D, rebaudioside M, dulcoside A, and stevioside, and wherein the composition ratio of the compound or salt or a hydrate thereof and the other steviol glycoside is 0.01:9.99-6:4 in a mass ratio.

2. The food or beverage according to claim 1, further comprising one or more types of steviol glycosides selected from the group consisting of rebaudioside A and rebaudioside D.

3. The food or beverage according to claim 1, wherein the amount of the compound or a salt or a hydrate thereof is 0.0004%-0.8% based on the total weight of the food or beverage.

* * * * *

SEQUENCE LISTING

```
<160> NUMBER OF SEQ ID NOS: 36

<210> SEQ ID NO 1
<211> LENGTH: 1446
<212> TYPE: DNA
<213> ORGANISM: Stevia rebaudiana
<220> FEATURE:
<221> NAME/KEY: CDS
<222> LOCATION: (1)..(1446)

<400> SEQUENCE: 1 atg gat gca atg gct aca act gag aag aaa cca cac gtc atc ttc ata    48
Met Asp Ala Met Ala Thr Thr Glu Lys Lys Pro His Val Ile Phe Ile
1               5                   10                  15 cca ttt cca gca caa agc cac att aaa gcc atg ctc aaa cta gca caa    96
Pro Phe Pro Ala Gln Ser His Ile Lys Ala Met Leu Lys Leu Ala Gln
                20                  25                  30 ctt ctc cac cac aaa gga ctc cag ata acc ttc gtc aac acc gac ttc   144
Leu Leu His His Lys Gly Leu Gln Ile Thr Phe Val Asn Thr Asp Phe
            35                  40                  45
```

-continued

| | | |
|---|---|---|
| atc cac aac cag ttt ctt gaa tca tcg ggc cca cat tgt ttg gac ggt<br>Ile His Asn Gln Phe Leu Glu Ser Ser Gly Pro His Cys Leu Asp Gly<br>50           55              60 | | 192 |
| tca ccg ggt ttc cgg ttc gaa acc atc ccg gat ggt gtt tct cac agt<br>Ser Pro Gly Phe Arg Phe Glu Thr Ile Pro Asp Gly Val Ser His Ser<br>65              70              75              80 | | 240 |
| ccg gaa gcg agc atc cca atc aga gaa tca ctc ttg aga tcc att gaa<br>Pro Glu Ala Ser Ile Pro Ile Arg Glu Ser Leu Leu Arg Ser Ile Glu<br>              85              90              95 | | 288 |
| acc aac ttc ttg gat cgt ttc att gat ctt gta acc aaa ctt ccg gat<br>Thr Asn Phe Leu Asp Arg Phe Ile Asp Leu Val Thr Lys Leu Pro Asp<br>        100             105             110 | | 336 |
| cct ccg act tgt att atc tca gat ggg ttc ttg tcg gtt ttc aca att<br>Pro Pro Thr Cys Ile Ile Ser Asp Gly Phe Leu Ser Val Phe Thr Ile<br>        115             120             125 | | 384 |
| gac gct gca aaa aag ctt gga att ccg gtc atg atg tat tgg aca ctt<br>Asp Ala Ala Lys Lys Leu Gly Ile Pro Val Met Met Tyr Trp Thr Leu<br>130             135             140 | | 432 |
| gct gcc tgt ggg ttc atg ggt ttt tac cat att cat tct ctc att gag<br>Ala Ala Cys Gly Phe Met Gly Phe Tyr His Ile His Ser Leu Ile Glu<br>145             150             155             160 | | 480 |
| aaa gga ttt gca cca ctt aaa gat gca agt tac ttg aca aat ggg tat<br>Lys Gly Phe Ala Pro Leu Lys Asp Ala Ser Tyr Leu Thr Asn Gly Tyr<br>        165             170             175 | | 528 |
| ttg gac acc gtc att gat tgg gtt ccg gga atg gaa ggc atc cgt ctc<br>Leu Asp Thr Val Ile Asp Trp Val Pro Gly Met Glu Gly Ile Arg Leu<br>        180             185             190 | | 576 |
| aag gat ttc ccg ctg gac tgg agc act gac ctc aat gac aaa gtt ttg<br>Lys Asp Phe Pro Leu Asp Trp Ser Thr Asp Leu Asn Asp Lys Val Leu<br>        195             200             205 | | 624 |
| atg ttc act aca gaa gct cct caa agg tca cac aag gtt tca cat cat<br>Met Phe Thr Thr Glu Ala Pro Gln Arg Ser His Lys Val Ser His His<br>210             215             220 | | 672 |
| att ttc cac acg ttc gat gag ttg gag cct agt att ata aaa act ttg<br>Ile Phe His Thr Phe Asp Glu Leu Glu Pro Ser Ile Ile Lys Thr Leu<br>225             230             235             240 | | 720 |
| tca ttg agg tat aat cac att tac acc atc ggc cca ctg caa tta ctt<br>Ser Leu Arg Tyr Asn His Ile Tyr Thr Ile Gly Pro Leu Gln Leu Leu<br>        245             250             255 | | 768 |
| ctt gat caa ata ccc gaa gag aaa aag caa act gga att acg agt ctc<br>Leu Asp Gln Ile Pro Glu Glu Lys Lys Gln Thr Gly Ile Thr Ser Leu<br>        260             265             270 | | 816 |
| cat gga tac agt tta gta aaa gaa gaa cca gag tgt ttc cag tgg ctt<br>His Gly Tyr Ser Leu Val Lys Glu Glu Pro Glu Cys Phe Gln Trp Leu<br>        275             280             285 | | 864 |
| cag tct aaa gaa cca aat tcc gtc gtt tat gta aat ttt gga agt act<br>Gln Ser Lys Glu Pro Asn Ser Val Val Tyr Val Asn Phe Gly Ser Thr<br>290             295             300 | | 912 |
| aca gta atg tct tta gaa gac atg acg gaa ttt ggt tgg gga ctt gct<br>Thr Val Met Ser Leu Glu Asp Met Thr Glu Phe Gly Trp Gly Leu Ala<br>305             310             315             320 | | 960 |
| aat agc aac cat tat ttc ctt tgg atc atc cga tca aac ttg gtg ata<br>Asn Ser Asn His Tyr Phe Leu Trp Ile Ile Arg Ser Asn Leu Val Ile<br>        325             330             335 | | 1008 |
| ggg gaa aat gca gtt ttg ccc cct gaa ctt gag gaa cat ata aag aaa<br>Gly Glu Asn Ala Val Leu Pro Pro Glu Leu Glu Glu His Ile Lys Lys<br>        340             345             350 | | 1056 |
| aga ggc ttt att gct agc tgg tgt tca caa gaa aag gtc ttg aag cac<br>Arg Gly Phe Ile Ala Ser Trp Cys Ser Gln Glu Lys Val Leu Lys His<br>        355             360             365 | | 1104 |

```
cct tcg gtt gga ggg ttc ttg act cat tgt ggg tgg gga tcg acc atc      1152
Pro Ser Val Gly Gly Phe Leu Thr His Cys Gly Trp Gly Ser Thr Ile
    370                 375                 380 gag agc ttg tct gct ggg gtg cca atg ata tgc tgg cct tat tcg tgg      1200
Glu Ser Leu Ser Ala Gly Val Pro Met Ile Cys Trp Pro Tyr Ser Trp
385                 390                 395                 400 gac cag ctg acc aac tgt agg tat ata tgc aaa gaa tgg gag gtt ggg      1248
Asp Gln Leu Thr Asn Cys Arg Tyr Ile Cys Lys Glu Trp Glu Val Gly
                405                 410                 415 ctc gag atg gga acc aaa gtg aaa cga gat gaa gtc aag agg ctt gta      1296
Leu Glu Met Gly Thr Lys Val Lys Arg Asp Glu Val Lys Arg Leu Val
            420                 425                 430 caa gag ttg atg gga gaa gga ggt cac aaa atg agg aac aag gct aaa      1344
Gln Glu Leu Met Gly Glu Gly Gly His Lys Met Arg Asn Lys Ala Lys
        435                 440                 445 gat tgg aaa gaa aag gct cgc att gca ata gct cct aac ggt tca tct      1392
Asp Trp Lys Glu Lys Ala Arg Ile Ala Ile Ala Pro Asn Gly Ser Ser
    450                 455                 460 tct ttg aac ata gac aaa atg gtc aag gaa atc acc gtg cta gca aga      1440
Ser Leu Asn Ile Asp Lys Met Val Lys Glu Ile Thr Val Leu Ala Arg
465                 470                 475                 480 aac tag                                                              1446
Asn

<210> SEQ ID NO 2
<211> LENGTH: 481
<212> TYPE: PRT
<213> ORGANISM: Stevia rebaudiana

<400> SEQUENCE: 2

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ser Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205
```

```
Met Phe Thr Thr Glu Ala Pro Gln Arg Ser His Lys Val Ser His His
    210                 215                 220
Ile Phe His Thr Phe Asp Glu Leu Glu Pro Ser Ile Ile Lys Thr Leu
225                 230                 235                 240
Ser Leu Arg Tyr Asn His Ile Tyr Thr Ile Gly Pro Leu Gln Leu Leu
                245                 250                 255
Leu Asp Gln Ile Pro Glu Glu Lys Lys Gln Thr Gly Ile Thr Ser Leu
            260                 265                 270
His Gly Tyr Ser Leu Val Lys Glu Pro Glu Cys Phe Gln Trp Leu
        275                 280                 285
Gln Ser Lys Glu Pro Asn Ser Val Val Tyr Val Asn Phe Gly Ser Thr
    290                 295                 300
Thr Val Met Ser Leu Glu Asp Met Thr Glu Phe Gly Trp Gly Leu Ala
305                 310                 315                 320
Asn Ser Asn His Tyr Phe Leu Trp Ile Ile Arg Ser Asn Leu Val Ile
                325                 330                 335
Gly Glu Asn Ala Val Leu Pro Pro Glu Leu Glu His Ile Lys Lys
            340                 345                 350
Arg Gly Phe Ile Ala Ser Trp Cys Ser Gln Glu Lys Val Leu Lys His
        355                 360                 365
Pro Ser Val Gly Gly Phe Leu Thr His Cys Gly Trp Gly Ser Thr Ile
    370                 375                 380
Glu Ser Leu Ser Ala Gly Val Pro Met Ile Cys Trp Pro Tyr Ser Trp
385                 390                 395                 400
Asp Gln Leu Thr Asn Cys Arg Tyr Ile Cys Lys Glu Trp Glu Val Gly
                405                 410                 415
Leu Glu Met Gly Thr Lys Val Lys Arg Asp Glu Val Lys Arg Leu Val
            420                 425                 430
Gln Glu Leu Met Gly Glu Gly His Lys Met Arg Asn Lys Ala Lys
        435                 440                 445
Asp Trp Lys Glu Lys Ala Arg Ile Ala Ile Ala Pro Asn Gly Ser Ser
    450                 455                 460
Ser Leu Asn Ile Asp Lys Met Val Lys Glu Ile Thr Val Leu Ala Arg
465                 470                 475                 480
Asn

<210> SEQ ID NO 3
<211> LENGTH: 1383
<212> TYPE: DNA
<213> ORGANISM: Stevia rebaudiana
<220> FEATURE:
<221> NAME/KEY: CDS
<222> LOCATION: (1)..(1383)

<400> SEQUENCE: 3 atg gcg gaa caa caa aag atc aag aaa tca cca cac gtt cta ctc atc      48
Met Ala Glu Gln Gln Lys Ile Lys Lys Ser Pro His Val Leu Leu Ile
1               5                   10                  15 cca ttc cct tta caa ggc cat ata aac cct ttc atc cag ttt ggc aaa      96
Pro Phe Pro Leu Gln Gly His Ile Asn Pro Phe Ile Gln Phe Gly Lys
                20                  25                  30 cga tta atc tcc aaa ggt gtc aaa aca aca ctt gtt acc acc atc cac     144
Arg Leu Ile Ser Lys Gly Val Lys Thr Thr Leu Val Thr Thr Ile His
            35                  40                  45 acc tta aac tca acc cta aac cac agt aac acc acc acc tcc atc         192
Thr Leu Asn Ser Thr Leu Asn His Ser Asn Thr Thr Thr Ser Ile
        50                  55                  60
```

```
gaa atc caa gca att tcc gat ggt tgt gat gaa ggc ggt ttt atg agt    240
Glu Ile Gln Ala Ile Ser Asp Gly Cys Asp Glu Gly Gly Phe Met Ser
 65                  70                  75                  80 gca gga gaa tca tat ttg gaa aca ttc aaa caa gtt ggg tct aaa tca    288
Ala Gly Glu Ser Tyr Leu Glu Thr Phe Lys Gln Val Gly Ser Lys Ser
                 85                  90                  95 cta gct gac tta atc aag aag ctt caa agt gaa gga acc aca att gat    336
Leu Ala Asp Leu Ile Lys Lys Leu Gln Ser Glu Gly Thr Thr Ile Asp
            100                 105                 110 gca atc att tat gat tct atg act gaa tgg gtt tta gat gtt gca att    384
Ala Ile Ile Tyr Asp Ser Met Thr Glu Trp Val Leu Asp Val Ala Ile
        115                 120                 125 gag ttt gga atc gat ggt ggt tcg ttt ttc act caa gct tgt gtt gta    432
Glu Phe Gly Ile Asp Gly Gly Ser Phe Phe Thr Gln Ala Cys Val Val
    130                 135                 140 aac agc tta tat tat cat gtt cat aag ggt ttg att tct ttg cca ttg    480
Asn Ser Leu Tyr Tyr His Val His Lys Gly Leu Ile Ser Leu Pro Leu
145                 150                 155                 160 ggt gaa act gtt tcg gtt cct gga ttt cca gag ctt caa cgg tgg gag    528
Gly Glu Thr Val Ser Val Pro Gly Phe Pro Glu Leu Gln Arg Trp Glu
                165                 170                 175 aca ccg tta att ttg cag aat cat gag caa ata cag agc cct tgg tct    576
Thr Pro Leu Ile Leu Gln Asn His Glu Gln Ile Gln Ser Pro Trp Ser
            180                 185                 190 cag atg ttg ttt ggt cag ttt gct aat att gat caa gca cgt tgg gtc    624
Gln Met Leu Phe Gly Gln Phe Ala Asn Ile Asp Gln Ala Arg Trp Val
        195                 200                 205 ttc aca aat agt ttt tac aag ctc gag gaa gag gta ata gag tgg acg    672
Phe Thr Asn Ser Phe Tyr Lys Leu Glu Glu Glu Val Ile Glu Trp Thr
    210                 215                 220 aga aag ata tgg aac ttg aag gta atc ggg cca aca ctt cca tcc atg    720
Arg Lys Ile Trp Asn Leu Lys Val Ile Gly Pro Thr Leu Pro Ser Met
225                 230                 235                 240 tac ctt gac aaa cga ctt gat gat gat aaa gat aac gga ttt aat ctc    768
Tyr Leu Asp Lys Arg Leu Asp Asp Asp Lys Asp Asn Gly Phe Asn Leu
                245                 250                 255 tac aaa gca aac cat cat gag tgc atg aac tgg tta gac gat aag cca    816
Tyr Lys Ala Asn His His Glu Cys Met Asn Trp Leu Asp Asp Lys Pro
            260                 265                 270 aag gaa tca gtt gtt tac gta gca ttt ggt agc ctg gtg aaa cat gga    864
Lys Glu Ser Val Val Tyr Val Ala Phe Gly Ser Leu Val Lys His Gly
        275                 280                 285 ccc gaa caa gtg gaa gaa atc aca cgg gct tta ata gat agt gat gtc    912
Pro Glu Gln Val Glu Glu Ile Thr Arg Ala Leu Ile Asp Ser Asp Val
    290                 295                 300 aac ttc ttg tgg gtt atc aaa cat aaa gaa gag gga aag ctc cca gaa    960
Asn Phe Leu Trp Val Ile Lys His Lys Glu Glu Gly Lys Leu Pro Glu
305                 310                 315                 320 aat ctt tcg gaa gta ata aaa acc gga aag ggt ttg att gta gca tgg    1008
Asn Leu Ser Glu Val Ile Lys Thr Gly Lys Gly Leu Ile Val Ala Trp
                325                 330                 335 tgc aaa caa ttg gat gtg tta gca cac gaa tca gta gga tgc ttt gtt    1056
Cys Lys Gln Leu Asp Val Leu Ala His Glu Ser Val Gly Cys Phe Val
            340                 345                 350 aca cat tgt ggg ttc aac tca act ctt gaa gca ata agt ctt gga gtc    1104
Thr His Cys Gly Phe Asn Ser Thr Leu Glu Ala Ile Ser Leu Gly Val
        355                 360                 365 ccc gtt gtt gca atg cct caa ttt tcg gat caa act aca aat gcc aag    1152
Pro Val Val Ala Met Pro Gln Phe Ser Asp Gln Thr Thr Asn Ala Lys
```

```
                   370                 375                 380
ctt cta gat gaa att ttg ggt gtt gga gtt aga gtt aag gct gat gag        1200
Leu Leu Asp Glu Ile Leu Gly Val Gly Val Arg Val Lys Ala Asp Glu
385                 390                 395                 400 aat ggg ata gtg aga aga gga aat ctt gcg tca tgt att aag atg att        1248
Asn Gly Ile Val Arg Arg Gly Asn Leu Ala Ser Cys Ile Lys Met Ile
                405                 410                 415 atg gag gag gaa aga gga gta ata atc cga aag aat gcg gta aaa tgg        1296
Met Glu Glu Glu Arg Gly Val Ile Ile Arg Lys Asn Ala Val Lys Trp
            420                 425                 430 aag gat ttg gct aaa gta gcc gtt cat gaa ggt ggt agc tca gac aat        1344
Lys Asp Leu Ala Lys Val Ala Val His Glu Gly Gly Ser Ser Asp Asn
        435                 440                 445 gat att gtc gaa ttt gta agt gag cta att aag gct taa                    1383
Asp Ile Val Glu Phe Val Ser Glu Leu Ile Lys Ala
    450                 455                 460
```

<210> SEQ ID NO 4
<211> LENGTH: 460
<212> TYPE: PRT
<213> ORGANISM: Stevia rebaudiana

<400> SEQUENCE: 4

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
            85                  90                  95

Leu Ala Asp Leu Ile Lys Lys Leu Gln Ser Glu Gly Thr Thr Ile Asp
        100                 105                 110

Ala Ile Ile Tyr Asp Ser Met Thr Glu Trp Val Leu Asp Val Ala Ile
    115                 120                 125

Glu Phe Gly Ile Asp Gly Gly Ser Phe Phe Thr Gln Ala Cys Val Val
130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Glu Leu Gln Arg Trp Glu
            165                 170                 175

Thr Pro Leu Ile Leu Gln Asn His Glu Gln Ile Gln Ser Pro Trp Ser
        180                 185                 190

Gln Met Leu Phe Gly Gln Phe Ala Asn Ile Asp Gln Ala Arg Trp Val
    195                 200                 205

Phe Thr Asn Ser Phe Tyr Lys Leu Glu Glu Glu Val Ile Glu Trp Thr
210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
            245                 250                 255

Tyr Lys Ala Asn His His Glu Cys Met Asn Trp Leu Asp Asp Lys Pro
```

```
                  260                 265                 270
Lys Glu Ser Val Val Tyr Val Ala Phe Gly Ser Leu Val Lys His Gly
            275                 280                 285

Pro Glu Gln Val Glu Glu Ile Thr Arg Ala Leu Ile Asp Ser Asp Val
        290                 295                 300

Asn Phe Leu Trp Val Ile Lys His Lys Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
    370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
    450                 455                 460

<210> SEQ ID NO 5
<211> LENGTH: 1458
<212> TYPE: DNA
<213> ORGANISM: Stevia rebaudiana
<220> FEATURE:
<221> NAME/KEY: CDS
<222> LOCATION: (1)..(1458)

<400> SEQUENCE: 5 atg tac aac gtt act tat cat caa aat tca aaa gca atg gct acc agt      48
Met Tyr Asn Val Thr Tyr His Gln Asn Ser Lys Ala Met Ala Thr Ser
1               5                   10                  15 gac tcc ata gtt gac gac cgt aag cag ctt cat gtt gcg acg ttc cca      96
Asp Ser Ile Val Asp Asp Arg Lys Gln Leu His Val Ala Thr Phe Pro
                20                  25                  30 tgg ctt gct ttc ggt cac atc ctc cct tac ctt cag ctt tcg aaa ttg     144
Trp Leu Ala Phe Gly His Ile Leu Pro Tyr Leu Gln Leu Ser Lys Leu
            35                  40                  45 ata gct gaa aag ggt cac aaa gtc tcg ttt ctt tct acc acc aga aac     192
Ile Ala Glu Lys Gly His Lys Val Ser Phe Leu Ser Thr Thr Arg Asn
        50                  55                  60 att caa cgt ctc tct tct cat atc tcg cca ctc ata aat gtt gtt caa     240
Ile Gln Arg Leu Ser Ser His Ile Ser Pro Leu Ile Asn Val Val Gln
65                  70                  75                  80 ctc aca ctt cca cgt gtc caa gag ctg ccg gag gat gca gag gcg acc     288
Leu Thr Leu Pro Arg Val Gln Glu Leu Pro Glu Asp Ala Glu Ala Thr
                85                  90                  95 act gac gtc cac cct gaa gat att cca tat ctc aag aag gct tct gat     336
Thr Asp Val His Pro Glu Asp Ile Pro Tyr Leu Lys Lys Ala Ser Asp
                100                 105                 110 ggt ctt caa ccg gag gtc acc cgg ttt cta gaa caa cac tct ccg gac     384
Gly Leu Gln Pro Glu Val Thr Arg Phe Leu Glu Gln His Ser Pro Asp
            115                 120                 125
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 115 |     |     |     | 120 |     |     |     |     | 125 |     |     |     |     |     |      |
| tgg | att | att | tat | gat | tat | act | cac | tac | tgg | ttg | cca | tcc | atc | gcg | gct | 432  |
| Trp | Ile | Ile | Tyr | Asp | Tyr | Thr | His | Tyr | Trp | Leu | Pro | Ser | Ile | Ala | Ala |      |
|     | 130 |     |     |     |     | 135 |     |     |     |     | 140 |     |     |     |     |      |
| agc | ctc | ggt | atc | tca | cga | gcc | cac | ttc | tcc | gtc | acc | act | cca | tgg | gcc | 480  |
| Ser | Leu | Gly | Ile | Ser | Arg | Ala | His | Phe | Ser | Val | Thr | Thr | Pro | Trp | Ala |      |
| 145 |     |     |     |     | 150 |     |     |     |     | 155 |     |     |     |     | 160 |      |
| att | gct | tat | atg | gga | ccc | tca | gct | gac | gcc | atg | ata | aat | ggt | tca | gat | 528  |
| Ile | Ala | Tyr | Met | Gly | Pro | Ser | Ala | Asp | Ala | Met | Ile | Asn | Gly | Ser | Asp |      |
|     |     |     |     | 165 |     |     |     |     | 170 |     |     |     |     | 175 |     |      |
| ggt | cga | acc | acg | gtt | gag | gat | ctc | acg | aca | ccg | ccc | aag | tgg | ttt | ccc | 576  |
| Gly | Arg | Thr | Thr | Val | Glu | Asp | Leu | Thr | Thr | Pro | Pro | Lys | Trp | Phe | Pro |      |
|     |     |     | 180 |     |     |     |     | 185 |     |     |     |     | 190 |     |     |      |
| ttt | ccg | acc | aaa | gta | tgc | tgg | cgg | aag | cat | gat | ctt | gcc | cga | ctg | gtg | 624  |
| Phe | Pro | Thr | Lys | Val | Cys | Trp | Arg | Lys | His | Asp | Leu | Ala | Arg | Leu | Val |      |
|     |     | 195 |     |     |     |     | 200 |     |     |     |     | 205 |     |     |     |      |
| cct | tac | aaa | gct | ccg | ggg | ata | tct | gat | gga | tac | cgt | atg | ggg | ctg | gtt | 672  |
| Pro | Tyr | Lys | Ala | Pro | Gly | Ile | Ser | Asp | Gly | Tyr | Arg | Met | Gly | Leu | Val |      |
|     | 210 |     |     |     |     | 215 |     |     |     |     | 220 |     |     |     |     |      |
| ctt | aag | gga | tct | gat | tgt | ttg | ctt | tcc | aaa | tgt | tac | cat | gag | ttt | gga | 720  |
| Leu | Lys | Gly | Ser | Asp | Cys | Leu | Leu | Ser | Lys | Cys | Tyr | His | Glu | Phe | Gly |      |
| 225 |     |     |     |     | 230 |     |     |     |     | 235 |     |     |     |     | 240 |      |
| act | caa | tgg | cta | cct | ctt | ttg | gag | aca | cta | cac | caa | gta | ccg | gtg | gtt | 768  |
| Thr | Gln | Trp | Leu | Pro | Leu | Leu | Glu | Thr | Leu | His | Gln | Val | Pro | Val | Val |      |
|     |     |     |     | 245 |     |     |     |     | 250 |     |     |     |     | 255 |     |      |
| ccg | gtg | gga | tta | ctg | cca | ccg | gaa | ata | ccc | gga | gac | gag | aaa | gat | gaa | 816  |
| Pro | Val | Gly | Leu | Leu | Pro | Pro | Glu | Ile | Pro | Gly | Asp | Glu | Lys | Asp | Glu |      |
|     |     |     | 260 |     |     |     |     | 265 |     |     |     |     | 270 |     |     |      |
| aca | tgg | gtg | tca | atc | aag | aaa | tgg | ctc | gat | ggt | aaa | caa | aaa | ggc | agt | 864  |
| Thr | Trp | Val | Ser | Ile | Lys | Lys | Trp | Leu | Asp | Gly | Lys | Gln | Lys | Gly | Ser |      |
|     |     | 275 |     |     |     |     | 280 |     |     |     |     | 285 |     |     |     |      |
| gtg | gtg | tac | gtt | gca | tta | gga | agc | gag | gtt | ttg | gtg | agc | caa | acc | gag | 912  |
| Val | Val | Tyr | Val | Ala | Leu | Gly | Ser | Glu | Val | Leu | Val | Ser | Gln | Thr | Glu |      |
|     | 290 |     |     |     |     | 295 |     |     |     |     | 300 |     |     |     |     |      |
| gtt | gtt | gag | tta | gca | ttg | ggt | ctc | gag | ctt | tct | ggg | ttg | cca | ttt | gtt | 960  |
| Val | Val | Glu | Leu | Ala | Leu | Gly | Leu | Glu | Leu | Ser | Gly | Leu | Pro | Phe | Val |      |
| 305 |     |     |     |     | 310 |     |     |     |     | 315 |     |     |     |     | 320 |      |
| tgg | gct | tat | aga | aaa | cca | aaa | ggt | ccc | gcg | aag | tca | gac | tcg | gtg | gag | 1008 |
| Trp | Ala | Tyr | Arg | Lys | Pro | Lys | Gly | Pro | Ala | Lys | Ser | Asp | Ser | Val | Glu |      |
|     |     |     | 325 |     |     |     |     | 330 |     |     |     |     | 335 |     |     |      |
| ttg | cca | gac | ggg | ttc | gtg | gaa | cga | act | cgt | gac | cgt | ggg | ttg | gtc | tgg | 1056 |
| Leu | Pro | Asp | Gly | Phe | Val | Glu | Arg | Thr | Arg | Asp | Arg | Gly | Leu | Val | Trp |      |
|     |     | 340 |     |     |     |     | 345 |     |     |     |     | 350 |     |     |     |      |
| acg | agt | tgg | gca | cct | cag | tta | cga | ata | ctg | agc | cat | gag | tcg | gtt | tgt | 1104 |
| Thr | Ser | Trp | Ala | Pro | Gln | Leu | Arg | Ile | Leu | Ser | His | Glu | Ser | Val | Cys |      |
|     | 355 |     |     |     |     | 360 |     |     |     |     | 365 |     |     |     |     |      |
| ggt | ttc | ttg | act | cat | tgt | ggt | tct | gga | tca | att | gtg | gaa | ggg | cta | atg | 1152 |
| Gly | Phe | Leu | Thr | His | Cys | Gly | Ser | Gly | Ser | Ile | Val | Glu | Gly | Leu | Met |      |
|     | 370 |     |     |     |     | 375 |     |     |     |     | 380 |     |     |     |     |      |
| ttt | ggt | cac | cct | cta | atc | atg | cta | ccg | att | ttt | ggg | gac | caa | cct | ctg | 1200 |
| Phe | Gly | His | Pro | Leu | Ile | Met | Leu | Pro | Ile | Phe | Gly | Asp | Gln | Pro | Leu |      |
| 385 |     |     |     |     | 390 |     |     |     |     | 395 |     |     |     |     | 400 |      |
| aat | gct | cga | tta | ctg | gag | gac | aaa | cag | gtg | gga | atc | gag | ata | cca | aga | 1248 |
| Asn | Ala | Arg | Leu | Leu | Glu | Asp | Lys | Gln | Val | Gly | Ile | Glu | Ile | Pro | Arg |      |
|     |     |     |     | 405 |     |     |     |     | 410 |     |     |     |     | 415 |     |      |
| aat | gag | gaa | gat | ggt | tgc | ttg | acc | aag | gag | tcg | gtt | gct | aga | tca | ctg | 1296 |
| Asn | Glu | Glu | Asp | Gly | Cys | Leu | Thr | Lys | Glu | Ser | Val | Ala | Arg | Ser | Leu |      |
|     |     |     | 420 |     |     |     |     | 425 |     |     |     |     | 430 |     |     |      |
| agg | tcc | gtt | gtt | gtg | gaa | aaa | gaa | ggg | gag | atc | tac | aag | gcg | aac | gcg | 1344 |

```
Arg Ser Val Val Glu Lys Glu Gly Glu Ile Tyr Lys Ala Asn Ala
        435                 440                 445 agg gag ctg agt aaa atc tat aac gac act aag gtt gaa aaa gaa tat        1392
Arg Glu Leu Ser Lys Ile Tyr Asn Asp Thr Lys Val Glu Lys Glu Tyr
        450                 455                 460 gta agc caa ttc gta gac tat ttg gaa aag aat gcg cgt gcg gtt gcc        1440
Val Ser Gln Phe Val Asp Tyr Leu Glu Lys Asn Ala Arg Ala Val Ala
465                 470                 475                 480 atc gat cat gag agt taa                                                 1458
Ile Asp His Glu Ser
                485

<210> SEQ ID NO 6
<211> LENGTH: 485
<212> TYPE: PRT
<213> ORGANISM: Stevia rebaudiana

<400> SEQUENCE: 6

Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Tyr Leu Gln Leu Ser Lys Leu
        35                  40                  45

Ile Ala Glu Lys Gly His Lys Val Ser Phe Leu Ser Thr Thr Arg Asn
50                  55                  60

Ile Gln Arg Leu Ser Ser His Ile Ser Pro Leu Ile Asn Val Val Gln
65                  70                  75                  80

Leu Thr Leu Pro Arg Val Gln Glu Leu Pro Glu Asp Ala Glu Ala Thr
                85                  90                  95

Thr Asp Val His Pro Glu Asp Ile Pro Tyr Leu Lys Lys Ala Ser Asp
            100                 105                 110

Gly Leu Gln Pro Glu Val Thr Arg Phe Leu Glu Gln His Ser Pro Asp
        115                 120                 125

Trp Ile Ile Tyr Asp Tyr Thr His Tyr Trp Leu Pro Ser Ile Ala Ala
    130                 135                 140

Ser Leu Gly Ile Ser Arg Ala His Phe Ser Val Thr Thr Pro Trp Ala
145                 150                 155                 160

Ile Ala Tyr Met Gly Pro Ser Ala Asp Ala Met Ile Asn Gly Ser Asp
                165                 170                 175

Gly Arg Thr Thr Val Glu Asp Leu Thr Thr Pro Pro Lys Trp Phe Pro
            180                 185                 190

Phe Pro Thr Lys Val Cys Trp Arg Lys His Asp Leu Ala Arg Leu Val
        195                 200                 205

Pro Tyr Lys Ala Pro Gly Ile Ser Asp Gly Tyr Arg Met Gly Leu Val
    210                 215                 220

Leu Lys Gly Ser Asp Cys Leu Leu Ser Lys Cys Tyr His Glu Phe Gly
225                 230                 235                 240

Thr Gln Trp Leu Pro Leu Leu Glu Thr Leu His Gln Val Pro Val Val
                245                 250                 255

Pro Val Gly Leu Leu Pro Pro Glu Ile Pro Gly Asp Glu Lys Asp Glu
            260                 265                 270

Thr Trp Val Ser Ile Lys Lys Trp Leu Asp Gly Lys Gln Lys Gly Ser
        275                 280                 285

Val Val Tyr Val Ala Leu Gly Ser Glu Val Leu Val Ser Gln Thr Glu
    290                 295                 300
```

```
Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
                325                 330                 335

Leu Pro Asp Gly Phe Val Glu Arg Thr Arg Asp Arg Gly Leu Val Trp
            340                 345                 350

Thr Ser Trp Ala Pro Gln Leu Arg Ile Leu Ser His Glu Ser Val Cys
        355                 360                 365

Gly Phe Leu Thr His Cys Gly Ser Gly Ser Ile Val Glu Gly Leu Met
    370                 375                 380

Phe Gly His Pro Leu Ile Met Leu Pro Ile Phe Gly Asp Gln Pro Leu
385                 390                 395                 400

Asn Ala Arg Leu Leu Glu Asp Lys Gln Val Gly Ile Glu Ile Pro Arg
                405                 410                 415

Asn Glu Glu Asp Gly Cys Leu Thr Lys Glu Ser Val Ala Arg Ser Leu
            420                 425                 430

Arg Ser Val Val Glu Lys Glu Gly Glu Ile Tyr Lys Ala Asn Ala
        435                 440                 445

Arg Glu Leu Ser Lys Ile Tyr Asn Asp Thr Lys Val Glu Lys Glu Tyr
450                 455                 460

Val Ser Gln Phe Val Asp Tyr Leu Glu Lys Asn Ala Arg Ala Val Ala
465                 470                 475                 480

Ile Asp His Glu Ser
                485

<210> SEQ ID NO 7
<211> LENGTH: 1377
<212> TYPE: DNA
<213> ORGANISM: Stevia rebaudiana
<220> FEATURE:
<221> NAME/KEY: CDS
<222> LOCATION: (1)..(1377)

<400> SEQUENCE: 7 atg gaa aat aaa acg gag acc acc gtt cgc cgg cgc cgg aga ata ata        48
Met Glu Asn Lys Thr Glu Thr Thr Val Arg Arg Arg Arg Arg Ile Ile
1               5                   10                  15 tta ttc ccg gta cca ttt caa ggc cac att aac cca att ctt cag cta        96
Leu Phe Pro Val Pro Phe Gln Gly His Ile Asn Pro Ile Leu Gln Leu
            20                  25                  30 gcc aat gtg ttg tac tct aaa gga ttc agt atc acc atc ttt cac acc       144
Ala Asn Val Leu Tyr Ser Lys Gly Phe Ser Ile Thr Ile Phe His Thr
        35                  40                  45 aac ttc aac aaa ccc aaa aca tct aat tac cct cac ttc act ttc aga       192
Asn Phe Asn Lys Pro Lys Thr Ser Asn Tyr Pro His Phe Thr Phe Arg
    50                  55                  60 ttc atc ctc gac aac gac cca caa gac gaa cgc att tcc aat cta ccg       240
Phe Ile Leu Asp Asn Asp Pro Gln Asp Glu Arg Ile Ser Asn Leu Pro
65                  70                  75                  80 act cat ggt ccg ctc gct ggt atg cgg att ccg att atc aac gaa cac       288
Thr His Gly Pro Leu Ala Gly Met Arg Ile Pro Ile Ile Asn Glu His
                85                  90                  95 gga gct gac gaa tta cga cgc gaa ctg gaa ctg ttg atg tta gct tct       336
Gly Ala Asp Glu Leu Arg Arg Glu Leu Glu Leu Leu Met Leu Ala Ser
            100                 105                 110 gaa gaa gat gaa gag gta tcg tgt tta atc acg gat gct ctt tgg tac       384
Glu Glu Asp Glu Glu Val Ser Cys Leu Ile Thr Asp Ala Leu Trp Tyr
        115                 120                 125
```

| | | |
|---|---|---|
| ttc gcg caa tct gtt gct gac agt ctt aac ctc cga ccg ctt gtt ttg<br>Phe Ala Gln Ser Val Ala Asp Ser Leu Asn Leu Arg Pro Leu Val Leu<br>130                      135                        140 | | 432 |
| atg aca agc agc ttg ttt aat ttt cat gca cat gtt tca ctt cct cag<br>Met Thr Ser Ser Leu Phe Asn Phe His Ala His Val Ser Leu Pro Gln<br>145                      150                      155                      160 | | 480 |
| ttt gat gag ctt ggt tac ctc gat cct gat gac aaa acc cgt ttg gaa<br>Phe Asp Glu Leu Gly Tyr Leu Asp Pro Asp Asp Lys Thr Arg Leu Glu<br>                      165                      170                      175 | | 528 |
| gaa caa gcg agt ggg ttt cct atg cta aaa gtg aaa gac atc aag tct<br>Glu Gln Ala Ser Gly Phe Pro Met Leu Lys Val Lys Asp Ile Lys Ser<br>                      180                      185                      190 | | 576 |
| gcg tat tcg aac tgg caa ata ctc aaa gag ata tta ggg aag atg ata<br>Ala Tyr Ser Asn Trp Gln Ile Leu Lys Glu Ile Leu Gly Lys Met Ile<br>                      195                      200                      205 | | 624 |
| aaa caa aca aaa gca tct tca gga gtc atc tgg aac tca ttt aag gaa<br>Lys Gln Thr Lys Ala Ser Ser Gly Val Ile Trp Asn Ser Phe Lys Glu<br>210                      215                      220 | | 672 |
| ctc gaa gag tct gag ctc gaa act gtt atc cgt gag atc ccg gct cca<br>Leu Glu Glu Ser Glu Leu Glu Thr Val Ile Arg Glu Ile Pro Ala Pro<br>225                      230                      235                      240 | | 720 |
| agt ttc ttg ata cca ctc ccc aag cat ttg aca gcc tct tcc agc agc<br>Ser Phe Leu Ile Pro Leu Pro Lys His Leu Thr Ala Ser Ser Ser Ser<br>                      245                      250                      255 | | 768 |
| tta cta gac cac gat cga acc gtt ttt caa tgg tta gac caa caa ccg<br>Leu Leu Asp His Asp Arg Thr Val Phe Gln Trp Leu Asp Gln Gln Pro<br>                      260                      265                      270 | | 816 |
| cca agt tcg gta ctg tat gtt agt ttt ggt agt act agt gaa gtg gat<br>Pro Ser Ser Val Leu Tyr Val Ser Phe Gly Ser Thr Ser Glu Val Asp<br>                      275                      280                      285 | | 864 |
| gag aaa gat ttc ttg gaa ata gct cgt ggg ttg gtt gat agc aag cag<br>Glu Lys Asp Phe Leu Glu Ile Ala Arg Gly Leu Val Asp Ser Lys Gln<br>                      290                      295                      300 | | 912 |
| tcg ttt tta tgg gtg gtt cga cct ggg ttt gtc aag ggt tcg acg tgg<br>Ser Phe Leu Trp Val Val Arg Pro Gly Phe Val Lys Gly Ser Thr Trp<br>305                      310                      315                      320 | | 960 |
| gtc gaa ccg ttg cca gat ggg ttc ttg ggt gaa aga gga cgt att gtg<br>Val Glu Pro Leu Pro Asp Gly Phe Leu Gly Glu Arg Gly Arg Ile Val<br>                      325                      330                      335 | | 1008 |
| aaa tgg gtt cca cag caa gaa gtg cta gct cat gga gca ata ggc gca<br>Lys Trp Val Pro Gln Gln Glu Val Leu Ala His Gly Ala Ile Gly Ala<br>                      340                      345                      350 | | 1056 |
| ttc tgg act cat agc gga tgg aac tct acg ttg gaa agc gtt tgt gaa<br>Phe Trp Thr His Ser Gly Trp Asn Ser Thr Leu Glu Ser Val Cys Glu<br>                      355                      360                      365 | | 1104 |
| ggt gtt cct atg att ttc tcg gat ttt ggg ctc gat caa ccg ttg aat<br>Gly Val Pro Met Ile Phe Ser Asp Phe Gly Leu Asp Gln Pro Leu Asn<br>                      370                      375                      380 | | 1152 |
| gct aga tac atg agt gat gtt ttg aag gta ggg gtg tat ttg gaa aat<br>Ala Arg Tyr Met Ser Asp Val Leu Lys Val Gly Val Tyr Leu Glu Asn<br>385                      390                      395                      400 | | 1200 |
| ggg tgg gaa aga gga gag ata gca aat gca ata aga aga gtt atg gtg<br>Gly Trp Glu Arg Gly Glu Ile Ala Asn Ala Ile Arg Arg Val Met Val<br>                      405                      410                      415 | | 1248 |
| gat gaa gaa gga gaa tac att aga cag aat gca aga gtt ttg aaa caa<br>Asp Glu Glu Gly Glu Tyr Ile Arg Gln Asn Ala Arg Val Leu Lys Gln<br>                      420                      425                      430 | | 1296 |
| aag gca gat gtt tct ttg atg aag ggt ggt tcg tct tac gaa tca tta<br>Lys Ala Asp Val Ser Leu Met Lys Gly Gly Ser Ser Tyr Glu Ser Leu | | 1344 |

```
                435                 440                 445
gag tct cta gtt tct tac att tca tcg ttg taa                          1377
Glu Ser Leu Val Ser Tyr Ile Ser Ser Leu
    450                 455
```

<210> SEQ ID NO 8
<211> LENGTH: 458
<212> TYPE: PRT
<213> ORGANISM: Stevia rebaudiana

<400> SEQUENCE: 8

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Pro Leu Val Leu
130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350
```

```
Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
            370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Ser Ser Tyr Glu Ser Leu
            435                 440                 445

Glu Ser Leu Val Ser Tyr Ile Ser Ser Leu
            450                 455

<210> SEQ ID NO 9
<211> LENGTH: 2004
<212> TYPE: DNA
<213> ORGANISM: Arabidopsis thaliana
<220> FEATURE:
<221> NAME/KEY: CDS
<222> LOCATION: (1)..(2004)

<400> SEQUENCE: 9
```

| | | | | | | | | | | | | | | | | |
|---|---|---|---|---|---|---|---|---|---|---|---|---|---|---|---|---|
| atg | gat | gat | act | acg | tat | aag | cca | aag | aac | att | ctc | att | act | gga | gct | 48 |
| Met | Asp | Asp | Thr | Thr | Tyr | Lys | Pro | Lys | Asn | Ile | Leu | Ile | Thr | Gly | Ala | |
| 1 | | | | 5 | | | | | 10 | | | | | 15 | | |
| gct | gga | ttt | att | gct | tct | cat | gtt | gcc | aac | aga | tta | atc | cgt | aac | tat | 96 |
| Ala | Gly | Phe | Ile | Ala | Ser | His | Val | Ala | Asn | Arg | Leu | Ile | Arg | Asn | Tyr | |
| | | | 20 | | | | | 25 | | | | | 30 | | | |
| cct | gat | tac | aag | atc | gtt | gtt | ctt | gac | aag | ctt | gat | tac | tgt | tca | gat | 144 |
| Pro | Asp | Tyr | Lys | Ile | Val | Val | Leu | Asp | Lys | Leu | Asp | Tyr | Cys | Ser | Asp | |
| | | 35 | | | | | 40 | | | | | 45 | | | | |
| ctg | aag | aat | ctt | gat | cct | tct | ttt | tct | tca | cca | aat | ttc | aag | ttt | gtc | 192 |
| Leu | Lys | Asn | Leu | Asp | Pro | Ser | Phe | Ser | Ser | Pro | Asn | Phe | Lys | Phe | Val | |
| | 50 | | | | | 55 | | | | | 60 | | | | | |
| aaa | gga | gat | atc | gcg | agt | gat | gat | ctc | gtt | aac | tac | ctt | ctc | atc | act | 240 |
| Lys | Gly | Asp | Ile | Ala | Ser | Asp | Asp | Leu | Val | Asn | Tyr | Leu | Leu | Ile | Thr | |
| 65 | | | | | 70 | | | | | 75 | | | | | 80 | |
| gaa | aac | att | gat | acg | ata | atg | cat | ttt | gct | gct | caa | act | cat | gtt | gat | 288 |
| Glu | Asn | Ile | Asp | Thr | Ile | Met | His | Phe | Ala | Ala | Gln | Thr | His | Val | Asp | |
| | | | | 85 | | | | | 90 | | | | | 95 | | |
| aac | tct | ttt | ggt | aat | agc | ttt | gag | ttt | acc | aag | aac | aat | att | tat | ggt | 336 |
| Asn | Ser | Phe | Gly | Asn | Ser | Phe | Glu | Phe | Thr | Lys | Asn | Asn | Ile | Tyr | Gly | |
| | | | 100 | | | | | 105 | | | | | 110 | | | |
| act | cat | gtt | ctt | ttg | gaa | gcc | tgt | aaa | gtt | aca | gga | cag | atc | agg | agg | 384 |
| Thr | His | Val | Leu | Leu | Glu | Ala | Cys | Lys | Val | Thr | Gly | Gln | Ile | Arg | Arg | |
| | | | 115 | | | | | 120 | | | | | 125 | | | |
| ttt | atc | cat | gtg | agt | acc | gat | gaa | gtc | tat | gga | gaa | acc | gat | gag | gat | 432 |
| Phe | Ile | His | Val | Ser | Thr | Asp | Glu | Val | Tyr | Gly | Glu | Thr | Asp | Glu | Asp | |
| | | 130 | | | | | 135 | | | | | 140 | | | | |
| gct | gct | gta | gga | aac | cat | gaa | gct | tct | cag | ctg | tta | ccg | acg | aat | cct | 480 |
| Ala | Ala | Val | Gly | Asn | His | Glu | Ala | Ser | Gln | Leu | Leu | Pro | Thr | Asn | Pro | |
| 145 | | | | | 150 | | | | | 155 | | | | | 160 | |
| tac | tct | gca | act | aag | gct | ggt | gct | gag | atg | ctt | gtg | atg | gct | tat | ggt | 528 |
| Tyr | Ser | Ala | Thr | Lys | Ala | Gly | Ala | Glu | Met | Leu | Val | Met | Ala | Tyr | Gly | |
| | | | | 165 | | | | | 170 | | | | | 175 | | |
| aga | tca | tat | gga | ttg | cct | gtt | att | acg | act | cgc | ggg | aac | aat | gtt | tat | 576 |
| Arg | Ser | Tyr | Gly | Leu | Pro | Val | Ile | Thr | Thr | Arg | Gly | Asn | Asn | Val | Tyr | |

-continued

|  |  |  |  |  |  |  |  |  |  |  |  |  |  |  |  |
|---|---|---|---|---|---|---|---|---|---|---|---|---|---|---|---|
|  |  | 180 |  |  | 185 |  |  |  | 190 |  |  |  |  |  |  | ggg cct aac cag ttt cct gaa aaa atg att cct aag ttc atc ttg ttg    624
Gly Pro Asn Gln Phe Pro Glu Lys Met Ile Pro Lys Phe Ile Leu Leu
       195                200                  205 gct atg agt ggg aag ccg ctt ccc atc cat gga gat gga tct aat gtc    672
Ala Met Ser Gly Lys Pro Leu Pro Ile His Gly Asp Gly Ser Asn Val
   210                215                  220 cgg agt tac ttg tac tgc gaa gac gtt gct gag gct ttt gag gtt gtt    720
Arg Ser Tyr Leu Tyr Cys Glu Asp Val Ala Glu Ala Phe Glu Val Val
225               230                  235             240 ctt cac aaa gga gaa atc ggt cat gtc tac aat gtc ggc aca aaa aga    768
Leu His Lys Gly Glu Ile Gly His Val Tyr Asn Val Gly Thr Lys Arg
            245                250              255 gaa agg aga gtg atc gat gtg gct aga gac atc tgc aaa ctt ttc ggg    816
Glu Arg Arg Val Ile Asp Val Ala Arg Asp Ile Cys Lys Leu Phe Gly
       260               265                270 aaa gac cct gag tca agc att cag ttt gtg gag aac cgg ccc ttt aat    864
Lys Asp Pro Glu Ser Ser Ile Gln Phe Val Glu Asn Arg Pro Phe Asn
        275             280               285 gat caa agg tac ttc ctt gat gat cag aag ctg aag aaa ttg ggg tgg    912
Asp Gln Arg Tyr Phe Leu Asp Asp Gln Lys Leu Lys Lys Leu Gly Trp
   290              295              300 caa gag cga aca aat tgg gaa gat gga ttg aag aag aca atg gac tgg    960
Gln Glu Arg Thr Asn Trp Glu Asp Gly Leu Lys Lys Thr Met Asp Trp
305               310              315              320 tac act cag aat cct gag tgg tgg ggt gat gtt tct gga gct ttg ctt   1008
Tyr Thr Gln Asn Pro Glu Trp Trp Gly Asp Val Ser Gly Ala Leu Leu
           325               330              335 cct cat ccg aga atg ctt atg atg ccc ggt gga aga ctt tct gat gga   1056
Pro His Pro Arg Met Leu Met Met Pro Gly Gly Arg Leu Ser Asp Gly
       340             345              350 tct agt gag aag aaa gac gtt tca agc aac acg gtc cag aca ttt acg   1104
Ser Ser Glu Lys Lys Asp Val Ser Ser Asn Thr Val Gln Thr Phe Thr
      355              360              365 gtt gta aca cct aag aat ggt gat tct ggt gac aaa gct tcg ttg aag   1152
Val Val Thr Pro Lys Asn Gly Asp Ser Gly Asp Lys Ala Ser Leu Lys
   370              375              380 ttt ttg atc tat ggt aag act ggt tgg ctt ggt ggt ctt cta ggg aaa   1200
Phe Leu Ile Tyr Gly Lys Thr Gly Trp Leu Gly Gly Leu Leu Gly Lys
385              390              395              400 cta tgt gag aag caa ggg att aca tat gag tat ggg aaa gga cgt ctg   1248
Leu Cys Glu Lys Gln Gly Ile Thr Tyr Glu Tyr Gly Lys Gly Arg Leu
            405              410              415 gag gat aga gct tct ctt gtg gcg gat att cgt agc atc aaa cct act   1296
Glu Asp Arg Ala Ser Leu Val Ala Asp Ile Arg Ser Ile Lys Pro Thr
        420             425              430 cat gtg ttt aat gct gct ggt tta act ggc aga ccc aac gtt gac tgg   1344
His Val Phe Asn Ala Ala Gly Leu Thr Gly Arg Pro Asn Val Asp Trp
     435             440              445 tgt gaa tct cac aaa cca gag acc att cgt gta aat gtc gca ggt act   1392
Cys Glu Ser His Lys Pro Glu Thr Ile Arg Val Asn Val Ala Gly Thr
450              455              460 ttg act cta gct gat gtt tgc aga gag aat gat ctc ttg atg atg aac   1440
Leu Thr Leu Ala Asp Val Cys Arg Glu Asn Asp Leu Leu Met Met Asn
465              470              475              480 ttc gcc acc ggt tgc atc ttt gag tat gac gct aca cat cct gag ggt   1488
Phe Ala Thr Gly Cys Ile Phe Glu Tyr Asp Ala Thr His Pro Glu Gly
            485              490              495 tcg ggt ata ggt ttc aag gaa gaa gac aag cca aat ttc ttt ggt tct   1536

```
Ser Gly Ile Gly Phe Lys Glu Glu Asp Lys Pro Asn Phe Phe Gly Ser
                500                 505                 510 ttc tac tcg aaa acc aaa gcc atg gtt gag gag ctc ttg aga gaa ttt     1584
Phe Tyr Ser Lys Thr Lys Ala Met Val Glu Glu Leu Leu Arg Glu Phe
            515                 520                 525 gac aat gta tgt acc ttg aga gtc cgg atg cca atc tcc tca gac cta     1632
Asp Asn Val Cys Thr Leu Arg Val Arg Met Pro Ile Ser Ser Asp Leu
530                 535                 540 aac aac ccg aga aac ttc atc acg aag atc tcg cgc tac aac aaa gtg     1680
Asn Asn Pro Arg Asn Phe Ile Thr Lys Ile Ser Arg Tyr Asn Lys Val
545                 550                 555                 560 gtg gac atc ccg aac agc atg acc gta cta gac gag ctt ctc cca atc     1728
Val Asp Ile Pro Asn Ser Met Thr Val Leu Asp Glu Leu Leu Pro Ile
                565                 570                 575 tct atc gag atg gcg aag aga aac cta aga ggc ata tgg aat ttc acc     1776
Ser Ile Glu Met Ala Lys Arg Asn Leu Arg Gly Ile Trp Asn Phe Thr
            580                 585                 590 aac cca ggg gtg gtg agc cac aac gag ata ttg gag atg tac aag aat     1824
Asn Pro Gly Val Val Ser His Asn Glu Ile Leu Glu Met Tyr Lys Asn
        595                 600                 605 tac atc gag cca ggt ttt aaa tgg tcc aac ttc aca gtg gaa gaa caa     1872
Tyr Ile Glu Pro Gly Phe Lys Trp Ser Asn Phe Thr Val Glu Glu Gln
610                 615                 620 gca aag gtc att gtt gct gct cga agc aac aac gaa atg gat gga tct     1920
Ala Lys Val Ile Val Ala Ala Arg Ser Asn Asn Glu Met Asp Gly Ser
625                 630                 635                 640 aaa cta agc aag gag ttc cca gag atg ctc tcc atc aaa gag tca ctg     1968
Lys Leu Ser Lys Glu Phe Pro Glu Met Leu Ser Ile Lys Glu Ser Leu
                645                 650                 655 ctc aaa tac gtc ttt gaa cca aac aag aga acc taa                     2004
Leu Lys Tyr Val Phe Glu Pro Asn Lys Arg Thr
            660                 665

<210> SEQ ID NO 10
<211> LENGTH: 667
<212> TYPE: PRT
<213> ORGANISM: Arabidopsis thaliana

<400> SEQUENCE: 10

Met Asp Asp Thr Thr Tyr Lys Pro Lys Asn Ile Leu Ile Thr Gly Ala
1               5                   10                  15

Ala Gly Phe Ile Ala Ser His Val Ala Asn Arg Leu Ile Arg Asn Tyr
            20                  25                  30

Pro Asp Tyr Lys Ile Val Val Leu Asp Lys Leu Asp Tyr Cys Ser Asp
        35                  40                  45

Leu Lys Asn Leu Asp Pro Ser Phe Ser Pro Asn Phe Lys Phe Val
50                  55                  60

Lys Gly Asp Ile Ala Ser Asp Asp Leu Val Asn Tyr Leu Leu Ile Thr
65                  70                  75                  80

Glu Asn Ile Asp Thr Ile Met His Phe Ala Ala Gln Thr His Val Asp
                85                  90                  95

Asn Ser Phe Gly Asn Ser Phe Glu Phe Thr Lys Asn Asn Ile Tyr Gly
            100                 105                 110

Thr His Val Leu Leu Glu Ala Cys Lys Val Thr Gly Gln Ile Arg Arg
        115                 120                 125

Phe Ile His Val Ser Thr Asp Glu Val Tyr Gly Glu Thr Asp Glu Asp
        130                 135                 140

Ala Ala Val Gly Asn His Glu Ala Ser Gln Leu Leu Pro Thr Asn Pro
```

-continued

```
            145                 150                 155                 160
        Tyr Ser Ala Thr Lys Ala Gly Ala Glu Met Leu Val Met Ala Tyr Gly
                        165                 170                 175
        Arg Ser Tyr Gly Leu Pro Val Ile Thr Thr Arg Gly Asn Asn Val Tyr
                        180                 185                 190
        Gly Pro Asn Gln Phe Pro Glu Lys Met Ile Pro Lys Phe Ile Leu Leu
                        195                 200                 205
        Ala Met Ser Gly Lys Pro Leu Pro Ile His Gly Asp Gly Ser Asn Val
            210                 215                 220
        Arg Ser Tyr Leu Tyr Cys Glu Asp Val Ala Glu Ala Phe Glu Val Val
        225                 230                 235                 240
        Leu His Lys Gly Glu Ile Gly His Val Tyr Asn Val Gly Thr Lys Arg
                        245                 250                 255
        Glu Arg Arg Val Ile Asp Val Ala Arg Asp Ile Cys Lys Leu Phe Gly
                        260                 265                 270
        Lys Asp Pro Glu Ser Ser Ile Gln Phe Val Glu Asn Arg Pro Phe Asn
                        275                 280                 285
        Asp Gln Arg Tyr Phe Leu Asp Asp Gln Lys Leu Lys Lys Leu Gly Trp
                        290                 295                 300
        Gln Glu Arg Thr Asn Trp Glu Asp Gly Leu Lys Lys Thr Met Asp Trp
        305                 310                 315                 320
        Tyr Thr Gln Asn Pro Glu Trp Trp Gly Asp Val Ser Gly Ala Leu Leu
                        325                 330                 335
        Pro His Pro Arg Met Leu Met Met Pro Gly Gly Arg Leu Ser Asp Gly
                        340                 345                 350
        Ser Ser Glu Lys Lys Asp Val Ser Ser Asn Thr Val Gln Thr Phe Thr
                        355                 360                 365
        Val Val Thr Pro Lys Asn Gly Asp Ser Gly Asp Lys Ala Ser Leu Lys
                        370                 375                 380
        Phe Leu Ile Tyr Gly Lys Thr Gly Trp Leu Gly Gly Leu Leu Gly Lys
        385                 390                 395                 400
        Leu Cys Glu Lys Gln Gly Ile Thr Tyr Glu Tyr Gly Lys Gly Arg Leu
                        405                 410                 415
        Glu Asp Arg Ala Ser Leu Val Ala Asp Ile Arg Ser Ile Lys Pro Thr
                        420                 425                 430
        His Val Phe Asn Ala Ala Gly Leu Thr Gly Arg Pro Asn Val Asp Trp
                        435                 440                 445
        Cys Glu Ser His Lys Pro Glu Thr Ile Arg Val Asn Val Ala Gly Thr
            450                 455                 460
        Leu Thr Leu Ala Asp Val Cys Arg Glu Asn Asp Leu Leu Met Met Asn
        465                 470                 475                 480
        Phe Ala Thr Gly Cys Ile Phe Glu Tyr Asp Ala Thr His Pro Glu Gly
                        485                 490                 495
        Ser Gly Ile Gly Phe Lys Glu Glu Asp Lys Pro Asn Phe Phe Gly Ser
                        500                 505                 510
        Phe Tyr Ser Lys Thr Lys Ala Met Val Glu Glu Leu Leu Arg Glu Phe
                        515                 520                 525
        Asp Asn Val Cys Thr Leu Arg Val Arg Met Pro Ile Ser Ser Asp Leu
            530                 535                 540
        Asn Asn Pro Arg Asn Phe Ile Thr Lys Ile Ser Arg Tyr Asn Lys Val
        545                 550                 555                 560
        Val Asp Ile Pro Asn Ser Met Thr Val Leu Asp Glu Leu Leu Pro Ile
                        565                 570                 575
```

```
Ser Ile Glu Met Ala Lys Arg Asn Leu Arg Gly Ile Trp Asn Phe Thr
            580                 585                 590

Asn Pro Gly Val Val Ser His Asn Glu Ile Leu Glu Met Tyr Lys Asn
        595                 600                 605

Tyr Ile Glu Pro Gly Phe Lys Trp Ser Asn Phe Thr Val Glu Glu Gln
    610                 615                 620

Ala Lys Val Ile Val Ala Ala Arg Ser Asn Asn Glu Met Asp Gly Ser
625                 630                 635                 640

Lys Leu Ser Lys Glu Phe Pro Glu Met Leu Ser Ile Lys Glu Ser Leu
                645                 650                 655

Leu Lys Tyr Val Phe Glu Pro Asn Lys Arg Thr
            660                 665

<210> SEQ ID NO 11
<211> LENGTH: 60
<212> TYPE: DNA
<213> ORGANISM: Stevia rebaudiana

<400> SEQUENCE: 11
gagtaaaatc tataacgaca ctaaggtgga aaagaatat gtaagccaat tcgtagactt      60

<210> SEQ ID NO 12
<211> LENGTH: 33
<212> TYPE: DNA
<213> ORGANISM: Artificial
<220> FEATURE:
<223> OTHER INFORMATION: Artificial nucleic acid

<400> SEQUENCE: 12
cacccatatg gatgcaatgg ctacaactga gaa                                  33

<210> SEQ ID NO 13
<211> LENGTH: 32
<212> TYPE: DNA
<213> ORGANISM: Artificial
<220> FEATURE:
<223> OTHER INFORMATION: Artificial nucleic acid

<400> SEQUENCE: 13
agatctctag tttcttgcta gcacggtgat tt                                   32

<210> SEQ ID NO 14
<211> LENGTH: 35
<212> TYPE: DNA
<213> ORGANISM: Artificial
<220> FEATURE:
<223> OTHER INFORMATION: Artificial nucleic acid

<400> SEQUENCE: 14
cacccatatg gcggaacaac aaaagatcaa gaaat                                35

<210> SEQ ID NO 15
<211> LENGTH: 35
<212> TYPE: DNA
<213> ORGANISM: Artificial
<220> FEATURE:
<223> OTHER INFORMATION: Artificial nucleic acid

<400> SEQUENCE: 15
ggatccttaa gccttaatta gctcacttac aaatt                                35

<210> SEQ ID NO 16
```

<211> LENGTH: 29
<212> TYPE: DNA
<213> ORGANISM: Artificial
<220> FEATURE:
<223> OTHER INFORMATION: Artificial nucleic acid

<400> SEQUENCE: 16
cacccatatg gaaaataaaa cggagacca                                          29

<210> SEQ ID NO 17
<211> LENGTH: 32
<212> TYPE: DNA
<213> ORGANISM: Artificial
<220> FEATURE:
<223> OTHER INFORMATION: Artificial nucleic acid

<400> SEQUENCE: 17
ggatccttac aacgatgaaa tgtaagaaac ta                                      32

<210> SEQ ID NO 18
<211> LENGTH: 33
<212> TYPE: DNA
<213> ORGANISM: Artificial
<220> FEATURE:
<223> OTHER INFORMATION: Artificial nucleic acid

<400> SEQUENCE: 18
acagatctat ggatgcaatg gctacaactg aga                                     33

<210> SEQ ID NO 19
<211> LENGTH: 34
<212> TYPE: DNA
<213> ORGANISM: Artificial
<220> FEATURE:
<223> OTHER INFORMATION: Artificial nucleic acid

<400> SEQUENCE: 19
tagtcgacta gtttcttgct agcacggtga tttc                                    34

<210> SEQ ID NO 20
<211> LENGTH: 42
<212> TYPE: DNA
<213> ORGANISM: Artificial
<220> FEATURE:
<223> OTHER INFORMATION: Artificial nucleic acid

<400> SEQUENCE: 20
aagcggccgc atgtacaacg ttacttatca tcaaaattca aa                           42

<210> SEQ ID NO 21
<211> LENGTH: 31
<212> TYPE: DNA
<213> ORGANISM: Artificial
<220> FEATURE:
<223> OTHER INFORMATION: Artificial nucleic acid

<400> SEQUENCE: 21
cgttaattaa ctctcatgat cgatggcaac c                                       31

<210> SEQ ID NO 22
<211> LENGTH: 34
<212> TYPE: DNA
<213> ORGANISM: Artificial
<220> FEATURE:
<223> OTHER INFORMATION: Artificial nucleic acid

<400> SEQUENCE: 22

```
aagcggccgc atggcggaac aacaaaagat caag                                    34

<210> SEQ ID NO 23
<211> LENGTH: 37
<212> TYPE: DNA
<213> ORGANISM: Artificial
<220> FEATURE:
<223> OTHER INFORMATION: Artificial nucleic acid

<400> SEQUENCE: 23
cgttaattaa gccttaatta gctcacttac aaattcg                                 37

<210> SEQ ID NO 24
<211> LENGTH: 33
<212> TYPE: DNA
<213> ORGANISM: Artificial
<220> FEATURE:
<223> OTHER INFORMATION: Artificial nucleic acid

<400> SEQUENCE: 24
aaggatccat ggaaaataaa acggagacca ccg                                     33

<210> SEQ ID NO 25
<211> LENGTH: 44
<212> TYPE: DNA
<213> ORGANISM: Artificial
<220> FEATURE:
<223> OTHER INFORMATION: Artificial nucleic acid

<400> SEQUENCE: 25
gcgtcgactt acaacgatga aatgtaagaa actagagact ctaa                         44

<210> SEQ ID NO 26
<211> LENGTH: 33
<212> TYPE: DNA
<213> ORGANISM: Artificial
<220> FEATURE:
<223> OTHER INFORMATION: Artificial nucleic acid

<400> SEQUENCE: 26
ggatccatgg atgatactac gtataagcca aag                                     33

<210> SEQ ID NO 27
<211> LENGTH: 32
<212> TYPE: DNA
<213> ORGANISM: Artificial
<220> FEATURE:
<223> OTHER INFORMATION: Artificial nucleic acid

<400> SEQUENCE: 27
ctcgagttag gttctcttgt ttggttcaaa ga                                      32

<210> SEQ ID NO 28
<211> LENGTH: 22
<212> TYPE: DNA
<213> ORGANISM: Artificial
<220> FEATURE:
<223> OTHER INFORMATION: Artificial nucleic acid

<400> SEQUENCE: 28
caagtcccca accaaattcc gt                                                 22

<210> SEQ ID NO 29
<211> LENGTH: 21
<212> TYPE: DNA
```

```
<213> ORGANISM: Artificial
<220> FEATURE:
<223> OTHER INFORMATION: Artificial nucleic acid

<400> SEQUENCE: 29
cacgaacccg tctggcaact c                                        21

<210> SEQ ID NO 30
<211> LENGTH: 25
<212> TYPE: DNA
<213> ORGANISM: Artificial
<220> FEATURE:
<223> OTHER INFORMATION: Artificial nucleic acid

<400> SEQUENCE: 30
cccgtgtgat tcttccact tgttc                                     25

<210> SEQ ID NO 31
<211> LENGTH: 21
<212> TYPE: DNA
<213> ORGANISM: Artificial
<220> FEATURE:
<223> OTHER INFORMATION: Artificial nucleic acid

<400> SEQUENCE: 31
caagaaccca tctggcaacg g                                        21

<210> SEQ ID NO 32
<211> LENGTH: 23
<212> TYPE: DNA
<213> ORGANISM: Artificial
<220> FEATURE:
<223> OTHER INFORMATION: Artificial nucleic acid

<400> SEQUENCE: 32
gctttgtcac cagaatcacc att                                      23

<210> SEQ ID NO 33
<211> LENGTH: 28
<212> TYPE: DNA
<213> ORGANISM: Artificial
<220> FEATURE:
<223> OTHER INFORMATION: Artificial nucleic acid

<400> SEQUENCE: 33
gattattaaa cttctttgcg tccatcca                                 28

<210> SEQ ID NO 34
<211> LENGTH: 32
<212> TYPE: DNA
<213> ORGANISM: Artificial
<220> FEATURE:
<223> OTHER INFORMATION: Artificial nucleic acid

<400> SEQUENCE: 34
cctctatact ttaacgtcaa ggagaaaaaa cc                            32

<210> SEQ ID NO 35
<211> LENGTH: 39
<212> TYPE: DNA
<213> ORGANISM: Artificial
<220> FEATURE:
<223> OTHER INFORMATION: Artificial nucleic acid

<400> SEQUENCE: 35
tgccgcgcgg cagccatatg tacaacgtta cttatcatc                     39
```

```
<210> SEQ ID NO 36
<211> LENGTH: 39
<212> TYPE: DNA
<213> ORGANISM: Artificial
<220> FEATURE:
<223> OTHER INFORMATION: Artificial nucleic acid

<400> SEQUENCE: 36
gttagcagcc ggatccttaa ctctcatgat cgatggcaa                          39
```